US009982274B2

(12) United States Patent
Desai et al.

(10) Patent No.: US 9,982,274 B2
(45) Date of Patent: May 29, 2018

(54) AXMI115 VARIANT INSECTICIDAL GENE AND METHODS FOR ITS USE

(71) Applicant: ATHENIX CORP., Morrisville, NC (US)

(72) Inventors: Nalini Manoj Desai, Chapel Hill, NC (US); Volker Heinrichs, Wedemark (DE); Duane Lehtinen, Cary, NC (US)

(73) Assignee: Athenix Corp., Morrisville, NC (US)

( * ) Notice: Subject to any disclaimer, the term of this patent is extended or adjusted under 35 U.S.C. 154(b) by 0 days. days.

(21) Appl. No.: 14/851,555

(22) Filed: Sep. 11, 2015

(65) Prior Publication Data

US 2015/0376244 A1    Dec. 31, 2015

Related U.S. Application Data

(62) Division of application No. 13/439,269, filed on Apr. 4, 2012, now abandoned.

(60) Provisional application No. 61/471,848, filed on Apr. 5, 2011.

(51) Int. Cl.
    C12N 15/82    (2006.01)
    C07K 14/325   (2006.01)
    A01N 63/02    (2006.01)
    C07K 14/32    (2006.01)

(52) U.S. Cl.
    CPC ......... C12N 15/8286 (2013.01); A01N 63/02 (2013.01); C07K 14/32 (2013.01); C07K 14/325 (2013.01); C12N 15/8279 (2013.01); C07K 2319/00 (2013.01); C07K 2319/24 (2013.01)

(58) Field of Classification Search
    None
    See application file for complete search history.

(56) References Cited

FOREIGN PATENT DOCUMENTS

WO    WO 2010/003065    *  1/2010

OTHER PUBLICATIONS

Argolo-Filho et al, 2014, Insects 5:62-91.*

* cited by examiner

Primary Examiner — Anne Kubelik

(57) ABSTRACT

Compositions and methods for conferring pesticidal activity to bacteria, plants, plant cells, tissues and seeds are provided. The toxin coding sequences can be used in DNA constructs or expression cassettes for expression in plants and bacteria. Compositions include transformed bacteria, plants, plant cells, tissues, and seeds. In particular, polynucleotide sequences and the toxin proteins encoded thereby are provided. Also provided are antibodies specifically binding to those amino acid sequences. In particular, the invention encompasses nucleotide sequences encoding fusion proteins, as well as biologically active variants and fragments thereof, wherein the fusion protein contains the C-terminal portion of SEQ ID NO:43. The fusion protein may also contain the N-terminal portion of SEQ ID NO:45. The invention also includes the nucleotide sequence of SEQ ID NO:47 and 1-14, or a nucleotide sequence encoding the amino acid sequence set forth in SEQ ID NO:2, 3, 7-14 and 47, including biologically active variants and fragments thereof.

24 Claims, 2 Drawing Sheets

SEQUENCE LISTING

```
<160> NUMBER OF SEQ ID NOS: 48

<210> SEQ ID NO 1
<211> LENGTH: 2415
<212> TYPE: DNA
<213> ORGANISM: Artificial
<220> FEATURE:
<223> OTHER INFORMATION: Axmi115 variant sequence

<400> SEQUENCE: 1
atgaacatga acaacaccaa gctcaatgca agggcgctgc cgagcttcat cgactacttc        60
aatggcatct atggcttcgc caccggcatc aaggacatca tgaacatgat cttcaagacc       120
gacaccggcg gcaacctcac cttggatgag atcctcaaga accagcagct gctgaatgag       180
atctcaggca agctggacgg cgtcaatgga agcctcaacg acctcattgc tcaaggcaac       240
ctcaacaccg agctgagcaa ggagatcctc aagattgcaa atgagcagaa ccaggtgctg       300
aatgatgtca caacaagct ggacgccatc aacaccatgc tgcacatcta cctgccaaag        360
atcacctcaa tgctctctga tgtgatgaag cagaactacg cgctgagcct ccagattgag       420
tacctctcaa agcagctgca agagatctcc gacaagctgg acatcatcaa tgtcaatgtg       480
ctcatcaaca gcaccttgac agagatcacg ccggcctacc agaggatcaa gtatgtcaat       540
gagaagttcg acaagctcac cttcgccacc gagagcaccc tccgcgccaa gcaaggcatc       600
ttcaatgaag attcatttga caacaacacc ttggagaact tgacagacct cgccgagctg       660
gccaagagca tcaccaagaa tgatgtggac agcttcgagt tctacctcca caccttccat       720
gatgtgctca tcgcaacaa cctctttgga agaagcgcgc tcaagacggc atcagagctc       780
atcaccaagg atgagatcaa gacaagcggc agcgagatcg caaggtcta cagcttcctc       840
```

| | |
|---|---:|
| atcgtgctga catcattgca agccaaggcc ttcctcacct tgacaacctg ccgcaagttg | 900 |
| ctgggcctct ccgacatcga ctacacctcc atcatgaatg agcacctcaa caatgagaag | 960 |
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca agtgcaagag ctacctcagg | 1560 |
| gagtacctgc tggagagtga tttgaagaac aaggagacag gctgatcgc gccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |
| ctcttcaccc aaggagatgg agagttcagc cagttcatcg gcgacaagct aaagcccaac | 1800 |
| accgactaca tcatccagta caccgtcaag ggcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca agaggaggct acttccgcca aagcctcaac | 2160 |
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc cacagcttca gagacatcag catcaaggag | 2400 |
| aagattgaat agtaa | 2415 |

<210> SEQ ID NO 2
<211> LENGTH: 2397
<212> TYPE: DNA
<213> ORGANISM: Artificial
<220> FEATURE:
<223> OTHER INFORMATION: Axmi115 variant sequence

<400> SEQUENCE: 2

| | |
|---|---:|
| atgaacatga acaacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg gcaacctcac cttggatgag atcctcaaga ccagcagct gctgaatgag | 180 |
| atctcaggca gctggacgg cgtcaatgga agcctcaacg acctcattgc tcaaggcaac | 240 |
| ctcaacaccg agctgagcaa ggagatcctc aagattgcaa atgagcagaa ccaggtgctg | 300 |
| aatgatgtca caacaagct ggacgccatc aacaccatgc tgcacatcta cctgccaaag | 360 |
| atcacctcaa tgctctctga tgtgatgaag cagaactacg cgctgagcct ccagattgag | 420 |
| tacctctcaa agcagctgca agagatctcc gacaagctgg acatcatcaa tgtcaatgtg | 480 |

```
ctcatcaaca gcaccttgac agagatcacg ccggcctacc agaggatcaa gtatgtcaat      540
gagaagtttg aggagctcac cttcgccacc gagacaacat tgaaggtgaa gaaggacagc      600
tcgccggcgg acatcctgga tgagctcacc gagctaacag agctggccaa gagcgtcacc      660
aagaatgatg ttgatggctt cgagttctac ctcaacacct tccatgatgt gatggtgggc      720
aacaacctct tcggccgctc ggcgctcaag acggcgtcgg agctgatcgc caaggagaat      780
gtcaagacaa gtggatcaga ggtgggcaat gtctacaact tcctcatcgt gctgacggcg      840
ctgcaagcca aggccttcct caccttgaca acctgccgca agttgctggg cctctccgac      900
atcgactaca cctccatcat gaatgagcac ctcaacaatg aagaatga gttcagagac        960 aacatcctgc cggcgctgag caacaagttc agcaacccaa gctacgccaa gaccatcggc     1020
tcagacaact acgccaaggt gatcctggag agcgagcctg gctacgcgct ggtgggcttc     1080
gagatcatca atgatccaat tcctgttctc aaggcctaca aggccaagct gaagcagaac     1140
taccaggtgg acaaccagag cttgagcgag atcgtctacc tggacatcga caagctcttc     1200
tgcccggaga actcagagca gaagtactac accaagaacc tcaccttccc tgatggatat     1260
gtcatcacca agatcacctt cgagaagaag ctgaacaacc tcatctacga ggccaccgcc     1320
aacttctatg atccatcaac aggagacatc gacctcaaca gaagcaagt ggagagcacc      1380 ttccctcaaa cagactacat caccatggac attggagatg atgatggcat ctacatgccg     1440
ctcggcgtca tctcagaaac cttcttgacg cccatcaaca gcttcggcct ggaggtggac     1500
gccaagagca agaccttgac gctcaagtgc aagagctacc tcagggagta cctgctggag     1560
agtgatttga gaacaagga gacagggctg atcgcgccgc caaatgtgtt catcagcaat      1620
gtggtgaaga actgggacat cgaggaggat tcattggagc catgggtggc caacaacaag     1680
aatgcttatg tggacaacac cggcggcatt gaaagaagca aggcgctctt cacccaagga     1740
gatggagagt tcagccagtt catcggcgac aagctaaagc ccaacaccga ctacatcatc     1800
cagtacaccg tcaagggcaa gccggccatc tacctcaaga caagagcac cggctacatc      1860 acctacgagg acaccaatgg aaattctgag gagttccaaa caattgctgt gaagttcacc     1920
tcagaaacag atttgagcca gacccacctg gtgttcaaga gccaaaatgg atatgaagca     1980
tggggagaca acttcatcat cctggaggcc aagctcttcg agacaccaga aagcccggag     2040
ctcatcaagt tcaatgattg ggagaggttc ggcaccacct acatcaccgg caatgagctg     2100
aggattgatc attcaagagg aggctacttc cgccaaagcc tcaacatcga cagctacagc     2160
acctacgacc tcagcttcag cttcagcggc tctgggcca aggtgattgt gaagaacagc      2220
cgcggcgtgg tgctcttcga gaaggtgaag aacaatggaa gcagctatga ggacatctca     2280
gagagcttca ccaccgccag caacaaggat ggcttcttca tcgagctcac cgccgagagg     2340
acaagcagca ccttccacag cttcagagac atcagcatca aggagaagat tgaataa        2397
```

<210> SEQ ID NO 3
<211> LENGTH: 2421
<212> TYPE: DNA
<213> ORGANISM: Artificial
<220> FEATURE:
<223> OTHER INFORMATION: Axmi115 variant sequence

<400> SEQUENCE: 3

```
atggcacatc accaccacca tcacggatcc accatgaaca tgaacaacac caagctcaat       60
gcaagggcgc tgccgagctt catcgactac ttcaatggca tctatggctt cgccaccggc      120
```

```
atcaaggaca tcatgaacat gatcttcaag accgacaccg gcggcaacct caccttggat    180
gagatcctca agaaccagca gctgctgaat gagatctcag gcaagctgga cggcgtcaat    240
ggaagcctca acgacctcat tgctcaaggc aacctcaaca ccgagctgag caaggagatc    300
ctcaagattg caaatgagca gaaccaggtg ctgaatgatg tcaacaacaa gctggacgcc    360
atcaacacca tgctgcacat ctacctgcca aagatcacct caatgctctc tgatgtgatg    420
aagcagaact acgcgctgag cctccagatt gagtacctct caaagcagct gcaagagatc    480
tccgacaagc tggacatcat caatgtcaat gtgctcatca acagcacctt gacagagatc    540
acgccggcct accagaggat caagtatgtc aatgagaagt ttgaggagct caccttcgcc    600
accgagacaa cattgaaggt gaagaaggac agctcgccgg cggacatcct ggatgagctc    660
accgagctaa cagagctggc caagagcgtc accaagaatg atgttgatgg cttcgagttc    720
tacctcaaca ccttccatga tgtgatggtg gcaacaacc tcttcggccg ctcggcgctc    780
aagacggcgt cggagctgat cgccaaggag aatgtcaaga caagtggatc agaggtgggc    840
aatgtctaca acttcctcat cgtgctgacg gcgctgcaag ccaaggcctt cctcaccttg    900
acaacctgcc gcaagttgct gggcctcgcc gacatcgact acacctccat catgaatgag    960
cacctcaaca aggagaagga ggagttccgc gtcaacatcc tgccaacatt gagcaacacc   1020
ttcagcaacc ccaactacgc caaggtgaag ggctcagatg aagatgccaa gatgattgtg   1080
gaggccaagc ctggccatgc tctggtgggc ttcgagatga gcaacgacag catcaccgtg   1140
ctgaaggtct acgaggccaa gctgaagcag aactaccagg tggacaagga cagcttgtct   1200
gaggtgatct acgcgacat ggacaagctg ctatgtccag atcaaagcga gcagatctac   1260
tacaccaaca acatcgtctt tccaaatgaa tatgtcatca ccaagatcga cttcaccaag   1320
aagatgaaaa cattgagata tgaggtgacg gccaacagct acgacagcag caccggcgag   1380
atcgacctca caagaagaa ggtggagagc tcagaagctg agtacaggac gctctccgcc   1440
aaggatgatg gcgtctacat gccgctcggc gtcatctcag aaaccttctt gacgcccatc   1500
aatggcttcg gcctccaagc tgatgagaac agcaggctca tcaccttgac ctgcaagagc   1560
tacctcaggg agctgctgct ggccaccgac ctcagcaaca aggagacaaa gctcatcgtg   1620
ccgccatcag gcttcatcag caacatcgtg gagaatggca acctggaagg agagaacctg   1680
gagccatgga tagccaacaa caagaatgct tatgttgatc acaccggcgg cgtcaatgga   1740
acaagggcgc tctatgttca caaggatgga ggcttcagcc agttcatcgg cgacaagctg   1800
aagcccaaga cagaatatgt catccagtac accgtcaagg gcaagccggc catctacctc   1860
aagaacaaga gcaccggcta catcacctac gaggacacca atggaaattc tgaggagttc   1920
caaacaattg ctgtgaagtt cacctcagaa acagatttga gccagaccca cctggtgttc   1980
aagagccaaa atggatatga agcatgggga gacaacttca tcatcctgga ggccaagctc   2040
ttcgagacac cagaaagccc ggagctcatc aagttcaatg attgggagag gttcggcacc   2100
acctacatca ccggcaatga gctgaggatt gatcattcaa gaggaggcta cttccgccaa   2160
agcctcaaca tcgacagcta cagcacctac gacctcagct tcagcttcag cggcctctgg   2220
gccaaggtga ttgtgaagaa cagccgcggc gtggtgctct cgagaaggt gaagaacaat   2280 ggaagcagct atgaggacat ctcagagagc ttcaccaccg ccagcaacaa ggatggcttc   2340
ttcatcgagc tcaccgccga gaggacaagc agcaccttcc acagcttcag agacatcagc   2400
atcaaggaga agattgaata a                                             2421
```

```
<210> SEQ ID NO 4
<211> LENGTH: 2412
<212> TYPE: DNA
<213> ORGANISM: Artificial
<220> FEATURE:
<223> OTHER INFORMATION: Axmi115 variant sequence

<400> SEQUENCE: 4
```

| | | | | | |
|---|---|---|---|---|---|
| atgaacatga | acaacaccaa | gctcaatgca | agggcgctgc | cgagcttcat | cgactacttc     60 |
| aatggcatct | atggcttcgc | caccggcatc | aaggacatca | tgaacatgat | cttcaagacc    120 |
| gacaccggcg | gcaacctcac | cttggatgag | atcctcaaga | accagcagct | gctgaatgag    180 |
| atctcaggca | agctggacgg | cgtcaatgga | agcctcaacg | acctcattgc | tcaaggcaac    240 |
| ctcaacaccg | agctgagcaa | ggagatcctc | aagattgcaa | atgagcagaa | ccaggtgctg    300 |
| aatgatgtca | caacaagct | ggacgccatc | aacaccatgc | tgcacatcta | cctgccaaag    360 |
| atcacctcaa | tgctctctga | tgtgatgaag | cagaactacg | cgctgagcct | ccagattgag    420 |
| tacctctcaa | gcagctgca | agagatctcc | gacaagctgg | acatcatcaa | tgtcaatgtg    480 |
| ctcatcaaca | gcaccttgac | agagatcacg | ccggcctacc | agaggatcaa | gtatgtcaat    540 |
| gagaagttcg | acaagctcac | cttcgccacc | gagagcaccc | tccgcgccaa | gcaaggcatc    600 |
| ttcaatgaag | attcatttga | caacaacacc | ttggagaact | tgacagacct | cgccgagctg    660 |
| gccaagagca | tcaccaagaa | tgatgtggac | agcttcgagt | tctacctcca | caccttccat    720 |
| gatgtgctca | tcggcaacaa | cctctttgga | agaagcgcgc | tcaagacggc | atcagagctc    780 |
| atcaccaagg | atgagatcaa | gacaagcggc | agcgagatcg | gcaaggtcta | cagcttcctc    840 |
| atcgtgctga | catcattgca | agccaaggcc | ttcctcacct | tgacaacctg | ccgcaagttg    900 |
| ctgggcctct | ccgacatcga | ctacacctcc | atcatgaatg | agcacctcaa | caatgagaag    960 |
| aatgagttca | gagacaacat | cctgccggcg | ctgagcaaca | agttcagcaa | cccaagctac   1020 |
| gccaagacca | tcggctcaga | caactacgcc | aaggtgatcc | tggagagcga | gcctggctac   1080 |
| gcgctggtgg | gcttcgagat | catcaatgat | ccaattcctg | ttctcaaggc | ctacaaggcc   1140 |
| aagctgaagc | agaactacca | ggtgacaac | cagagcttga | gcgagatcgt | ctacctggac   1200 |
| atcgacaagc | tcttctgccc | ggagaactca | gagcagaagt | actacaccaa | gaacctcacc   1260 |
| ttccctgatg | gatatgtcat | caccaagatc | accttcgaga | agaagctgaa | caacctcatc   1320 |
| tacgaggcca | ccgccaactt | ctatgatcca | tcaacaggag | acatcgacct | caacaagaag   1380 |
| caagtggaga | gcaccttccc | tcaaacagac | tacatcacca | tggacattgg | agatgatgat   1440 |
| ggcatctaca | tgccgctcgg | cgtcatctca | gaaaccttct | tgacgcccat | caacagcttc   1500 |
| ggcctggagg | tggacgccaa | gagcaagacc | ttgacgctca | gtgcaagag | ctacctcagg   1560 |
| gagtacctgc | tggagagtga | tttgaagaac | aaggagacag | gctgatcgc | gccgccaaat   1620 |
| gtgttcatca | gcaatgtggt | gaagaactgg | gacatcgagg | aggattcatt | ggagccatgg   1680 |
| gtggccaaca | acaagaatgc | ttatgtggac | aacaccggcg | gcattgaaag | aagcaaggcg   1740 |
| ctcttcaccc | caaggagatgg | aaagttcagc | cagttcatcg | gcgacaagct | aaagcccaac   1800 |
| accgactaca | tcatccagta | caccgtcaag | ggcaagccgg | ccatctacct | caagaacaag   1860 |
| agcaccggct | acatcaccta | cgaggacacc | aatggaaatt | ctgaggagtt | ccaaacaatt   1920 |
| gctgtgaagt | tcacctcaga | aacagatttg | agccagaccc | acctggtgtt | caagagccaa   1980 |
| aatggatatg | aagcatgggg | agacaacttc | atcatcctgg | aggccaagct | cttcgagaca   2040 |
| ccagaaagcc | cggagctcat | caagttcaat | gattgggaga | ggttcggcac | cacctacatc   2100 |

```
accggcaatg agctgaggat tgatcattca agaggaggct acttccgcca aagcctcaac    2160
atcgacagct acagcaccta cgacctcagc ttcagcttca gcggcctctg ggccaaggtg    2220
attgtgaaga acagccgcgg cgtggtgctc ttcgagaagg tgaagaacaa tggaagcagc    2280
tatgaggaca tctcagagag cttcaccacc gccagcaaca aggatggctt cttcatcgag    2340
ctcaccgccg agaggacaag cagcaccttc cacagcttca gagacatcag catcaaggag    2400
aagattgaat aa                                                        2412

<210> SEQ ID NO 5
<211> LENGTH: 2412
<212> TYPE: DNA
<213> ORGANISM: Artificial
<220> FEATURE:
<223> OTHER INFORMATION: Axmi115 variant sequence

<400> SEQUENCE: 5
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg caacctcac cttggatgag atcctcaaga ccagcagct gctgaatgag      180 atctcaggca agctggacgg cgtcaatgga agcctcaacg acctcattgc tcaaggcaac     240
ctcaacaccg agctgagcaa ggagatcctc aagattgcaa atgagcagaa ccaggtgctg     300
aatgatgtca caacaagct ggacgccatc aacaccatgc tgcacatcta cctgccaaag      360
atcacctcaa tgctctctga tgtgatgaag cagaactacg cgctgagcct ccagattgag     420
tacctctcaa gcagctgca agagatctcc gacaagctgg acatcatcaa tgtcaatgtg      480
ctcatcaaca gcaccttgac agagatcacg ccggcctacc agaggatcaa gtatgtcaat     540
gagaagttcg acaagctcac cttcgccacc gagagcaccc tccgcgccaa gcaaggcatc     600
ttcaatgaag attcatttga caacaacacc ttggagaact tgacagacct cgccgagctg     660
gccaagagca tcaccaagaa tgatgtggac agcttcgagt tctacctcca caccttccat     720
gatgtgctca tcggcaacaa cctctttgga agaagcgcgc tcaagacggc atcagagctc     780
atcaccaagg atgagatcaa gacaagcggc agcgagatcg gcaaggtcta cagcttcctc     840
atcgtgctga catcattgca agccaaggcc ttcctcacct tgacaacctg ccgcaagttg     900
ctgggcctct ccgacatcga ctacacctcc atcatgaatg agcacctcaa caatgagaag     960
aatgagttca gagacaacat cctgccggcg ctgagcaaca agttcagcaa cccaagctac    1020
gccaagacca tcggctcaga caactacgcc aaggtgatcc tggagagcga gcctggctac    1080
gcgctggtgg gcttcgagat catcaatgat ccaattcctg ttctcaaggc ctacaaggcc    1140
aagctgaagc agaactacca ggtggacaac cagagcttga gcgagatcgt ctacctggac    1200
atcgacaagc tcttctgccc ggagaactca gagcagaagt actacaccaa gaacctcacc    1260
ttccctgatg gatatgtcat caccaagatc accttcgaga gaagctgaa caacctcatc     1320 tacgaggcca ccgccaactt ctatgatcca tcaacaggag acatcgacct caacaagaag    1380
caagtggaga gcaccttccc tcaaacagac tacatcacca tggacattgg agatgatgat    1440
ggcatctaca tgccgctcgg cgtcatctca gaaaccttct tgacgcccat caacagcttc    1500
ggcctggagg tggacgccaa gagcaagacc ttgacgctca gtgcaagag ctacctcagg    1560 gagtacctgc tggagagtga tttgaagaac aaggagacag gctgatcgc gccgccaaat    1620 gtgttcatca gcaatgtggt gaagaactgg gacatcgagg aggattcatt ggagccatgg    1680
gtggccaaca acaagaatgc ttatgtggac aacaccggcg gcattgaaag aagcaaggcg    1740
```

```
ctcttcaccc aaggagatgg agagttcagc cagttcatcg gcgacaagct aaagcccaac      1800
accgactaca tcatccagta caccgtcaag ggcaagccgg ccatctacct caagaacaag      1860
agcaccggct acatcaccta cgaggacacc aatggaaatt ctgaggagtt ccaaacaatt      1920
gctgtgaagt tcacctcaga aacagatttg agccagaccc acctggtgtt caagagccaa      1980
aatggatatg aagcatgggg agacaacttc atcatcctgg aggccaagct cttcgagaca      2040
ccagaaagcc cggagctcat caagttcaat gattgggaga ggttcggcac cacctacatc      2100
accggcaatg agctgaggat tgatcattca agaggaggct acttccgcca aagcctcaac      2160
atcgacagct acagcaccta cgacctcagc ttcagcttca gcggcctctg ggccaaggtg      2220
attgtgaaga acagccgcgg cgtggtgctc ttcgagaagg tgaagaacaa tggaagcagc      2280
tatgaggaca tctcagagag cttcaccacc atgagcaaca aggatggctt cttcatcgag      2340
ctcaccgccg agaggacaag cagcaccttc cacagcttca gagacatcag catcaaggag      2400
aagattgaat aa                                                         2412

<210> SEQ ID NO 6
<211> LENGTH: 2412
<212> TYPE: DNA
<213> ORGANISM: Artificial
<220> FEATURE:
<223> OTHER INFORMATION: Axmi115 variant sequence

<400> SEQUENCE: 6
atgaacatga acaacaccaa gctcaatgca agggcgctgc cgagcttcat cgactacttc        60
aatggcatct atggcttcgc caccggcatc aaggacatca tgaacatgat cttcaagacc       120
gacaccggcg gcaacctcac cttggatgag atcctcaaga accagcagct gctgaatgag       180
atctcaggca agctggacgg cgtcaatgga agcctcaacg acctcattgc tcaaggcaac       240
ctcaacaccg agctgagcaa ggagatcctc aagattgcaa atgagcagaa ccaggtgctg       300
aatgatgtca acaacaagct ggacgccatc aacaccatgc tgcacatcta cctgccaaag       360
atcacctcaa tgctctctga tgtgatgaag cagaactacg cgctgagcct ccagattgag       420
tacctctcaa agcagctgca agagatctcc gacaagctgg acatcatcaa tgtcaatgtg       480
ctcatcaaca gcaccttgac agagatcacg ccggcctacc agaggatcaa gtatgtcaat       540
gagaagttcg acaagctcac cttcgccacc gagagcaccc tccgcgccaa gcaaggcatc       600
ttcaatgaag attcatttga caacaacacc ttggagaact tgacagacct cgccgagctg       660
gccaagagca tcaccaagaa tgatgtggac agcttcgagt tctacctcca caccttccat       720
gatgtgctca tcggcaacaa cctctttgga agaagcgcgc tcaagacggc atcagagctc       780
atcaccaagg atgagatcaa gacaagcggc agcgagatcg gcaaggtcta cagcttcctc       840
atcgtgctga catcattgca agccaaggcc ttcctcacct tgacaacctg ccgcaagttg       900
ctgggcctct ccgacatcga ctacacctcc atcatgaatg agcacctcaa caatgagaag       960
aatgagttca gagacaacat cctgccggcg ctgagcaaca agttcagcaa cccaagctac      1020
gccaagacca tcggctcaga caactacgcc aaggtgatcc tggagagcga gcctggctac      1080
gcgctggtgg gcttcgagat catcaatgat ccaattcctg ttctcaaggc ctacaaggcc      1140
aagctgaagc agaactacca ggtggacaac cagagcttga gcgagatcgt ctacctggac      1200
atcgacaagc tcttctgccc ggagaactca gagcagaagt actacaccaa gaacctcacc      1260
ttccctgatg gatatgtcat caccaagatc accttcgaga agaagctgaa caacctcatc      1320
```

| tacgaggcca | ccgccaactt | ctatgatcca | tcaacaggag | acatcgacct | caacaagaag | 1380 |
| caagtggaga | gcaccttccc | tcaaacagac | tacatcacca | tggacattgg | agatgatgat | 1440 |
| ggcatctaca | tgccgctcgg | cgtcatctca | gaaaccttct | tgacgcccat | caacagcttc | 1500 |
| ggcctggagg | tggacgccaa | gagcaagacc | ttgacgctca | agtgcaagag | ctacctcagg | 1560 |
| gagtacctgc | tggagagtga | tttgaagaac | aaggagacag | gctgatcgc | ccgccaaat | 1620 |
| gtgttcatca | gcaatgtggt | gaagaactgg | gacatcgagg | aggattcatt | ggagccatgg | 1680 |
| gtggccaaca | acaagaatgc | ttatgtggac | aacaccggcg | gcattgaaag | aagcaaggcg | 1740 |
| ctcttcaccg | taggagatgg | agagttcagc | cagttcatcg | gcgacaagct | aaagcccaac | 1800 |
| accgactaca | tcatccagta | caccgtcaag | ggcaagccgg | ccatctacct | caagaacaag | 1860 |
| agcaccggct | acatcaccta | cgaggacacc | aatggaaatt | ctgaggagtt | ccaaacaatt | 1920 |
| gctgtgaagt | tcacctcaga | aacagatttg | agccagaccc | acctggtgtt | caagagccaa | 1980 |
| aatggatatg | aagcatgggg | agacaacttc | atcatcctgg | aggccaagct | cttcgagaca | 2040 |
| ccagaaagcc | cggagctcat | caagttcaat | gattgggaga | ggttcggcac | cacctacatc | 2100 |
| accggcaatg | agctgaggat | tgatcattca | agaggaggct | acttccgcca | aagcctcaac | 2160 |
| atcgacagct | cagcaccta | cgacctcagc | ttcagcttca | gcggcctctg | gccaaggtg | 2220 |
| attgtgaaga | acagccgcgg | cgtggtgctc | ttcgagaagg | tgaagaacaa | tggaagcagc | 2280 |
| tatgaggaca | tctcagagag | cttcaccacc | gccagcaaca | aggatggctt | cttcatcgag | 2340 |
| ctcaccgccg | agaggacaag | cagcaccttc | cacagcttca | gagacatcag | catcaaggag | 2400 |
| aagattgaat | aa | | | | | 2412 |

<210> SEQ ID NO 7
<211> LENGTH: 2409
<212> TYPE: DNA
<213> ORGANISM: Artificial
<220> FEATURE:
<223> OTHER INFORMATION: Axmi115 variant sequence

<400> SEQUENCE: 7

| atgaacatga | acaacaccaa | gctcaatgca | agggcgctgc | cgagcttcat | cgactacttc | 60 |
| aatggcatct | atggcttcgc | caccggcatc | aaggacatca | tgaacatgat | cttcaagacc | 120 |
| gacaccggcg | gcaacctcac | cttggatgag | atcctcaaga | ccagcagct | gctgaatgag | 180 |
| atctcaggca | agctggacgg | cgtcaatgga | agcctcaacg | acctcattgc | tcaaggcaac | 240 |
| ctcaacaccg | agctgagcaa | ggagatcctc | aagattgcaa | atgagcagaa | ccaggtgctg | 300 |
| aatgatgtca | caacaagct | ggacgccatc | aacaccatgc | tgcacatcta | cctgccaaag | 360 |
| atcacctcaa | tgctctctga | tgtgatgaag | cagaactacg | cgctgagcct | ccagattgag | 420 |
| tacctctcaa | agcagctgca | agagatctcc | gacaagctgg | acatcatcaa | tgtcaatgtg | 480 |
| ctcatcaaca | gcaccttgac | agagatcacg | ccggcctacc | agaggatcaa | gtatgtcaat | 540 |
| gagaagttcg | acaagctcac | cttcgccacc | gagagcaccc | tccgcgccaa | gcaaggcatc | 600 |
| ttcaatgaag | attcatttga | caacaacacc | ttggagaact | tgacagacct | cgccgagctg | 660 |
| gccaagagca | tcaccaagaa | tgatgtggac | agcttcgagt | tctacctcca | caccttccat | 720 |
| gatgtgctca | tcggcaacaa | cctctttgga | agaagcgcgc | tcaagacggc | atcagagctc | 780 |
| atcaccaagg | atgagatcaa | gacaagcggc | agcgagatcg | gcaaggtcta | cagcttcctc | 840 |
| atcgtgctga | catcattgca | agccaaggcc | ttcctcaccc | tgcaacctg | ccgcaagttg | 900 |
| ctgggcctct | ccgacatcga | ctacacctcc | atcatgaatg | agcacctcaa | caatgagaag | 960 |

| | |
|---|---|
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca agtgcaagag ctacctcagg | 1560 |
| gagtacctgc tggagagtga tttgaagaac aaggagacag gctgatcgc ccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |
| ctcttcaccc aaggagatgg agagttcagc cagttcatcg gcgacaagct aaagcccaac | 1800 |
| accgactaca tcatccagta caccgtcaag ggcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca gaggaggct acttccgcca aagcctcaac | 2160 |
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagga cttccaccac aatggcttta aggatggctt ctatatcgag | 2340 |
| ctcaccgccg agaggacaag cagcaccttc cacagcttca gagacatcag catcaaggag | 2400 |
| aagattgaa | 2409 |

<210> SEQ ID NO 8
<211> LENGTH: 2409
<212> TYPE: DNA
<213> ORGANISM: Artificial
<220> FEATURE:
<223> OTHER INFORMATION: Axmi115 variant sequence

<400> SEQUENCE: 8

| | |
|---|---|
| atgaacatga caacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg gcaacctcac cttggatgag atcctcaaga accagcagct gctgaatgag | 180 |
| atctcaggca agctggacgg cgtcaatgga agcctcaacg acctcattgc tcaaggcaac | 240 |
| ctcaacaccg agctgagcaa ggagatcctc aagattgcaa atgagcagaa ccaggtgctg | 300 |
| aatgatgtca caacaagct ggacgccatc aacaccatgt gcacatcta cctgccaaag | 360 |
| atcacctcaa tgctctctga tgtgatgaag cagaactacg cgctgagcct ccagattgag | 420 |
| tacctctcaa gcagctgca agagatctcc gacaagctgg acatcatcaa tgtcaatgtg | 480 |
| ctcatcaaca gcaccttgac agagatcacg ccggcctacc agaggatcaa gtatgtcaat | 540 |

| | |
|---|---:|
| gagaagttcg acaagctcac cttcgccacc gagagcaccc tccgcgccaa gcaaggcatc | 600 |
| ttcaatgaag attcatttga caacaacacc ttggagaact tgacagacct cgccgagctg | 660 |
| gccaagagca tcaccaagaa tgatgtggac agcttcgagt tctacctcca caccttccat | 720 |
| gatgtgctca tcggcaacaa cctctttgga agaagcgcgc tcaagacggc atcagagctc | 780 |
| atcaccaagg atgagatcaa gacaagcggc agcgagatcg gcaaggtcta cagcttcctc | 840 |
| atcgtgctga catcattgca agccaaggcc ttcctcacct tgacaacctg ccgcaagttg | 900 |
| ctgggcctct ccgacatcga ctacacctcc atcatgaatg agcacctcaa caatgagaag | 960 |
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca gtgcaagag ctacctcagg | 1560 |
| gagtacctgc tggagagtga tttgaagaac aaggagacag gctgatcgc gccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |
| ctcttcaccc aaggagatgg agagttcagc cagttcatcg gcgacaagct aaagcccaac | 1800 |
| accgactaca tcatccagta caccgtcaag gcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca agaggaggct acttccgcca aagcctcaac | 2160 |
| atcgacagct acagcaccta cgacctcagc ttcagcttca gcggcctctg ggccaaggtg | 2220 |
| attgtgaaga cagccgcgg cgtggtgctc ttcgagaagg tgaagaacaa tggaagcagc | 2280 |
| tatgaggaca tctcagagca cttcaccacc tggggctata aggatggctt ctttatcgag | 2340 |
| ctcaccgccg agaggacaag cagcaccttc cacagcttca gagacatcag catcaaggag | 2400 |
| aagattgaa | 2409 |

<210> SEQ ID NO 9
<211> LENGTH: 2412
<212> TYPE: DNA
<213> ORGANISM: Artificial
<220> FEATURE:
<223> OTHER INFORMATION: Axmi115 variant sequence

<400> SEQUENCE: 9

| | |
|---|---:|
| atgaacatga acaacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg gcgacctcac cttggatgag atcctcaaga accagcagct gctgaatgag | 180 |

-continued

```
atctcaggca agctggacgg cgtcaatgga agcctcaacg acctcattgc tcaaggcaac    240
ctcaacaccg agctgagcaa ggagatcctc aagattgcaa atgagcagaa ccaggtgctg    300
aatgatgtca acaacaagct ggacgccatc aacaccatgc tcaacatcta cctgccaaag    360
atcacctcaa tgctctctga tgtgatgaag cagaactacg cgctgagcct ccagattgag    420
tacctctcaa ggcagctgca agagatctcc gacaagctgg atgtcatcaa cctcaatgtg    480
ctcatcaaca gcaccttgac agagatcacg ccaagctacc agaggatcaa gtatgtcaat    540
gagaagttcg acaagctcac cttcgccacc gagagcaccc tccgcgccaa gcaaggcatc    600
ttcaatgaag attcatttga caacaacacc ttggagaact tgacagacct cgccgagctg    660
gccaagagca tcaccaagaa tgatgtggac agcttcgagt tctacctcca caccttccat    720
gatgtgctca tcggcaacaa cctctttgga agaagcgcgc tcaagacggc atcagagctc    780
atcaccaagg atgagatcaa gacaagcggc agcgagatcg gcaaggtcta cagcttcctc    840
atcgtgctga catcattgca agccaaggcc ttcctcacct tgacaacctg ccgcaagttg    900
ctgggcctct ccgacatcga ctacacctcc atcatgaatg agcacctcaa caatgagaag    960
aatgagttca gagacaacat cctgccggcg ctgagcaaca agttcagcaa cccaagctac   1020
gccaagacca tcggctcaga caactacgcc aaggtgatcc tggagagcga gcctggctac   1080
gcgctggtgg gcttcgagat catcaatgat ccaattcctg ttctcaaggc ctacaaggcc   1140
aagctgaagc agaactacca ggtggacaac cagagcttga gcgagatcgt ctacctggac   1200
atcgacaagc tcttctgccc ggagaactca gagcagaagt actacaccaa gaacctcacc   1260
ttccctgatg gatatgtcat caccaagatc accttcgaga agaagctgaa caacctcatc   1320
tacgaggcca ccgccaactt ctatgatcca tcaacaggag acatcgacct caacaagaag   1380
caagtggaga gcaccttccc tcaaacagac tacatcacca tggacattgg agatgatgat   1440
ggcatctaca tgccgctcgg cgtcatctca gaaaccttct tgacgcccat caacagcttc   1500
ggcctggagg tggacgccaa gagcaagacc ttgacgctca agtgcaagag ctacctcagg   1560
gagtacctgc tggagagtga tttgaagaac aaggagacag gctgatcgc gccgccaaat   1620 gtgttcatca gcaatgtggt gaagaactgg gacatcgagg aggattcatt ggagccatgg   1680
gtggccaaca acaagaatgc ttatgtggac aacaccggcg gcattgaaag aagcaaggcg   1740
ctcttcgtcc aaggagatgg agagttcagc cagttcatcg gcgacaagct aaagcccaac   1800
accgactaca tcatccagta caccgtcaag ggcaagccgg ccatctacct caagaacaag   1860
agcaccggct acatcaccta cgaggacacc aatggaaatt ctgaggagtt ccaaacaatt   1920
gctgtgaagt tcacctcaga aacagatttg agccagaccc acctggtgtt caagagccaa   1980
aatggatatg aagcatgggg agacaacttc atcatcctgg aggccaagct cttcgagaca   2040
ccagaaagcc cggagctcat caagttcaat gattgggaga ggttcggcac cacctacatc   2100
accggcaatg agctgaggat tgatcattca agaggaggct acttccgcca aagcctcaac   2160
atcgacagct acagcaccta cgacctcagc ttcagcttca gcggcctctg ggccaaggtg   2220
attgtgaaga acagccgcgg cgtggtgctc ttcgagaagg tgaagaacaa tggaagcagc   2280
tatgaggaca tctcagagag cttcaccacc gccagcaaca aggatggctt cttcatcgag   2340
ctcaccgccg agaggacaag cagcaccttc cacagcttca gagacatcag catcaaggag   2400
aagattgaat aa                                                       2412
```

<210> SEQ ID NO 10

<211> LENGTH: 2412
<212> TYPE: DNA
<213> ORGANISM: Artificial
<220> FEATURE:
<223> OTHER INFORMATION: Axmi115 variant sequence

<400> SEQUENCE: 10
atgaacatga acaacaccaa gctcaatgca agggcgctgc cgagcttcat cgactacttc 60
aatggcatct atggcttcgc caccggcatc aaggacatca tgaacatgat cttcaagacc 120
gacaccggcg gcgacctcac cttggatgag atcctcaaga accagcagct gctgaatgag 180
atctcaggca agctggacgg cgtcaatgga agcctcaacg acctcattgc tcaaggcaac 240
ctcaacaccg agctgagcaa ggagatcctc aagattgcaa atgagcagaa ccaggtgctg 300
aatgatgtca acaacaagct ggacgccatc aacaccatgc tcaacatcta cctgccaaag 360
atcacctcaa tgctctctga tgtgatgaag cagaactacg cgctgagcct ccagattgag 420
tacctctcaa ggcagctgca agagatctcc gacaagctgg atgtcatcaa cctcaatgtg 480
ctcatcaaca gcaccttgac agagatcacg ccaagctacc agaggatcaa gtatgtcaat 540
gagaagttcg acaagctcac cttcgccacc gagagcaccc tccgcgccaa gcaaggcatc 600
ttcaatgaag attcatttga caacaacacc ttggagaact tgacagacct cgccgagctg 660
gccaagagca tcaccaagaa tgatgtggac agcttcgagt tctacctcca caccttccat 720
gatgtgctca tcggcaacaa cctctttgga agaagcgcgc tcaagacggc atcagagctc 780
atcaccaagg atgagatcaa gacaagcggc agcgagatcg gcaaggtcta cagcttcctc 840
atcgtgctga catcattgca agccaaggcc ttcctcacct tgacaacctg ccgcaagttg 900
ctgggcctct ccgacatcga ctacacctcc atcatgaatg agcacctcaa caatgagaag 960
aatgagttca gagacaacat cctgccggcg ctgagcaaca agttcagcaa cccaagctac 1020
gccaagacca tcggctcaga caactacgcc aaggtgatcc tggagagcga gcctggctac 1080
gcgctggtgg gcttcgagat catcaatgat ccaattcctg ttctcaaggc ctacaaggcc 1140
aagctgaagc agaactacca ggtggacaac cagagcttga gcgagatcgt ctacctggac 1200
atcgacaagc tcttctgccc ggagaactca gagcagaagt actacaccaa gaacctcacc 1260
ttccctgatg gatatgtcat caccaagatc accttcgaga agaagctgaa caacctcatc 1320
tacgaggcca ccgccaactt ctatgatcca tcaacaggag acatcgacct caacaagaag 1380
caagtggaga gcaccttccc tcaaacagac tacatcacca tggacattgg agatgatgat 1440
ggcatctaca tgccgctcgg cgtcatctca gaaaccttct tgacgcccat caacagcttc 1500
ggcctggagg tggacgccaa gagcaagacc ttgacgctca agtgcaagag ctacctcagg 1560
gagtacctgc tggagagtga tttgaagaac aaggagacag ggctgatcgc gccgccaaat 1620
gtgttcatca gcaatgtggt gaagaactgg gacatcgagg aggattcatt ggagccatgg 1680
gtggccaaca acaagaatgc ttatgtggac aacaccggcg gcattgaaag aagcaaggcg 1740
ctcttcaccc ttggagatgg agagttcagc cagttcatcg gcgacaagct aaagcccaac 1800
accgactaca tcatccagta caccgtcaag ggcaagccgg ccatctacct caagaacaag 1860
agcaccggct acatcaccta cgaggacacc aatggaaatt ctgaggagtt ccaaacaatt 1920
gctgtgaagt tcacctcaga aacagatttg agccagaccc acctggtgtt caagagccaa 1980
aatggatatg aagcatgggg agacaacttc atcatcctgg aggccaagct cttcgagaca 2040
ccagaaagcc cggagctcat caagttcaat gattgggaga ggttcggcac cacctacatc 2100
accggcaatg agctgaggat tgatcattca agaggaggct acttccgcca aagcctcaac 2160

-continued

| | |
|---|---|
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc acagcttca gagacatcag catcaaggag | 2400 |
| aagattgaat aa | 2412 |

<210> SEQ ID NO 11  
<211> LENGTH: 2412  
<212> TYPE: DNA  
<213> ORGANISM: Artificial  
<220> FEATURE:  
<223> OTHER INFORMATION: Axmi115 variant sequence

<400> SEQUENCE: 11

| | |
|---|---|
| atgaacatga caacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg gcgacctcac cttggatgag atcctcaaga accagcagct gctgaatgag | 180 |
| atctcaggca gctggacgg cgtcaatgga agcctcaacg acctcattgc tcaaggcaac | 240 |
| ctcaacaccg agctgagcaa ggagatcctc aagattgcaa atgagcagaa ccaggtgctg | 300 |
| aatgatgtca caacaagct ggacgccatc aacaccatgc tcaacatcta cctgccaaag | 360 |
| atcacctcaa tgctctctga tgtgatgaag cagaactacg cgctgagcct ccagattgag | 420 |
| tacctctcaa ggcagctgca agagatctcc gacaagctgg atgtcatcaa cctcaatgtg | 480 |
| ctcatcaaca gcaccttgac agagatcacg ccaagctacc agaggatcaa gtatgtcaat | 540 |
| gagaagttcg acaagctcac cttcgccacc gagagcaccc tccgcgccaa gcaaggcatc | 600 |
| ttcaatgaag attcatttga caacaacacc ttggagaact tgacagacct cgccgagctg | 660 |
| gccaagagca tcaccaagaa tgatgtggac agcttcgagt tctacctcca caccttccat | 720 |
| gatgtgctca tcggcaacaa cctctttgga agaagcgcgc tcaagacggc atcagagctc | 780 |
| atcaccaagg atgagatcaa gacaagcggc agcgagatcg gcaaggtcta cagcttcctc | 840 |
| atcgtgctga catcattgca agccaaggcc ttcctcacct tgacaacctg ccgcaagttg | 900 |
| ctgggcctct ccgacatcga ctacacctca atcatgaatg agcacctcaa caatgagaag | 960 |
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaaccctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca gtgcaagag ctacctcagg | 1560 |
| gagtacctgc tggagagtga tttgaagaac aaggagacag gctgatcgc gccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |

| | |
|---|---|
| ctcttcacca aaggagatgg agagttcagc cagttcatcg gcgacaagct aaagcccaac | 1800 |
| accgactaca tcatccagta caccgtcaag ggcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca agaggaggct acttccgcca aagcctcaac | 2160 |
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc cacagcttca gagacatcag catcaaggag | 2400 |
| aagattgaat aa | 2412 |

<210> SEQ ID NO 12
<211> LENGTH: 2412
<212> TYPE: DNA
<213> ORGANISM: Artificial
<220> FEATURE:
<223> OTHER INFORMATION: Axmi115 variant sequence

<400> SEQUENCE: 12

| | |
|---|---|
| atgaacatga acaacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg gcgacctcac cttggatgag atcctcaaga ccagcagct gctgaatgag | 180 |
| atctcaggca gctggacgg cgtcaatgga agcctcaacg acctcattgc tcaaggcaac | 240 |
| ctcaacaccg agctgagcaa ggagatcctc aagattgcaa atgagcagaa ccaggtgctg | 300 |
| aatgatgtca caacaagct ggacgccatc aacaccatgc tcaacatcta cctgccaaag | 360 |
| atcacctcaa tgctctctga tgtgatgaag cagaactacg cgctgagcct ccagattgag | 420 |
| tacctctcaa ggcagctgca agagatctcc gacaagctgg atgtcatcaa cctcaatgtg | 480 |
| ctcatcaaca gcaccttgac agagatcacg ccaagctacc agaggatcaa gtatgtcaat | 540 |
| gagaagttcg acaagctcac cttcgccacc gagagcaccc tccgcgccaa gcaaggcatc | 600 |
| ttcaatgaag attcatttga caacaacacc ttggagaact tgacagacct cgccgagctg | 660 |
| gccaagagca tcaccaagaa tgatgtggac agcttcgagt tctacctcca caccttccat | 720 |
| gatgtgctca tcggcaacaa cctctttgga agaagcgcgc tcaagacggc atcagagctc | 780 |
| atcaccaagg atgagatcaa gacaagcggc agcgagatcg gcaaggtcta cagcttcctc | 840 |
| atcgtgctga catcattgca agccaaggcc ttcctcacct tgacaacctg ccgcaagttg | 900 |
| ctgggcctct ccgacatcga ctacacctcc atcatgaatg agcacctcaa caatgagaag | 960 |
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |

```
caagtggaga gcaccttccc tcaaacagac tacatcacca tggacattgg agatgatgat    1440
ggcatctaca tgccgctcgg cgtcatctca gaaaccttct tgacgcccat caacagcttc    1500
ggcctggagg tggacgccaa gagcaagacc ttgacgctca agtgcaagag ctacctcagg    1560
gagtacctgc tggagagtga tttgaagaac aaggagacag gctgatcgc gccgccaaat    1620 gtgttcatca gcaatgtggt gaagaactgg gacatcgagg aggattcatt ggagccatgg    1680
gtggccaaca caagaatgc ttatgtggac aacaccggcg gcattgaaag aagcaaggcg    1740
ctcttcaccc aaagtgatgg agagttcagc cagttcatcg gcgacaagct aaagcccaac    1800
accgactaca tcatccagta caccgtcaag ggcaagccgg ccatctacct caagaacaag    1860
agcaccggct acatcaccta cgaggacacc aatggaaatt ctgaggagtt ccaaacaatt    1920
gctgtgaagt tcacctcaga aacagatttg agccagaccc acctggtgtt caagagccaa    1980
aatggatatg aagcatgggg agacaacttc atcatcctgg aggccaagct cttcgagaca    2040
ccagaaagcc cggagctcat caagttcaat gattgggaga ggttcggcac cacctacatc    2100
accggcaatg agctgaggat tgatcattca agaggaggct acttccgcca aagcctcaac    2160
atcgacagct acagcaccta cgacctcagc ttcagcttca gcggcctctg gccaaggtg    2220 attgtgaaga cagccgcgg cgtggtgctc ttcgagaagg tgaagaacaa tggaagcagc    2280
tatgaggaca tctcagagag cttcaccacc gccagcaaca aggatggctt cttcatcgag    2340
ctcaccgccg agaggacaag cagcaccttc cacagcttca gagacatcag catcaaggag    2400
aagattgaat aa                                                        2412

<210> SEQ ID NO 13
<211> LENGTH: 2412
<212> TYPE: DNA
<213> ORGANISM: Artificial sequence
<220> FEATURE:
<223> OTHER INFORMATION: Axmi115 variant sequence

<400> SEQUENCE: 13
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg cgacctcac cttggatgag atcctcaaga accagcagct gctgaatgag     180
atctcaggca agctggacgg cgtcaatgga agcctcaacg acctcattgc tcaaggcaac     240
ctcaacaccg agctgagcaa ggagatcctc aagattgcaa atgagcagaa ccaggtgctg     300
aatgatgtca caacaagct ggacgccatc aacaccatgc tcaacatcta cctgccaaag     360
atcacctcaa tgctctctga tgtgatgaag cagaactacg cgctgagcct ccagattgag     420
tacctctcaa ggcagctgca agatctccc gacaagctgg atgtcatcaa cctcaatgtg     480
ctcatcaaca gcaccttgac agagatcacg ccaagctacc agaggatcaa gtatgtcaat     540
gagaagttcg acaagctcac cttcgccacc gagagcaccc tccgcgccaa gcaaggcatc     600
ttcaatgaag attcatttga caacaacacc ttggagaact tgacagacct cgccgagctg     660
gccaagagca tcaccaagaa tgatgtggac agcttcgagt tctacctcca caccttccat     720
gatgtgctca tcggcaacaa cctctttgga gaagcgcgc tcaagacggc atcagagctc     780
atcaccaagg atgagatcaa gacaagcggc agcgagatcg gcaaggtcta cagcttcctc     840
atcgtgctga catcattgca agccaaggcc ttcctcaccct tgcaaccctg ccgcaagttg     900
ctgggcctct ccgacatcga ctacacctcc atcatgaatg agcacctcaa caatgagaag     960
```

| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca agtgcaagag ctacctcagg | 1560 |
| gagtacctgc tggagagtga tttgaagaac aaggagacag gctgatcgc gccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |
| ctcttcaccc aaggagatgg agttttcagc cagttcatcg gcgacaagct aaagcccaac | 1800 |
| accgactaca tcatccagta caccgtcaag ggcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca agaggaggct acttccgcca aagcctcaac | 2160 |
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc cacagcttca gagacatcag catcaaggag | 2400 |
| aagattgaat aa | 2412 |

<210> SEQ ID NO 14
<211> LENGTH: 2412
<212> TYPE: DNA
<213> ORGANISM: Artificial sequence
<220> FEATURE:
<223> OTHER INFORMATION: Axmi115 variant sequence

<400> SEQUENCE: 14

| atgaacatga caacaccaa gctcaatgca agggcgctgc cgagcttcat cgactacttc | 60 |
| aatggcatct atggcttcgc caccggcatc aaggacatca tgaacatgat cttcaagacc | 120 |
| gacaccggcg cgacctcac cttggatgag atcctcaaga ccagcagct gctgaatgag | 180 |
| atctcaggca agctggacgg cgtcaatgga agcctcaacg acctcattgc tcaaggcaac | 240 |
| ctcaacaccg agctgagcaa ggagatcctc aagattgcaa atgagcagaa ccaggtgctg | 300 |
| aatgatgtca caacaagct ggacgccatc aacaccatgc tcaacatcta cctgccaaag | 360 |
| atcacctcaa tgctctctga tgtgatgaag cagaactacg cgctgagcct ccagattgag | 420 |
| tacctctcaa ggcagctgca agagatctcc gacaagctgg atgtcatcaa cctcaatgtg | 480 |
| ctcatcaaca gcaccttgac agagatcacg ccaagctacc agaggatcaa gtatgtcaat | 540 |
| gagaagttcg acaagctcac cttcgccacc gagagcaccc tccgcgccaa gcaaggcatc | 600 |

```
ttcaatgaag attcatttga caacaacacc ttgagaaact tgacagacct cgccgagctg      660
gccaagagca tcaccaagaa tgatgtggac agcttcgagt tctacctcca caccttccat      720
gatgtgctca tcggcaacaa cctctttgga agaagcgcgc tcaagacggc atcagagctc      780
atcaccaagg atgagatcaa gacaagcggc agcgagatcg gcaaggtcta cagcttcctc      840
atcgtgctga catcattgca agccaaggcc ttcctcacct tgacaacctg ccgcaagttg      900
ctgggcctct ccgacatcga ctacacctcc atcatgaatg agcacctcaa caatgagaag      960
aatgagttca gagacaacat cctgccggcg ctgagcaaca gttcagcaa cccaagctac      1020
gccaagacca tcggctcaga caactacgcc aaggtgatcc tggagagcga gcctggctac      1080
gcgctggtgg gcttcgagat catcaatgat ccaattcctg ttctcaaggc ctacaaggcc      1140
aagctgaagc agaactacca ggtggacaac cagagcttga gcgagatcgt ctacctggac      1200
atcgacaagc tcttctgccc ggagaactca gagcagaagt actacaccaa gaacctcacc      1260
ttccctgatg gatatgtcat caccaagatc accttcgaga agaagctgaa caacctcatc      1320
tacgaggcca ccgccaactt ctatgatcca tcaacaggag acatcgacct caacaagaag      1380
caagtggaga gcaccttccc tcaaacagac tacatcacca tggacattgg agatgatgat      1440
ggcatctaca tgccgctcgg cgtcatctca gaaaccttct tgacgcccat caacagcttc      1500
ggcctggagg tggacgccaa gagcaagacc ttgacgctca gtgcaagag ctacctcagg      1560
gagtacctgc tggagagtga tttgaagaac aaggagacag ggctgatcgc gccgccaaat      1620
gtgttcatca gcaatgtggt gaagaactgg gacatcgagg aggattcatt ggagccatgg      1680
gtggccaaca acaagaatgc ttatgtggac aacaccggcg gcattgaaag aagcaaggcg      1740
ctcttcaccc aaggagatgg agagttcagc cagttcatcg gcgacaagct aaagcccaac      1800
accgactaca tcatccagta caccgtcaag ggcaagccgg ccatctacct caagaacaag      1860
agcaccggct acatcaccta cgaggacacc aatggaaatt ctgaggagtt ccaaacaatt      1920
gctgtgaagt tcacctcaga aacagatttg agccagaccc acctggtgtt caagagccaa      1980
aatggatatg aagcatgggg agacaacttc atcatcctgg aggccaagct cttcgagaca      2040
ccagaaagcc cggagctcat caagttcaat gattgggaga ggttcggcac cacctacatc      2100
accggcaatg agctgaggat tgatcattca agaggaggct acttccgcca agcctcaac      2160
atcgacagct acagcaccta cgacctcagc ttcagcttca gcggcctctg gccaaggtg      2220
attgtgaaga acagccgcgg cgtggtgctc ttcgagaagg tgaagaacaa tggaagcagc      2280
tatgaggaca tctcagagag cttcaccacc tgcagcaaca aggatggctt cttcatcgag      2340
ctcaccgccg agaggacaag cagcaccttc cacagcttca gagacatcag catcaaggag      2400
aagattgaat aa                                                          2412
```

<210> SEQ ID NO 15
<211> LENGTH: 803
<212> TYPE: PRT
<213> ORGANISM: Artificial sequence
<220> FEATURE:
<223> OTHER INFORMATION: AXMI115 variant sequence

<400> SEQUENCE: 15

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

-continued

```
Ile Met Asn Met Ile Phe Lys Thr Asp Thr Gly Gly Asn Leu Thr Leu
        35                  40                  45
Asp Glu Ile Leu Lys Asn Gln Gln Leu Leu Asn Glu Ile Ser Gly Lys
 50                  55                  60
Leu Asp Gly Val Asn Gly Ser Leu Asn Asp Leu Ile Ala Gln Gly Asn
 65                  70                  75                  80
Leu Asn Thr Glu Leu Ser Lys Glu Ile Leu Lys Ile Ala Asn Glu Gln
                 85                  90                  95
Asn Gln Val Leu Asn Asp Val Asn Asn Lys Leu Asp Ala Ile Asn Thr
            100                 105                 110
Met Leu His Ile Tyr Leu Pro Lys Ile Thr Ser Met Leu Ser Asp Val
            115                 120                 125
Met Lys Gln Asn Tyr Ala Leu Ser Leu Gln Ile Glu Tyr Leu Ser Lys
    130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Asp Lys Leu Thr Phe Ala Thr Glu Ser
            180                 185                 190
Thr Leu Arg Ala Lys Gln Gly Ile Phe Asn Glu Asp Ser Phe Asp Asn
        195                 200                 205
Asn Thr Leu Glu Asn Leu Thr Asp Leu Ala Glu Leu Ala Lys Ser Ile
            210                 215                 220
Thr Lys Asn Asp Val Asp Ser Phe Glu Phe Tyr Leu His Thr Phe His
225                 230                 235                 240
Asp Val Leu Ile Gly Asn Asn Leu Phe Gly Arg Ser Ala Leu Lys Thr
                245                 250                 255
Ala Ser Glu Leu Ile Thr Lys Asp Glu Ile Lys Thr Ser Gly Ser Glu
            260                 265                 270
Ile Gly Lys Val Tyr Ser Phe Leu Ile Val Leu Thr Ser Leu Gln Ala
        275                 280                 285
Lys Ala Phe Leu Thr Leu Thr Thr Cys Arg Lys Leu Leu Gly Leu Ser
    290                 295                 300
Asp Ile Asp Tyr Thr Ser Ile Met Asn Glu His Leu Asn Asn Glu Lys
305                 310                 315                 320
Asn Glu Phe Arg Asp Asn Ile Leu Pro Ala Leu Ser Asn Lys Phe Ser
                325                 330                 335
Asn Pro Ser Tyr Ala Lys Thr Ile Gly Ser Asp Asn Tyr Ala Lys Val
            340                 345                 350
Ile Leu Glu Ser Glu Pro Gly Tyr Ala Leu Val Gly Phe Glu Ile Ile
        355                 360                 365
Asn Asp Pro Ile Pro Val Leu Lys Ala Tyr Lys Ala Lys Leu Lys Gln
    370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
            420                 425                 430
Glu Lys Lys Leu Asn Asn Leu Ile Tyr Glu Ala Thr Ala Asn Phe Tyr
        435                 440                 445
Asp Pro Ser Thr Gly Asp Ile Asp Leu Asn Lys Lys Gln Val Glu Ser
```

```
            450                 455                 460
Thr Phe Pro Gln Thr Asp Tyr Ile Thr Met Asp Ile Gly Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Glu Phe Ser Gln Phe
                580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
            610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
                660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
            690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
                740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 16
<211> LENGTH: 798
<212> TYPE: PRT
<213> ORGANISM: Artificial sequence
<220> FEATURE:
<223> OTHER INFORMATION: AXMI115 variant sequence

<400> SEQUENCE: 16

Met Asn Met Asn Asn Thr Lys Leu Asn Ala Arg Ala Leu Pro Ser Phe
1               5                   10                  15
```

-continued

```
Ile Asp Tyr Phe Asn Gly Ile Tyr Gly Phe Ala Thr Gly Ile Lys Asp
         20                  25                  30
Ile Met Asn Met Ile Phe Lys Thr Asp Thr Gly Gly Asn Leu Thr Leu
         35                  40                  45
Asp Glu Ile Leu Lys Asn Gln Gln Leu Leu Asn Glu Ile Ser Gly Lys
 50                  55                  60
Leu Asp Gly Val Asn Gly Ser Leu Asn Asp Leu Ile Ala Gln Gly Asn
 65                  70                  75                  80
Leu Asn Thr Glu Leu Ser Lys Glu Ile Leu Lys Ile Ala Asn Glu Gln
                 85                  90                  95
Asn Gln Val Leu Asn Asp Val Asn Asn Lys Leu Asp Ala Ile Asn Thr
            100                 105                 110
Met Leu His Ile Tyr Leu Pro Lys Ile Thr Ser Met Leu Ser Asp Val
            115                 120                 125
Met Lys Gln Asn Tyr Ala Leu Ser Leu Gln Ile Glu Tyr Leu Ser Lys
130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Glu Glu Leu Thr Phe Ala Thr Glu Thr
            180                 185                 190
Thr Leu Lys Val Lys Lys Asp Ser Ser Pro Ala Asp Ile Leu Asp Glu
            195                 200                 205
Leu Thr Glu Leu Thr Glu Leu Ala Lys Ser Val Thr Lys Asn Asp Val
210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                245                 250                 255
Ala Lys Glu Asn Val Lys Thr Ser Gly Ser Glu Val Gly Asn Val Tyr
            260                 265                 270
Asn Phe Leu Ile Val Leu Thr Ala Leu Gln Ala Lys Ala Phe Leu Thr
            275                 280                 285
Leu Thr Thr Cys Arg Lys Leu Leu Gly Leu Ser Asp Ile Asp Tyr Thr
290                 295                 300
Ser Ile Met Asn Glu His Leu Asn Asn Glu Lys Asn Glu Phe Arg Asp
305                 310                 315                 320
Asn Ile Leu Pro Ala Leu Ser Asn Lys Phe Ser Asn Pro Ser Tyr Ala
                325                 330                 335
Lys Thr Ile Gly Ser Asp Asn Tyr Ala Lys Val Ile Leu Glu Ser Glu
            340                 345                 350
Pro Gly Tyr Ala Leu Val Gly Phe Glu Ile Ile Asn Asp Pro Ile Pro
            355                 360                 365
Val Leu Lys Ala Tyr Lys Ala Lys Leu Lys Gln Asn Tyr Gln Val Asp
            370                 375                 380
Asn Gln Ser Leu Ser Glu Ile Val Tyr Leu Asp Ile Asp Lys Leu Phe
385                 390                 395                 400
Cys Pro Glu Asn Ser Glu Gln Lys Tyr Tyr Thr Lys Asn Leu Thr Phe
                405                 410                 415
Pro Asp Gly Tyr Val Ile Thr Lys Ile Thr Phe Glu Lys Lys Leu Asn
            420                 425                 430
```

```
Asn Leu Ile Tyr Glu Ala Thr Ala Asn Phe Tyr Asp Pro Ser Thr Gly
            435                 440                 445

Asp Ile Asp Leu Asn Lys Lys Gln Val Glu Ser Thr Phe Pro Gln Thr
450                 455                 460

Asp Tyr Ile Thr Met Asp Ile Gly Asp Asp Gly Ile Tyr Met Pro
465                 470                 475                 480

Leu Gly Val Ile Ser Glu Thr Phe Leu Thr Pro Ile Asn Ser Phe Gly
                485                 490                 495

Leu Glu Val Asp Ala Lys Ser Lys Thr Leu Thr Lys Cys Lys Ser
            500                 505                 510

Tyr Leu Arg Glu Tyr Leu Leu Glu Ser Asp Leu Lys Asn Lys Glu Thr
            515                 520                 525

Gly Leu Ile Ala Pro Pro Asn Val Phe Ile Ser Asn Val Val Lys Asn
530                 535                 540

Trp Asp Ile Glu Glu Asp Ser Leu Glu Pro Trp Val Ala Asn Asn Lys
545                 550                 555                 560

Asn Ala Tyr Val Asp Asn Thr Gly Gly Ile Glu Arg Ser Lys Ala Leu
                565                 570                 575

Phe Thr Gln Gly Asp Gly Glu Phe Ser Gln Phe Ile Gly Asp Lys Leu
            580                 585                 590

Lys Pro Asn Thr Asp Tyr Ile Ile Gln Tyr Thr Val Lys Gly Lys Pro
            595                 600                 605

Ala Ile Tyr Leu Lys Asn Lys Ser Thr Gly Tyr Ile Thr Tyr Glu Asp
            610                 615                 620

Thr Asn Gly Asn Ser Glu Glu Phe Gln Thr Ile Ala Val Lys Phe Thr
625                 630                 635                 640

Ser Glu Thr Asp Leu Ser Gln Thr His Leu Val Phe Lys Ser Gln Asn
            645                 650                 655

Gly Tyr Glu Ala Trp Gly Asp Asn Phe Ile Ile Leu Glu Ala Lys Leu
            660                 665                 670

Phe Glu Thr Pro Glu Ser Pro Glu Leu Ile Lys Phe Asn Asp Trp Glu
            675                 680                 685

Arg Phe Gly Thr Thr Tyr Ile Thr Gly Asn Glu Leu Arg Ile Asp His
690                 695                 700

Ser Arg Gly Gly Tyr Phe Arg Gln Ser Leu Asn Ile Asp Ser Tyr Ser
705                 710                 715                 720

Thr Tyr Asp Leu Ser Phe Ser Phe Ser Gly Leu Trp Ala Lys Val Ile
                725                 730                 735

Val Lys Asn Ser Arg Gly Val Val Leu Phe Lys Val Lys Asn Asn
            740                 745                 750

Gly Ser Ser Tyr Glu Asp Ile Ser Glu Ser Phe Thr Thr Ala Ser Asn
            755                 760                 765

Lys Asp Gly Phe Phe Ile Glu Leu Thr Ala Glu Arg Thr Ser Ser Thr
770                 775                 780

Phe His Ser Phe Arg Asp Ile Ser Ile Lys Glu Lys Ile Glu
785                 790                 795

<210> SEQ ID NO 17
<211> LENGTH: 795
<212> TYPE: PRT
<213> ORGANISM: Artificial sequence
<220> FEATURE:
<223> OTHER INFORMATION: AXMI115 variant sequence

<400> SEQUENCE: 17
```

```
Met Asn Met Asn Asn Thr Lys Leu Asn Ala Arg Ala Leu Pro Ser Phe
 1               5                  10                  15
Ile Asp Tyr Phe Asn Gly Ile Tyr Gly Phe Ala Thr Gly Ile Lys Asp
             20                  25                  30
Ile Met Asn Met Ile Phe Lys Thr Asp Thr Gly Gly Asn Leu Thr Leu
         35                  40                  45
Asp Glu Ile Leu Lys Asn Gln Gln Leu Leu Asn Glu Ile Ser Gly Lys
     50                  55                  60
Leu Asp Gly Val Asn Gly Ser Leu Asn Asp Leu Ile Ala Gln Gly Asn
 65                  70                  75                  80
Leu Asn Thr Glu Leu Ser Lys Glu Ile Leu Lys Ile Ala Asn Glu Gln
                 85                  90                  95
Asn Gln Val Leu Asn Asp Val Asn Asn Lys Leu Asp Ala Ile Asn Thr
             100                 105                 110
Met Leu His Ile Tyr Leu Pro Lys Ile Thr Ser Met Leu Ser Asp Val
         115                 120                 125
Met Lys Gln Asn Tyr Ala Leu Ser Leu Gln Ile Glu Tyr Leu Ser Lys
     130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                 165                 170                 175
Lys Tyr Val Asn Glu Lys Phe Glu Glu Leu Thr Phe Ala Thr Glu Thr
             180                 185                 190
Thr Leu Lys Val Lys Lys Asp Ser Ser Pro Ala Asp Ile Leu Asp Glu
         195                 200                 205
Leu Thr Glu Leu Thr Glu Leu Ala Lys Ser Val Thr Lys Asn Asp Val
     210                 215                 220
Asp Gly Phe Glu Phe Tyr Leu Asn Thr Phe His Asp Val Met Val Gly
225                 230                 235                 240
Asn Asn Leu Phe Gly Arg Ser Ala Leu Lys Thr Ala Ser Glu Leu Ile
                 245                 250                 255
Ala Lys Glu Asn Val Lys Thr Ser Gly Ser Glu Val Gly Asn Val Tyr
             260                 265                 270
Asn Phe Leu Ile Val Leu Thr Ala Leu Gln Ala Lys Ala Phe Leu Thr
         275                 280                 285
Leu Thr Thr Cys Arg Lys Leu Leu Gly Leu Ala Asp Ile Asp Tyr Thr
     290                 295                 300
Ser Ile Met Asn Glu His Leu Asn Lys Glu Lys Glu Glu Phe Arg Val
305                 310                 315                 320
Asn Ile Leu Pro Thr Leu Ser Asn Thr Phe Ser Asn Pro Asn Tyr Ala
                 325                 330                 335
Lys Val Lys Gly Ser Asp Glu Asp Ala Lys Met Ile Val Glu Ala Lys
             340                 345                 350
Pro Gly His Ala Leu Val Gly Phe Glu Met Ser Asn Asp Ser Ile Thr
         355                 360                 365
Val Leu Lys Val Tyr Glu Ala Lys Leu Lys Gln Asn Tyr Gln Val Asp
     370                 375                 380
Lys Asp Ser Leu Ser Glu Val Ile Tyr Gly Asp Met Asp Lys Leu Leu
385                 390                 395                 400
Cys Pro Asp Gln Ser Glu Gln Ile Tyr Tyr Thr Asn Asn Ile Val Phe
                 405                 410                 415
Pro Asn Glu Tyr Val Ile Thr Lys Ile Asp Phe Thr Lys Lys Met Lys
```

420                 425                 430
Thr Leu Arg Tyr Glu Val Thr Ala Asn Ser Tyr Asp Ser Ser Thr Gly
            435                 440                 445

Glu Ile Asp Leu Asn Lys Lys Val Glu Ser Ser Glu Ala Glu Tyr
450                 455                 460

Arg Thr Leu Ser Ala Lys Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Asn Leu
            530                 535                 540

Glu Gly Glu Asn Leu Glu Pro Trp Ile Ala Asn Asn Lys Asn Ala Tyr
545                 550                 555                 560

Val Asp His Thr Gly Gly Val Asn Gly Thr Arg Ala Leu Tyr Val His
                565                 570                 575

Lys Asp Gly Gly Phe Ser Gln Phe Ile Gly Asp Lys Leu Lys Pro Lys
            580                 585                 590

Thr Glu Tyr Val Ile Gln Tyr Thr Val Lys Gly Lys Pro Ala Ile Tyr
            595                 600                 605

Leu Lys Asn Lys Ser Thr Gly Tyr Ile Thr Tyr Glu Asp Thr Asn Gly
            610                 615                 620

Asn Ser Glu Glu Phe Gln Thr Ile Ala Val Lys Phe Thr Ser Glu Thr
625                 630                 635                 640

Asp Leu Ser Gln Thr His Leu Val Phe Lys Ser Gln Asn Gly Tyr Glu
                645                 650                 655

Ala Trp Gly Asp Asn Phe Ile Ile Leu Glu Ala Lys Leu Phe Glu Thr
            660                 665                 670

Pro Glu Ser Pro Glu Leu Ile Lys Phe Asn Asp Trp Glu Arg Phe Gly
            675                 680                 685

Thr Thr Tyr Ile Thr Gly Asn Glu Leu Arg Ile Asp His Ser Arg Gly
            690                 695                 700

Gly Tyr Phe Arg Gln Ser Leu Asn Ile Asp Ser Tyr Ser Thr Tyr Asp
705                 710                 715                 720

Leu Ser Phe Ser Phe Ser Gly Leu Trp Ala Lys Val Ile Val Lys Asn
                725                 730                 735

Ser Arg Gly Val Val Leu Phe Glu Lys Val Lys Asn Asn Gly Ser Ser
            740                 745                 750

Tyr Glu Asp Ile Ser Glu Ser Phe Thr Thr Ala Ser Asn Lys Asp Gly
            755                 760                 765

Phe Phe Ile Glu Leu Thr Ala Glu Arg Thr Ser Ser Thr Phe His Ser
            770                 775                 780

Phe Arg Asp Ile Ser Ile Lys Glu Lys Ile Glu
785                 790                 795

<210> SEQ ID NO 18
<211> LENGTH: 803
<212> TYPE: PRT
<213> ORGANISM: Artificial sequence
<220> FEATURE:
<223> OTHER INFORMATION: AXMI115 variant sequence

```
<400> SEQUENCE: 18

Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
                35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
            195                 200                 205

Asn Thr Leu Glu Asn Leu Thr Asp Leu Ala Glu Leu Ala Lys Ser Ile
            210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
            290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
            325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
            370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415
```

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
    450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
    530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Lys Phe Ser Gln Phe
            580                 585                 590

Ile Gly Asp Lys Leu Lys Pro Asn Thr Asp Tyr Ile Ile Gln Tyr Thr
        595                 600                 605

Val Lys Gly Lys Pro Ala Ile Tyr Leu Lys Asn Lys Ser Thr Gly Tyr
    610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
        675                 680                 685

Phe Asn Asp Trp Glu Arg Phe Gly Thr Thr Tyr Ile Thr Gly Asn Glu
    690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
        755                 760                 765

Thr Thr Ala Ser Asn Lys Asp Gly Phe Phe Ile Glu Leu Thr Ala Glu
    770                 775                 780

Arg Thr Ser Ser Thr Phe His Ser Phe Arg Asp Ile Ser Ile Lys Glu
785                 790                 795                 800

Lys Ile Glu

<210> SEQ ID NO 19
<211> LENGTH: 803
<212> TYPE: PRT

<213> ORGANISM: Artificial
<220> FEATURE:
<223> OTHER INFORMATION: AXMI115 variant sequence

<400> SEQUENCE: 19

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
    370                 375                 380

Asn Tyr Gln Val Asp Asn Gln Ser Leu Ser Glu Ile Val Tyr Leu Asp
```

```
385                 390                 395                 400
Ile Asp Lys Leu Phe Cys Pro Glu Asn Ser Glu Gln Lys Tyr Tyr Thr
                    405                 410                 415
Lys Asn Leu Thr Phe Pro Asp Gly Tyr Val Ile Thr Lys Ile Thr Phe
                    420                 425                 430
Glu Lys Lys Leu Asn Asn Leu Ile Tyr Glu Ala Thr Ala Asn Phe Tyr
                    435                 440                 445
Asp Pro Ser Thr Gly Asp Ile Asp Leu Asn Lys Lys Gln Val Glu Ser
                    450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                    485                 490                 495
Ile Asn Ser Phe Gly Leu Glu Val Asp Ala Lys Ser Lys Thr Leu Thr
                    500                 505                 510
Leu Lys Cys Lys Ser Tyr Leu Arg Glu Tyr Leu Leu Glu Ser Asp Leu
                    515                 520                 525
Lys Asn Lys Glu Thr Gly Leu Ile Ala Pro Pro Asn Val Phe Ile Ser
                    530                 535                 540
Asn Val Val Lys Asn Trp Asp Ile Glu Glu Asp Ser Leu Glu Pro Trp
545                 550                 555                 560
Val Ala Asn Asn Lys Asn Ala Tyr Val Asp Asn Thr Gly Gly Ile Glu
                    565                 570                 575
Arg Ser Lys Ala Leu Phe Thr Gln Gly Asp Gly Glu Phe Ser Gln Phe
                    580                 585                 590
Ile Gly Asp Lys Leu Lys Pro Asn Thr Asp Tyr Ile Ile Gln Tyr Thr
                    595                 600                 605
Val Lys Gly Lys Pro Ala Ile Tyr Leu Lys Asn Lys Ser Thr Gly Tyr
                    610                 615                 620
Ile Thr Tyr Glu Asp Thr Asn Gly Asn Ser Glu Glu Phe Gln Thr Ile
625                 630                 635                 640
Ala Val Lys Phe Thr Ser Glu Thr Asp Leu Ser Gln Thr His Leu Val
                    645                 650                 655
Phe Lys Ser Gln Asn Gly Tyr Glu Ala Trp Gly Asp Asn Phe Ile Ile
                    660                 665                 670
Leu Glu Ala Lys Leu Phe Glu Thr Pro Glu Ser Pro Glu Leu Ile Lys
                    675                 680                 685
Phe Asn Asp Trp Glu Arg Phe Gly Thr Thr Tyr Ile Thr Gly Asn Glu
                    690                 695                 700
Leu Arg Ile Asp His Ser Arg Gly Gly Tyr Phe Arg Gln Ser Leu Asn
705                 710                 715                 720
Ile Asp Ser Tyr Ser Thr Tyr Asp Leu Ser Phe Ser Phe Ser Gly Leu
                    725                 730                 735
Trp Ala Lys Val Ile Val Lys Asn Ser Arg Gly Val Val Leu Phe Glu
                    740                 745                 750
Lys Val Lys Asn Asn Gly Ser Ser Tyr Glu Asp Ile Ser Glu Ser Phe
                    755                 760                 765
Thr Thr Met Ser Asn Lys Asp Gly Phe Phe Ile Glu Leu Thr Ala Glu
                    770                 775                 780
Arg Thr Ser Ser Thr Phe His Ser Phe Arg Asp Ile Ser Ile Lys Glu
785                 790                 795                 800
Lys Ile Glu
```

<210> SEQ ID NO 20
<211> LENGTH: 803
<212> TYPE: PRT
<213> ORGANISM: Artificial
<220> FEATURE:
<223> OTHER INFORMATION: AXMI115 variant sequence

<400> SEQUENCE: 20

```
Met Asn Met Asn Thr Lys Leu Asn Ala Arg Ala Leu Pro Ser Phe
1               5                  10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65              70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365
```

-continued

```
Asn Asp Pro Ile Pro Val Leu Lys Ala Tyr Lys Ala Lys Leu Lys Gln
    370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
                420                 425                 430
Glu Lys Lys Leu Asn Asn Leu Ile Tyr Glu Ala Thr Ala Asn Phe Tyr
            435                 440                 445
Asp Pro Ser Thr Gly Asp Ile Asp Leu Asn Lys Lys Gln Val Glu Ser
450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                485                 490                 495
Ile Asn Ser Phe Gly Leu Glu Val Asp Ala Lys Ser Lys Thr Leu Thr
                500                 505                 510
Leu Lys Cys Lys Ser Tyr Leu Arg Glu Tyr Leu Leu Glu Ser Asp Leu
            515                 520                 525
Lys Asn Lys Glu Thr Gly Leu Ile Ala Pro Pro Asn Val Phe Ile Ser
530                 535                 540
Asn Val Val Lys Asn Trp Asp Ile Glu Glu Asp Ser Leu Glu Pro Trp
545                 550                 555                 560
Val Ala Asn Asn Lys Asn Ala Tyr Val Asp Asn Thr Gly Gly Ile Glu
                565                 570                 575
Arg Ser Lys Ala Leu Phe Thr Val Gly Asp Gly Glu Phe Ser Gln Phe
            580                 585                 590
Ile Gly Asp Lys Leu Lys Pro Asn Thr Asp Tyr Ile Ile Gln Tyr Thr
            595                 600                 605
Val Lys Gly Lys Pro Ala Ile Tyr Leu Lys Asn Lys Ser Thr Gly Tyr
    610                 615                 620
Ile Thr Tyr Glu Asp Thr Asn Gly Asn Ser Glu Glu Phe Gln Thr Ile
625                 630                 635                 640
Ala Val Lys Phe Thr Ser Glu Thr Asp Leu Ser Gln Thr His Leu Val
                645                 650                 655
Phe Lys Ser Gln Asn Gly Tyr Glu Ala Trp Gly Asp Asn Phe Ile Ile
            660                 665                 670
Leu Glu Ala Lys Leu Phe Glu Thr Pro Glu Ser Pro Glu Leu Ile Lys
    675                 680                 685
Phe Asn Asp Trp Glu Arg Phe Gly Thr Thr Tyr Ile Thr Gly Asn Glu
690                 695                 700
Leu Arg Ile Asp His Ser Arg Gly Gly Tyr Phe Arg Gln Ser Leu Asn
705                 710                 715                 720
Ile Asp Ser Tyr Ser Thr Tyr Asp Leu Ser Phe Ser Phe Ser Gly Leu
                725                 730                 735
Trp Ala Lys Val Ile Val Lys Asn Ser Arg Gly Val Val Leu Phe Glu
            740                 745                 750
Lys Val Lys Asn Asn Gly Ser Ser Tyr Glu Asp Ile Ser Glu Ser Phe
        755                 760                 765
Thr Thr Ala Ser Asn Lys Asp Gly Phe Phe Ile Glu Leu Thr Ala Glu
    770                 775                 780
Arg Thr Ser Ser Thr Phe His Ser Phe Arg Asp Ile Ser Ile Lys Glu
```

-continued

```
785                 790                 795                 800

Lys Ile Glu

<210> SEQ ID NO 21
<211> LENGTH: 803
<212> TYPE: PRT
<213> ORGANISM: Artificial
<220> FEATURE:
<223> OTHER INFORMATION: AXMI115 variant sequence

<400> SEQUENCE: 21

Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
    290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350
```

```
Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Glu Phe Ser Gln Phe
            580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
                740                 745                 750

Lys Val Lys Asn Asn Gly Ser Ser Tyr Glu Asp Ile Ser Glu Asp Phe
            755                 760                 765
```

```
Thr Thr Asn Gly Phe Lys Asp Gly Phe Tyr Ile Glu Leu Thr Ala Glu
    770                 775                 780
Arg Thr Ser Ser Thr Phe His Ser Phe Arg Asp Ile Ser Ile Lys Glu
785                 790                 795                 800
Lys Ile Glu

<210> SEQ ID NO 22
<211> LENGTH: 803
<212> TYPE: PRT
<213> ORGANISM: Artificial
<220> FEATURE:
<223> OTHER INFORMATION: AXMI115 variant sequence

<400> SEQUENCE: 22

Met Asn Met Asn Thr Lys Leu Asn Ala Arg Ala Leu Pro Ser Phe
1               5                   10                  15
Ile Asp Tyr Phe Asn Gly Ile Tyr Gly Phe Ala Thr Gly Ile Lys Asp
                20                  25                  30
Ile Met Asn Met Ile Phe Lys Thr Asp Thr Gly Gly Asn Leu Thr Leu
            35                  40                  45
Asp Glu Ile Leu Lys Asn Gln Gln Leu Leu Asn Glu Ile Ser Gly Lys
50                  55                  60
Leu Asp Gly Val Asn Gly Ser Leu Asn Asp Leu Ile Ala Gln Gly Asn
65                  70                  75                  80
Leu Asn Thr Glu Leu Ser Lys Glu Ile Leu Lys Ile Ala Asn Glu Gln
                85                  90                  95
Asn Gln Val Leu Asn Asp Val Asn Asn Lys Leu Asp Ala Ile Asn Thr
            100                 105                 110
Met Leu His Ile Tyr Leu Pro Lys Ile Thr Ser Met Leu Ser Asp Val
        115                 120                 125
Met Lys Gln Asn Tyr Ala Leu Ser Leu Gln Ile Glu Tyr Leu Ser Lys
130                 135                 140
Gln Leu Gln Glu Ile Ser Asp Lys Leu Asp Ile Ile Asn Val Asn Val
145                 150                 155                 160
Leu Ile Asn Ser Thr Leu Thr Glu Ile Thr Pro Ala Tyr Gln Arg Ile
                165                 170                 175
Lys Tyr Val Asn Glu Lys Phe Asp Lys Leu Thr Phe Ala Thr Glu Ser
            180                 185                 190
Thr Leu Arg Ala Lys Gln Gly Ile Phe Asn Glu Asp Ser Phe Asp Asn
        195                 200                 205
Asn Thr Leu Glu Asn Leu Thr Asp Leu Ala Glu Leu Ala Lys Ser Ile
210                 215                 220
Thr Lys Asn Asp Val Asp Ser Phe Glu Phe Tyr Leu His Thr Phe His
225                 230                 235                 240
Asp Val Leu Ile Gly Asn Asn Leu Phe Gly Arg Ser Ala Leu Lys Thr
                245                 250                 255
Ala Ser Glu Leu Ile Thr Lys Asp Glu Ile Lys Thr Ser Gly Ser Glu
            260                 265                 270
Ile Gly Lys Val Tyr Ser Phe Leu Ile Val Leu Thr Ser Leu Gln Ala
        275                 280                 285
Lys Ala Phe Leu Thr Leu Thr Thr Cys Arg Lys Leu Leu Gly Leu Ser
290                 295                 300
Asp Ile Asp Tyr Thr Ser Ile Met Asn Glu His Leu Asn Asn Glu Lys
305                 310                 315                 320
Asn Glu Phe Arg Asp Asn Ile Leu Pro Ala Leu Ser Asn Lys Phe Ser
```

```
                325                 330                 335
Asn Pro Ser Tyr Ala Lys Thr Ile Gly Ser Asp Asn Tyr Ala Lys Val
            340                 345                 350
Ile Leu Glu Ser Glu Pro Gly Tyr Ala Leu Val Gly Phe Glu Ile Ile
                355                 360                 365
Asn Asp Pro Ile Pro Val Leu Lys Ala Tyr Lys Ala Lys Leu Lys Gln
        370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
            420                 425                 430
Glu Lys Lys Leu Asn Asn Leu Ile Tyr Glu Ala Thr Ala Asn Phe Tyr
                435                 440                 445
Asp Pro Ser Thr Gly Asp Ile Asp Leu Asn Lys Lys Gln Val Glu Ser
        450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                485                 490                 495
Ile Asn Ser Phe Gly Leu Glu Val Asp Ala Lys Ser Lys Thr Leu Thr
            500                 505                 510
Leu Lys Cys Lys Ser Tyr Leu Arg Glu Tyr Leu Leu Glu Ser Asp Leu
                515                 520                 525
Lys Asn Lys Glu Thr Gly Leu Ile Ala Pro Pro Asn Val Phe Ile Ser
        530                 535                 540
Asn Val Val Lys Asn Trp Asp Ile Glu Glu Asp Ser Leu Glu Pro Trp
545                 550                 555                 560
Val Ala Asn Asn Lys Asn Ala Tyr Val Asp Asn Thr Gly Gly Ile Glu
                565                 570                 575
Arg Ser Lys Ala Leu Phe Thr Gln Gly Asp Gly Glu Phe Ser Gln Phe
            580                 585                 590
Ile Gly Asp Lys Leu Lys Pro Asn Thr Asp Tyr Ile Ile Gln Tyr Thr
        595                 600                 605
Val Lys Gly Lys Pro Ala Ile Tyr Leu Lys Asn Lys Ser Thr Gly Tyr
        610                 615                 620
Ile Thr Tyr Glu Asp Thr Asn Gly Asn Ser Glu Glu Phe Gln Thr Ile
625                 630                 635                 640
Ala Val Lys Phe Thr Ser Glu Thr Asp Leu Ser Gln Thr His Leu Val
                645                 650                 655
Phe Lys Ser Gln Asn Gly Tyr Glu Ala Trp Gly Asp Asn Phe Ile Ile
            660                 665                 670
Leu Glu Ala Lys Leu Phe Glu Thr Pro Glu Ser Pro Glu Leu Ile Lys
        675                 680                 685
Phe Asn Asp Trp Glu Arg Phe Gly Thr Thr Tyr Ile Thr Gly Asn Glu
        690                 695                 700
Leu Arg Ile Asp His Ser Arg Gly Gly Tyr Phe Arg Gln Ser Leu Asn
705                 710                 715                 720
Ile Asp Ser Tyr Ser Thr Tyr Asp Leu Ser Phe Ser Phe Ser Gly Leu
                725                 730                 735
Trp Ala Lys Val Ile Val Lys Asn Ser Arg Gly Val Val Leu Phe Glu
            740                 745                 750
```

```
Lys Val Lys Asn Asn Gly Ser Ser Tyr Glu Asp Ile Ser Glu His Phe
        755                 760                 765

Thr Thr Trp Gly Tyr Lys Asp Gly Phe Phe Ile Glu Leu Thr Ala Glu
        770                 775                 780

Arg Thr Ser Ser Thr Phe His Ser Phe Arg Asp Ile Ser Ile Lys Glu
785                 790                 795                 800

Lys Ile Glu

<210> SEQ ID NO 23
<211> LENGTH: 803
<212> TYPE: PRT
<213> ORGANISM: Artificial
<220> FEATURE:
<223> OTHER INFORMATION: AXMI115 variant sequence

<400> SEQUENCE: 23

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
290                 295                 300
```

-continued

```
Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
            325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
            405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
            485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
            565                 570                 575

Arg Ser Lys Ala Leu Phe Val Gln Gly Asp Gly Glu Phe Ser Gln Phe
            580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
            610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
            645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
            690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
```

-continued

```
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 24
<211> LENGTH: 803
<212> TYPE: PRT
<213> ORGANISM: Artificial
<220> FEATURE:
<223> OTHER INFORMATION: AXMI115 variant sequence

<400> SEQUENCE: 24

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285
```

```
Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
                355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
                435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
                515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Lys Phe Ser Gln Phe
                580                 585                 590

Ile Gly Asp Lys Leu Lys Pro Asn Thr Asp Tyr Ile Ile Gln Tyr Thr
                595                 600                 605

Val Lys Gly Lys Pro Ala Ile Tyr Leu Lys Asn Lys Ser Thr Gly Tyr
                610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
                660                 665                 670

Leu Glu Ala Lys Leu Phe Glu Thr Pro Glu Ser Pro Glu Leu Ile Lys
                675                 680                 685

Phe Asn Asp Trp Glu Arg Phe Gly Thr Thr Tyr Ile Thr Gly Asn Glu
                690                 695                 700
```

-continued

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
            725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 25
<211> LENGTH: 803
<212> TYPE: PRT
<213> ORGANISM: Artificial
<220> FEATURE:
<223> OTHER INFORMATION: AXMI115 variant sequence

<400> SEQUENCE: 25

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
            85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
            115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
            165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
            195                 200                 205

Asn Thr Leu Glu Asn Leu Thr Asp Leu Ala Glu Leu Ala Lys Ser Ile
210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
            245                 250                 255

Ala Ser Glu Leu Ile Thr Lys Asp Glu Ile Lys Thr Ser Gly Ser Glu

-continued

```
                260                 265                 270
Ile Gly Lys Val Tyr Ser Phe Leu Ile Val Leu Thr Ser Leu Gln Ala
            275                 280                 285
Lys Ala Phe Leu Thr Leu Thr Thr Cys Arg Lys Leu Leu Gly Leu Ser
            290                 295                 300
Asp Ile Asp Tyr Thr Ser Ile Met Asn Glu His Leu Asn Asn Glu Lys
305                 310                 315                 320
Asn Glu Phe Arg Asp Asn Ile Leu Pro Ala Leu Ser Asn Lys Phe Ser
                325                 330                 335
Asn Pro Ser Tyr Ala Lys Thr Ile Gly Ser Asp Asn Tyr Ala Lys Val
            340                 345                 350
Ile Leu Glu Ser Glu Pro Gly Tyr Ala Leu Val Gly Phe Glu Ile Ile
            355                 360                 365
Asn Asp Pro Ile Pro Val Leu Lys Ala Tyr Lys Ala Lys Leu Lys Gln
            370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
            420                 425                 430
Glu Lys Lys Leu Asn Asn Leu Ile Tyr Glu Ala Thr Ala Asn Phe Tyr
            435                 440                 445
Asp Pro Ser Thr Gly Asp Ile Asp Leu Asn Lys Lys Gln Val Glu Ser
            450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                485                 490                 495
Ile Asn Ser Phe Gly Leu Glu Val Asp Ala Lys Ser Lys Thr Leu Thr
            500                 505                 510
Leu Lys Cys Lys Ser Tyr Leu Arg Glu Tyr Leu Leu Glu Ser Asp Leu
            515                 520                 525
Lys Asn Lys Glu Thr Gly Leu Ile Ala Pro Pro Asn Val Phe Ile Ser
            530                 535                 540
Asn Val Val Lys Asn Trp Asp Ile Glu Glu Asp Ser Leu Glu Pro Trp
545                 550                 555                 560
Val Ala Asn Asn Lys Asn Ala Tyr Val Asp Asn Thr Gly Gly Ile Glu
                565                 570                 575
Arg Ser Lys Ala Leu Phe Thr Leu Gly Asp Gly Glu Phe Ser Gln Phe
            580                 585                 590
Ile Gly Asp Lys Leu Lys Pro Asn Thr Asp Tyr Ile Ile Gln Tyr Thr
            595                 600                 605
Val Lys Gly Lys Pro Ala Ile Tyr Leu Lys Asn Lys Ser Thr Gly Tyr
            610                 615                 620
Ile Thr Tyr Glu Asp Thr Asn Gly Asn Ser Glu Glu Phe Gln Thr Ile
625                 630                 635                 640
Ala Val Lys Phe Thr Ser Glu Thr Asp Leu Ser Gln Thr His Leu Val
                645                 650                 655
Phe Lys Ser Gln Asn Gly Tyr Glu Ala Trp Gly Asp Asn Phe Ile Ile
            660                 665                 670
Leu Glu Ala Lys Leu Phe Glu Thr Pro Glu Ser Pro Glu Leu Ile Lys
            675                 680                 685
```

```
Phe Asn Asp Trp Glu Arg Phe Gly Thr Thr Tyr Ile Thr Gly Asn Glu
    690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
                740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
        770                 775                 780

Arg Thr Ser Ser Thr Phe His Ser Phe Arg Asp Ile Ser Ile Lys Glu
785                 790                 795                 800

Lys Ile Glu
```

<210> SEQ ID NO 26
<211> LENGTH: 803
<212> TYPE: PRT
<213> ORGANISM: Artificial
<220> FEATURE:
<223> OTHER INFORMATION: Axmi115 variant sequence

<400> SEQUENCE: 26

```
Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240
```

```
Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Lys Gly Asp Gly Glu Phe Ser Gln Phe
            580                 585                 590

Ile Gly Asp Lys Leu Lys Pro Asn Thr Asp Tyr Ile Ile Gln Tyr Thr
        595                 600                 605

Val Lys Gly Lys Pro Ala Ile Tyr Leu Lys Asn Lys Ser Thr Gly Tyr
610                 615                 620

Ile Thr Tyr Glu Asp Thr Asn Gly Asn Ser Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
```

```
                    660                 665                 670
Leu Glu Ala Lys Leu Phe Glu Thr Pro Glu Ser Pro Glu Leu Ile Lys
                675                 680                 685

Phe Asn Asp Trp Glu Arg Phe Gly Thr Thr Tyr Ile Thr Gly Asn Glu
            690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
                755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 27
<211> LENGTH: 803
<212> TYPE: PRT
<213> ORGANISM: Artificial
<220> FEATURE:
<223> OTHER INFORMATION: AXMI115 variant sequence

<400> SEQUENCE: 27

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220
```

-continued

```
Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
            420                 425                 430

Glu Lys Lys Leu Asn Asn Leu Ile Tyr Glu Ala Thr Ala Asn Phe Tyr
        435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Val Gly Asp Gly Lys Phe Ser Gln Phe
            580                 585                 590

Ile Gly Asp Lys Leu Lys Pro Asn Thr Asp Tyr Ile Ile Gln Tyr Thr
        595                 600                 605

Val Lys Gly Lys Pro Ala Ile Tyr Leu Lys Asn Lys Ser Thr Gly Tyr
610                 615                 620

Ile Thr Tyr Glu Asp Thr Asn Gly Asn Ser Glu Glu Phe Gln Thr Ile
625                 630                 635                 640
```

-continued

Ala Val Lys Phe Thr Ser Glu Thr Asp Leu Ser Gln Thr His Leu Val
            645                 650                 655

Phe Lys Ser Gln Asn Gly Tyr Glu Ala Trp Gly Asp Asn Phe Ile Ile
        660                 665                 670

Leu Glu Ala Lys Leu Phe Glu Thr Pro Glu Ser Pro Glu Leu Ile Lys
        675                 680                 685

Phe Asn Asp Trp Glu Arg Phe Gly Thr Thr Tyr Ile Thr Gly Asn Glu
    690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
                740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
        770                 775                 780

Arg Thr Ser Ser Thr Phe His Ser Phe Arg Asp Ile Ser Ile Lys Glu
785                 790                 795                 800

Lys Ile Glu

<210> SEQ ID NO 28
<211> LENGTH: 803
<212> TYPE: PRT
<213> ORGANISM: Artificial
<220> FEATURE:
<223> OTHER INFORMATION: AXMI115 variant sequence

<400> SEQUENCE: 28

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn

```
            195                 200                 205
Asn Thr Leu Glu Asn Leu Thr Asp Leu Ala Glu Leu Ala Lys Ser Ile
210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                    245                 250                 255

Ala Ser Glu Leu Ile Thr Lys Asp Glu Ile Lys Thr Ser Gly Ser Glu
        260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                    325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                    405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
        450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                    485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
        530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                    565                 570                 575

Arg Ser Lys Ala Leu Phe Thr Gln Ser Asp Gly Glu Phe Ser Gln Phe
                580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
        610                 615                 620
```

```
Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
            645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
            690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Ala Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 29
<211> LENGTH: 803
<212> TYPE: PRT
<213> ORGANISM: Artificial
<220> FEATURE:
<223> OTHER INFORMATION: AXMI115 variant sequence

<400> SEQUENCE: 29

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
    130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175
```

```
Lys Tyr Val Asn Glu Lys Phe Asp Lys Leu Thr Phe Ala Thr Glu Ser
                180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
    210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
        260                 265                 270

Ile Gly Lys Val Tyr Ser Phe Leu Ile Val Leu Thr Ser Leu Gln Ala
    275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
        340                 345                 350

Ile Leu Glu Ser Glu Pro Gly Tyr Ala Leu Val Gly Phe Glu Ile Ile
    355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
        420                 425                 430

Glu Lys Lys Leu Asn Asn Leu Ile Tyr Glu Ala Thr Ala Asn Phe Tyr
    435                 440                 445

Asp Pro Ser Thr Gly Asp Ile Asp Leu Asn Lys Lys Gln Val Glu Ser
450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
        500                 505                 510

Leu Lys Cys Lys Ser Tyr Leu Arg Glu Tyr Leu Leu Glu Ser Asp Leu
    515                 520                 525

Lys Asn Lys Glu Thr Gly Leu Ile Ala Pro Pro Asn Val Phe Ile Ser
530                 535                 540

Asn Val Val Lys Asn Trp Asp Ile Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Val Phe Ser Gln Phe
        580                 585                 590

Ile Gly Asp Lys Leu Lys Pro Asn Thr Asp Tyr Ile Ile Gln Tyr Thr
```

```
                595                 600                 605
Val Lys Gly Lys Pro Ala Ile Tyr Leu Lys Asn Lys Ser Thr Gly Tyr
610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
                660                 665                 670

Leu Glu Ala Lys Leu Phe Glu Thr Pro Glu Ser Pro Glu Leu Ile Lys
                675                 680                 685

Phe Asn Asp Trp Glu Arg Phe Gly Thr Thr Tyr Ile Thr Gly Asn Glu
690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
                740                 745                 750

Lys Val Lys Asn Asn Gly Ser Ser Tyr Glu Asp Ile Ser Glu Ser Phe
                755                 760                 765

Thr Thr Ala Ser Asn Lys Asp Gly Phe Phe Ile Glu Leu Thr Ala Glu
                770                 775                 780

Arg Thr Ser Ser Thr Phe His Ser Phe Arg Asp Ile Ser Ile Lys Glu
785                 790                 795                 800

Lys Ile Glu

<210> SEQ ID NO 30
<211> LENGTH: 803
<212> TYPE: PRT
<213> ORGANISM: Artificial
<220> FEATURE:
<223> OTHER INFORMATION: AXMI115 variant sequence

<400> SEQUENCE: 30

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asp Leu Thr Leu
                35                  40                  45

Asp Glu Ile Leu Lys Asn Gln Gln Leu Leu Asn Glu Ile Ser Gly Lys
50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
                100                 105                 110

Met Leu Asn Ile Tyr Leu Pro Lys Ile Thr Ser Met Leu Ser Asp Val
                115                 120                 125

Met Lys Gln Asn Tyr Ala Leu Ser Leu Gln Ile Glu Tyr Leu Ser Arg
                130                 135                 140

Gln Leu Gln Glu Ile Ser Asp Lys Leu Asp Val Ile Asn Leu Asn Val
145                 150                 155                 160
```

```
Leu Ile Asn Ser Thr Leu Thr Glu Ile Thr Pro Ser Tyr Gln Arg Ile
                165                 170                 175
Lys Tyr Val Asn Glu Lys Phe Asp Lys Leu Thr Phe Ala Thr Glu Ser
            180                 185                 190
Thr Leu Arg Ala Lys Gln Gly Ile Phe Asn Glu Asp Ser Phe Asp Asn
        195                 200                 205
Asn Thr Leu Glu Asn Leu Thr Asp Leu Ala Glu Leu Ala Lys Ser Ile
    210                 215                 220
Thr Lys Asn Asp Val Asp Ser Phe Glu Phe Tyr Leu His Thr Phe His
225                 230                 235                 240
Asp Val Leu Ile Gly Asn Asn Leu Phe Gly Arg Ser Ala Leu Lys Thr
                245                 250                 255
Ala Ser Glu Leu Ile Thr Lys Asp Glu Ile Lys Thr Ser Gly Ser Glu
            260                 265                 270
Ile Gly Lys Val Tyr Ser Phe Leu Ile Val Leu Thr Ser Leu Gln Ala
        275                 280                 285
Lys Ala Phe Leu Thr Leu Thr Thr Cys Arg Lys Leu Leu Gly Leu Ser
    290                 295                 300
Asp Ile Asp Tyr Thr Ser Ile Met Asn Glu His Leu Asn Asn Glu Lys
305                 310                 315                 320
Asn Glu Phe Arg Asp Asn Ile Leu Pro Ala Leu Ser Asn Lys Phe Ser
                325                 330                 335
Asn Pro Ser Tyr Ala Lys Thr Ile Gly Ser Asp Asn Tyr Ala Lys Val
            340                 345                 350
Ile Leu Glu Ser Glu Pro Gly Tyr Ala Leu Val Gly Phe Glu Ile Ile
        355                 360                 365
Asn Asp Pro Ile Pro Val Leu Lys Ala Tyr Lys Ala Lys Leu Lys Gln
    370                 375                 380
Asn Tyr Gln Val Asp Asn Gln Ser Leu Ser Glu Ile Val Tyr Leu Asp
385                 390                 395                 400
Ile Asp Lys Leu Phe Cys Pro Glu Asn Ser Glu Gln Lys Tyr Tyr Thr
                405                 410                 415
Lys Asn Leu Thr Phe Pro Asp Gly Tyr Val Ile Thr Lys Ile Thr Phe
            420                 425                 430
Glu Lys Lys Leu Asn Asn Leu Ile Tyr Glu Ala Thr Ala Asn Phe Tyr
        435                 440                 445
Asp Pro Ser Thr Gly Asp Ile Asp Leu Asn Lys Lys Gln Val Glu Ser
    450                 455                 460
Thr Phe Pro Gln Thr Asp Tyr Ile Thr Met Asp Ile Gly Asp Asp Asp
465                 470                 475                 480
Gly Ile Tyr Met Pro Leu Gly Val Ile Ser Glu Thr Phe Leu Thr Pro
                485                 490                 495
Ile Asn Ser Phe Gly Leu Glu Val Asp Ala Lys Ser Lys Thr Leu Thr
            500                 505                 510
Leu Lys Cys Lys Ser Tyr Leu Arg Glu Tyr Leu Leu Glu Ser Asp Leu
        515                 520                 525
Lys Asn Lys Glu Thr Gly Leu Ile Ala Pro Pro Asn Val Phe Ile Ser
    530                 535                 540
Asn Val Val Lys Asn Trp Asp Ile Glu Glu Asp Ser Leu Glu Pro Trp
545                 550                 555                 560
Val Ala Asn Asn Lys Asn Ala Tyr Val Asp Asn Thr Gly Gly Ile Glu
                565                 570                 575
```

```
Arg Ser Lys Ala Leu Phe Thr Gln Gly Asp Gly Glu Phe Ser Gln Phe
            580                 585                 590

Ile Gly Asp Lys Leu Lys Pro Asn Thr Asp Tyr Ile Ile Gln Tyr Thr
        595                 600                 605

Val Lys Gly Lys Pro Ala Ile Tyr Leu Lys Asn Lys Ser Thr Gly Tyr
    610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
            645                 650                 655

Phe Lys Ser Gln Asn Gly Tyr Glu Ala Trp Gly Asp Asn Phe Ile Ile
        660                 665                 670

Leu Glu Ala Lys Leu Phe Glu Thr Pro Glu Ser Pro Glu Leu Ile Lys
    675                 680                 685

Phe Asn Asp Trp Glu Arg Phe Gly Thr Thr Tyr Ile Thr Gly Asn Glu
690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
            725                 730                 735

Trp Ala Lys Val Ile Val Lys Asn Ser Arg Gly Val Val Leu Phe Glu
        740                 745                 750

Lys Val Lys Asn Asn Gly Ser Ser Tyr Glu Asp Ile Ser Glu Ser Phe
    755                 760                 765

Thr Thr Cys Ser Asn Lys Asp Gly Phe Phe Ile Glu Leu Thr Ala Glu
770                 775                 780

Arg Thr Ser Ser Thr Phe His Ser Phe Arg Asp Ile Ser Ile Lys Glu
785                 790                 795                 800

Lys Ile Glu

<210> SEQ ID NO 31
<211> LENGTH: 803
<212> TYPE: PRT
<213> ORGANISM: Artificial
<220> FEATURE:
<223> OTHER INFORMATION: AXMI115 variant sequence

<400> SEQUENCE: 31

Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
            85                  90                  95

Asn Gln Val Leu Asn Asp Val Asn Asn Lys Leu Asp Ala Ile Asn Thr
        100                 105                 110

Met Leu Asn Ile Tyr Leu Pro Lys Ile Thr Ser Met Leu Ser Asp Val
    115                 120                 125

Met Lys Gln Asn Tyr Ala Leu Ser Leu Gln Ile Glu Tyr Leu Ser Arg
```

```
            130                 135                 140
Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
                180                 185                 190

Thr Leu Arg Ala Lys Gln Gly Ile Phe Asn Glu Asp Ser Phe Asp Asn
            195                 200                 205

Asn Thr Leu Glu Asn Leu Thr Asp Leu Ala Glu Leu Ala Lys Ser Ile
        210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
                260                 265                 270

Ile Gly Lys Val Tyr Ser Phe Leu Ile Val Leu Thr Ser Leu Gln Ala
            275                 280                 285

Lys Ala Phe Leu Thr Leu Thr Thr Cys Arg Lys Leu Leu Gly Leu Ser
        290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
                340                 345                 350

Ile Leu Glu Ser Glu Pro Gly Tyr Ala Leu Val Gly Phe Glu Ile Ile
            355                 360                 365

Asn Asp Pro Ile Pro Val Leu Lys Ala Tyr Lys Ala Lys Leu Lys Gln
        370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415

Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
        450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
                500                 505                 510

Leu Lys Cys Lys Ser Tyr Leu Arg Glu Tyr Leu Leu Glu Ser Asp Leu
            515                 520                 525

Lys Asn Lys Glu Thr Gly Leu Ile Ala Pro Pro Asn Val Phe Ile Ser
        530                 535                 540

Asn Val Val Lys Asn Trp Asp Ile Glu Glu Asp Ser Leu Glu Pro Trp
545                 550                 555                 560
```

```
Val Ala Asn Asn Lys Asn Ala Tyr Val Asp Asn Thr Gly Gly Ile Glu
            565                 570                 575

Arg Ser Lys Ala Leu Phe Thr Gln Gly Asp Gly Glu Phe Ser Gln Phe
            580                 585                 590

Ile Gly Asp Lys Leu Lys Pro Asn Thr Asp Tyr Ile Ile Gln Tyr Thr
            595                 600                 605

Val Lys Gly Lys Pro Ala Ile Tyr Leu Lys Asn Lys Ser Thr Gly Tyr
            610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
            645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
            675                 680                 685

Phe Asn Asp Trp Glu Arg Phe Gly Thr Thr Tyr Ile Thr Gly Asn Glu
            690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
            725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
            755                 760                 765

Thr Thr Met Ser Asn Lys Asp Gly Phe Phe Ile Glu Leu Thr Ala Glu
            770                 775                 780

Arg Thr Ser Ser Thr Phe His Ser Phe Arg Asp Ile Ser Ile Lys Glu
785                 790                 795                 800

Lys Ile Glu

<210> SEQ ID NO 32
<211> LENGTH: 2445
<212> TYPE: DNA
<213> ORGANISM: Artificial
<220> FEATURE:
<223> OTHER INFORMATION: Axmi115 variant sequence

<400> SEQUENCE: 32
atggcacatc accaccacca tcacggatcc accatgaaca tgaacaacac caagctcaat      60
gcaagggcgc tgccgagctt catcgactac ttcaatggca tctatggctt cgccaccggc     120
atcaaggaca tcatgaacat gatcttcaag accgacaccg gcggcaacct caccttggat     180
gagatcctca agaaccagca gctgctgaat gagatctcag gcaagctgga cggcgtcaat     240
ggaagcctca cgacctcat tgctcaaggc aacctcaaca ccgagctgag caaggagatc     300
ctcaagattg caaatgagca gaaccaggtg ctgaatgatg tcaacaacaa gctggacgcc     360
atcaacacca tgctgcacat ctacctgcca aagatcacct caatgctctc tgatgtgatg     420
aagcagaact acgcgctgag cctccagatt gagtacctct caaagcagct gcaagagatc     480
tccgacaagc tggacatcat caatgtcaat gtgctcatca acagcacctt gacagagatc     540
acgccggcct accagaggat caagtatgtc aatgagaagt cgacaagct cacccttcgcc     600 accgagagca ccctccgcgc caagcaaggc atcttcaatg aagattcatt tgacaacaac     660
```

```
accttggaga acttgacaga cctcgccgag ctggccaaga gcatcaccaa gaatgatgtg      720
gacagcttcg agttctacct ccacaccttc catgatgtgc tcatcggcaa caacctcttt      780
ggaagaagcg cgctcaagac ggcatcagag ctcatcacca aggatgagat caagacaagc      840
ggcagcgaga tcggcaaggt ctacagcttc ctcatcgtgc tgacatcatt gcaagccaag      900
gccttcctca ccttgacaac ctgccgcaag ttgctgggcc tctccgacat cgactacacc      960
tccatcatga atgagcacct caacaatgag aagaatgagt tcagagacaa catcctgccg     1020
gcgctgagca acaagttcag caacccaagc tacgccaaga ccatcggctc agacaactac     1080
gccaaggtga tcctggagag cgagcctggc tacgcgctgg tgggcttcga gatcatcaat     1140
gatccaattc tgttctcaa ggcctacaag gccaagctga agcagaacta ccaggtggac      1200
aaccagagct tgagcgagat cgtctacctg gacatcgaca agctcttctg cccggagaac     1260
tcagagcaga agtactacac caagaacctc accttccctg atggatatgt catcaccaag     1320
atcaccttcg agaagaagct gaacaacctc atctacgagg ccaccgccaa cttctatgat     1380
ccatcaacag gagacatcga cctcaacaag aagcaagtgg agagcacctt ccctcaaaca     1440
gactacatca ccatggacat tggagatgat gatggcatct acatgccgct cggcgtcatc     1500
tcagaaacct tcttgacgcc catcaacagc ttcggcctgg aggtggacgc caagagcaag     1560
accttgacgc tcaagtgcaa gagctacctc agggagtacc tgctggagag tgatttgaag     1620
aacaaggaga cagggctgat cgcgccgcca aatgtgttca tcagcaatgt ggtgaagaac     1680
tgggacatcg aggaggattc attggagcca tgggtggcca acaacaagaa tgcttatgtg     1740
gacaacaccg gcggcattga agaagcaag gcgctcttca cccaaggaga tggagagttc     1800
agccagttca tcggcgacaa gctaaagccc aacaccgact acatcatcca gtacaccgtc     1860
aagggcaagc cggccatcta cctcaagaac aagagcaccg gctacatcac ctacgaggac     1920
accaatggaa attctgagga gttccaaaca attgctgtga agttcacctc agaaacagat     1980
ttgagccaga cccacctggt gttcaagagc caaaatggat atgaagcatg gggagacaac     2040
ttcatcatcc tggaggccaa gctcttcgag acaccagaaa gcccggagct catcaagttc     2100
aatgattggg agaggttcgg caccacctac atcaccggca tgagctgag gattgatcat     2160 tcaagaggag gctacttccg ccaaagcctc aacatcgaca gctacagcac ctacgacctc     2220
agcttcagct tcagcggcct ctgggccaag gtgattgtga gaacagccg cggcgtggtg     2280 ctcttcgaga aggtgaagaa caatggaagc agctatgagg acatctcaga gagcttcacc     2340
accgccagca caaggatgg cttcttcatc gagctcaccg ccgagaggac aagcagcacc     2400
ttccacagct tcagagacat cagcatcaag gagaagattg aataa                    2445
```

<210> SEQ ID NO 33
<211> LENGTH: 2430
<212> TYPE: DNA
<213> ORGANISM: Artificial
<220> FEATURE:
<223> OTHER INFORMATION: Axmi115 variant sequence

<400> SEQUENCE: 33

```
atggcacatc accaccacca tcacggatcc accatgaaca tgaacaacac caagctcaat       60
gcaagggcgc tgccgagctt catcgactac ttcaatggca tctatggctt cgccaccggc      120
atcaaggaca tcatgaacat gatcttcaag accgacaccg gcggcaacct caccttggat      180
gagatcctca agaaccagca gctgctgaat gagatctcag gcaagctgga cggcgtcaat      240
```

```
ggaagcctca acgacctcat tgctcaaggc aacctcaaca ccgagctgag caaggagatc    300
ctcaagattg caaatgagca gaaccaggtg ctgaatgatg tcaacaacaa gctggacgcc    360
atcaacacca tgctgcacat ctacctgcca aagatcacct caatgctctc tgatgtgatg    420
aagcagaact acgcgctgag cctccagatt gagtacctct caaagcagct gcaagagatc    480
tccgacaagc tggacatcat caatgtcaat gtgctcatca acagcacctt gacagagatc    540
acgccggcct accagaggat caagtatgtc aatgagaagt ttgaggagct caccttcgcc    600
accgagacaa cattgaaggt gaagaaggac agctcgccgg cggacatcct ggatgagctc    660
accgagctaa cagagctggc caagagcgtc accaagaatg atgttgatgg cttcgagttc    720
tacctcaaca ccttccatga tgtgatggtg ggcaacaacc tcttcggccg ctcggcgctc    780
aagacggcgt cggagctgat cgccaaggag aatgtcaaga caagtggatc agaggtgggc    840
aatgtctaca acttcctcat cgtgctgacg gcgctgcaag ccaaggcctt cctcaccttg    900
acaacctgcc gcaagttgct gggcctctcc gacatcgact acacctccat catgaatgag    960
cacctcaaca atgagaagaa tgagttcaga gacaacatcc tgccggcgct gagcaacaag   1020
ttcagcaacc caagctacgc caagaccatc ggctcagaca actacgccaa ggtgatcctg   1080
gagagcgagc ctggctacgc gctggtgggc ttcgagatca tcaatgatcc aattcctgtt   1140
ctcaaggcct acaaggccaa gctgaagcag aactaccagg tggacaacca gagcttgagc   1200
gagatcgtct acctggacat cgacaagctc ttctgcccgg agaactcaga gcagaagtac   1260
tacaccaaga acctcacctt ccctgatgga tatgtcatca ccaagatcac cttcgagaag   1320
aagctgaaca acctcatcta cgaggccacc gccaacttct atgatccatc aacaggagac   1380
atcgacctca acaagaagca agtggagagc accttccctc aaacagacta catcaccatg   1440
gacattggag atgatgatgg catctacatg ccgctcggcg tcatctcaga aaccttcttg   1500
acgcccatca acagcttcgg cctggaggtg gacgccaaga gcaagacctt gacgctcaag   1560
tgcaagagct acctcaggga gtacctgctg gagagtgatt tgaagaacaa ggagacaggg   1620
ctgatcgcgc cgccaaatgt gttcatcagc aatgtggtga agaactggga catcgaggag   1680
gattcattgg agccatgggt ggccaacaac aagaatgctt atgtggacaa caccggcggc   1740
attgaaagaa gcaaggcgct cttcacccaa ggagatggag agttcagcca gttcatcggc   1800
gacaagctaa agcccaacac cgactacatc atccagtaca ccgtcaaggg caagccggcc   1860
atctacctca agaacaagag caccggctac atcacctacg aggacaccaa tggaaattct   1920
gaggagttcc aaacaattgc tgtgaagttc acctcagaaa cagatttgag ccagacccac   1980
ctggtgttca agagccaaaa tggatatgaa gcatggggag acaacttcat catcctggag   2040
gccaagctct tcgagacacc agaaagcccg gagctcatca agttcaatga ttgggagagg   2100
ttcggcacca cctacatcac cggcaatgag ctgaggattg atcattcaag aggaggctac   2160
ttccgccaaa gcctcaacat cgacagctac agcacctacg acctcagctt cagcttcagc   2220
ggcctctggg ccaaggtgat tgtgaagaac agccgcggcg tggtgctctt cgagaaggtg   2280
aagaacaatg gaagcagcta tgaggacatc tcagagagct tcaccaccgc cagcaacaag   2340
gatggcttct tcatcgagct caccgccgag aggacaagca gcaccttcca cagcttcaga   2400
gacatcagca tcaaggagaa gattgaataa                                    2430
```

<210> SEQ ID NO 34
<211> LENGTH: 2454
<212> TYPE: DNA
<213> ORGANISM: Artificial
<220> FEATURE:
<223> OTHER INFORMATION: Axmi115 variant sequence

<400> SEQUENCE: 34

| | | |
|---|---|---|
| atggcacatc accaccacca tcacggatcc accatggcac atcaccacca ccatcacgga | 60 |
| tccaccatga acatgaacaa caccaagctc aatgcaaggg cgctgccgag cttcatcgac | 120 |
| tacttcaatg gcatctatgg cttcgccacc ggcatcaagg acatcatgaa catgatcttc | 180 |
| aagaccgaca ccggcggcaa cctcaccttg gatgagatcc tcaagaacca gcagctgctg | 240 |
| aatgagatct caggcaagct ggacggcgtc aatggaagcc tcaacgacct cattgctcaa | 300 |
| ggcaacctca acaccgagct gagcaaggag atcctcaaga ttgcaaatga gcagaaccag | 360 |
| gtgctgaatg atgtcaacaa caagctggac gccatcaaca ccatgctgca catctacctg | 420 |
| ccaaagatca cctcaatgct ctctgatgtg atgaagcaga actacgcgct gagcctccag | 480 |
| attgagtacc tctcaaagca gctgcaagag atctccgaca agctggacat catcaatgtc | 540 |
| aatgtgctca tcaacagcac cttgacagag atcacgccgg cctaccagag gatcaagtat | 600 |
| gtcaatgaga agtttgagga gctcaccttc gccaccgaga caacattgaa ggtgaagaag | 660 |
| gacagctcgc cggcggacat cctggatgag ctcaccgagc taacagagct ggccaagagc | 720 |
| gtcaccaaga atgatgttga tggcttcgag ttctacctca acaccttcca tgatgtgatg | 780 |
| gtggcaaca acctcttcgg ccgctcggcg ctcaagacgg cgtcggagct gatcgccaag | 840 |
| gagaatgtca agacaagtgg atcagaggtg gcaatgtct acaacttcct catcgtgctg | 900 |
| acggcgctgc aagccaaggc cttcctcacc ttgacaacct gccgcaagtt gctgggcctc | 960 |
| gccgacatcg actacacctc catcatgaat gagcacctca caaggagaa ggaggagttc | 1020 |
| cgcgtcaaca tcctgccaac attgagcaac accttcagca accccaacta cgccaaggtg | 1080 |
| aagggctcag atgaagatgc caagatgatt gtggaggcca agcctggcca tgctctggtg | 1140 |
| ggcttcgaga tgagcaacga cagcatcacc gtgctgaagg tctacgaggc caagctgaag | 1200 |
| cagaactacc aggtggacaa ggacagcttg tctgaggtga tctacggcga catggacaag | 1260 |
| ctgctatgtc cagatcaaag cgagcagatc tactacacca caacatcgt ctttccaaat | 1320 |
| gaatatgtca tcaccaagat cgacttcacc aagaagatga aaacattgag atatgaggtg | 1380 |
| acggccaaca gctacgacag cagcaccggc gagatcgacc tcaacaagaa gaaggtggag | 1440 |
| agctcagaag ctgagtacag gacgctctcc gccaaggatg atggcgtcta catgccgctc | 1500 |
| ggcgtcatct cagaaacctt cttgacgccc atcaatggct tcggcctcca agctgatgag | 1560 |
| aacagcaggc tcatcacctt gacctgcaag agctacctca gggagctgct gctggccacc | 1620 |
| gacctcagca acaaggagac aaagctcatc gtgccgccat caggcttcat cagcaacatc | 1680 |
| gtggagaatg gcaacctgga aggagagaac ctggagccat ggatagccaa caacaagaat | 1740 |
| gcttatgttg atcacaccgg cggcgtcaat ggaacaaggg cgctctatgt tcacaaggat | 1800 |
| ggaggcttca gccagttcat cggcgacaag ctgaagccca agacagaata tgtcatccag | 1860 |
| tacaccgtca agggcaagcc ggccatctac ctcaagaaca gagcaccgg ctacatcacc | 1920 |
| tacgaggaca ccaatggaaa ttctgaggag ttccaaacaa ttgctgtgaa gttcaccctca | 1980 |
| gaaacagatt tgagccagac ccacctggtg ttcaagagcc aaaatggata tgaagcatgg | 2040 |
| ggagacaact tcatcatcct ggaggccaag ctcttcgaga caccagaaag cccggagctc | 2100 |
| atcaagttca atgattggga gaggttcggc accacctaca tcaccggcaa tgagctgagg | 2160 |
| attgatcatt caagaggagg ctacttccgc caaagcctca catcgacag ctacagcacc | 2220 |

```
tacgacctca gcttcagctt cagcggcctc tgggccaagg tgattgtgaa gaacagccgc   2280
ggcgtggtgc tcttcgagaa ggtgaagaac aatggaagca gctatgagga catctcagag   2340
agcttcacca ccgccagcaa caaggatggc ttcttcatcg agctcaccgc cgagaggaca   2400
agcagcacct ccacagcttc agagacatc agcatcaagg agaagattga ataa          2454

<210> SEQ ID NO 35
<211> LENGTH: 2442
<212> TYPE: DNA
<213> ORGANISM: Artificial
<220> FEATURE:
<223> OTHER INFORMATION: Axmi115 variant sequence

<400> SEQUENCE: 35
atggcacatc accaccacca tcacggatcc accatgaaca tgaacaacac caagctcaat     60
gcaagggcgc tgccgagctt catcgactac ttcaatggca tctatggctt cgccaccggc   120
atcaaggaca tcatgaacat gatcttcaag accgacaccg gcggcaacct caccttggat   180
gagatcctca agaaccagca gctgctgaat gagatctcag gcaagctgga cggcgtcaat   240
ggaagcctca cgacctcat tgctcaaggc aacctcaaca ccgagctgag caaggagatc   300
ctcaagattg caaatgagca gaaccaggtg ctgaatgatg tcaacaacaa gctggacgcc   360
atcaacacca tgctgcacat ctacctgcca aagatcacct caatgctctc tgatgtgatg   420
aagcagaact acgcgctgag cctccagatt gagtacctct caaagcagct gcaagagatc   480
tccgacaagc tggacatcat caatgtcaat gtgctcatca acagcacctt gacagagatc   540
acgccggcct accagaggat caagtatgtc aatgagaagt cgacaagct cacctgcgcc  600 accgagagca ccctccgcgc caagcaaggc atcttcaatg aagattcatt tgacaacaac   660
accttggaga acttgacaga cctcgccgag ctggccaaga gcatcaccaa gaatgatgtg   720
gacagcttcg agttctacct ccacaccttc catgatgtgc tcatcggcaa caacctcttt   780
ggaagaagcg cgctcaagac ggcatcgagg ctcatcacca aggatgagat caagacaagc   840
ggcagcgaga tcggcaaggt ctacagcttc ctcatcgtgc tgacatcatt gcaagccaag   900
gccttcctca ccttgacaac ctgccgcaag ttgctgggcc tctccgacat cgactacacc   960
tccatcatga atgagcacct caacaatgag aagaatgagt tcagagacaa catcctgccg  1020
gcgctgagca caagttcag caacccaagc tacgccaaga ccatcggctc agacaactac  1080
gccaaggtga tcctggagag cgagcctggc tacgcgctgg tgggcttcga gatcatcaat  1140
gatccaattc ctgttctcaa ggcctacaag gccaagctga agcagaacta ccaggtggac  1200
aaccagagct tgagcgagat cgtctacctg gacatcgaca gctcttctg cccggagaac   1260 tcagagcaga agtactacac caagaacctc accttccctg atggatatgt catcaccaag   1320
atcaccttcg agaagaagct gaacaacctc atctacgagg ccaccgccaa cttctatgat   1380
ccatcaacag gagacatcga cctcaacaag aagcaagtgg agagcacctt ccctcaaaca   1440
gactacatca ccatggacat tggagatgat gatggcatct acatgccgct cggcgtcatc   1500
tcagaaacct tcttgacgcc catcaacagc ttcggcctgg aggtggacgc caagagcaag   1560
accttgacgc tcaagtgcaa gagctacctc agggagtacc tgctggagag tgatttgaag   1620
aacaaggaga cagggctgat cgcgccgcca aatgtgttca tcagcaatgt ggtgaagaac   1680
tgggacatcg aggaggattc attggagcca tgggtggcca acaacaagaa tgcttatgtg   1740
gacaacaccg gcggcattga agaagcaag gcgctcttca cccaaggaga tggagagttc   1800
agccagttca tcggcgacaa gctaaagccc aacaccgact acatcatcca gtacaccgtc   1860
```

| | |
|---|---|
| aagggcaagc cggccatcta cctcaagaac aagagcaccg gctacatcac ctacgaggac | 1920 |
| accaatggaa attctgagga gttccaaaca attgctgtga agttcacctc agaaacagat | 1980 |
| ttgagccaga cccacctggt gttcaagagc caaaatggat atgaagcatg gggagacaac | 2040 |
| ttcatcatcc tggaggccaa gctcttcgag acaccagaaa gcccggagct catcaagttc | 2100 |
| aatgattggg agaggttcgg caccacctac atcaccggca atgagctgag gattgatcat | 2160 |
| tcaagaggag gctacttccg ccaaagcctc aacatcgaca gctacagcac ctacgacctc | 2220 |
| agcttcagct tcagcggcct ctgggccaag gtgattgtga agaacagccg cggcgtggtg | 2280 |
| ctcttcgaga aggtgaagaa caatggaagc agctatgagg acatctcaga ggacttcacc | 2340 |
| accaatggct ttaaggatgg cttctatatc gagctcaccg ccgagaggac aagcagcacc | 2400 |
| ttccacagct tcagagacat cagcatcaag gagaagattg aa | 2442 |

<210> SEQ ID NO 36
<211> LENGTH: 2442
<212> TYPE: DNA
<213> ORGANISM: Artificial
<220> FEATURE:
<223> OTHER INFORMATION: Axmi115 variant sequence

<400> SEQUENCE: 36

| | |
|---|---|
| atggcacatc accaccacca tcacggatcc accatgaaca tgaacaacac caagctcaat | 60 |
| gcaagggcgc tgccgagctt catcgactac ttcaatggca tctatggctt cgccaccggc | 120 |
| atcaaggaca tcatgaacat gatcttcaag accgacaccg gcggcaacct caccttggat | 180 |
| gagatcctca agaaccagca gctgctgaat gagatctcag gcaagctgga cggcgtcaat | 240 |
| ggaagcctca cgacctcat tgctcaaggc aacctcaaca ccgagctgag caaggagatc | 300 |
| ctcaagattg caaatgagca gaaccaggtg ctgaatgatg tcaacaacaa gctggacgcc | 360 |
| atcaacacca tgctgcacat ctacctgcca aagatcacct caatgctctc tgatgtgatg | 420 |
| aagcagaact acgcgctgag cctccagatt gagtacctct caaagcagct gcaagagatc | 480 |
| tccgacaagc tggacatcat caatgtcaat gtgctcatca acagcacctt gacagagatc | 540 |
| acgccggcct accagaggat caagtatgtc aatgagaagt cgacaagct cacctttcgc | 600 |
| accgagagca ccctccgcgc caagcaaggc atcttcaatg aagattcatt tgacaacaac | 660 |
| accttggaga acttgacaga cctcgccgag ctggccaaga gcatcaccaa gaatgatgtg | 720 |
| gacagcttcg agttctacct ccacaccttc catgatgtgc tcatcggcaa caacctcttt | 780 |
| ggaagaagcg cgctcaagac ggcatcgagg ctcatcacca aggatgagat caagacaagc | 840 |
| ggcagcgaga tcggcaaggt ctacagcttc ctcatcgtgc tgacatcatt gcaagccaag | 900 |
| gccttcctca ccttgacaac ctgccgcaag ttgctgggcc tctccgacat cgactacacc | 960 |
| tccatcatga atgagcacct caacaatgag aagaatgagt tcagagacaa catcctgccg | 1020 |
| gcgctgagca caagttcag caacccaagc tacgccaaga ccatcggctc agacaactac | 1080 |
| gccaaggtga tcctggagag cgagcctggc tacgcgctgg tgggcttcga gatcatcaat | 1140 |
| gatccaattc ctgttctcaa ggcctacaag gccaagctga agcagaacta ccaggtggac | 1200 |
| aaccagagct tgagcgagat cgtctacctg gacatcgaca gctcttctg cccggagaac | 1260 |
| tcagagcaga agtactacac caagaacctc accttccctg atggatatgt catcaccaag | 1320 |
| atcaccttcg agaagaagct gaacaacctc atctacgagg ccaccgccaa cttctatgat | 1380 |
| ccatcaacag gagacatcga cctcaacaag aagcaagtgg agagcacctt ccctcaaaca | 1440 |

```
gactacatca ccatggacat tggagatgat gatggcatct acatgccgct cggcgtcatc    1500
tcagaaacct tcttgacgcc catcaacagc ttcggcctgg aggtggacgc caagagcaag    1560
accttgacgc tcaagtgcaa gagctacctc agggagtacc tgctggagag tgatttgaag    1620
aacaaggaga cagggctgat cgcgccgcca aatgtgttca tcagcaatgt ggtgaagaac    1680
tgggacatcg aggaggattc attggagcca tgggtggcca acaacaagaa tgcttatgtg    1740
gacaacaccg gcggcattga agaagcaag gcgctcttca cccaaggaga tggagagttc    1800
agccagttca tcggcgacaa gctaaagccc aacaccgact acatcatcca gtacaccgtc    1860
aagggcaagc cggccatcta cctcaagaac aagagcaccg gctacatcac ctacgaggac    1920
accaatggaa attctgagga gttccaaaca attgctgtga gttcacctc agaaacagat     1980 ttgagccaga cccacctggt gttcaagagc caaaatggat atgaagcatg gggagacaac    2040
ttcatcatcc tggaggccaa gctcttcgag acaccagaaa gcccggagct catcaagttc    2100
aatgattggg agaggttcgg caccacctac atcaccggca tgagctgag gattgatcat     2160 tcaagaggag gctacttccg ccaaagcctc aacatcgaca gctacagcac ctacgacctc    2220
agcttcagct tcagcggcct ctgggccaag gtgattgtga gaacagccg cggcgtggtg     2280 ctcttcgaga aggtgaagaa caatggaagc agctatgagg acatctcaga gcacttcacc    2340
acctggggct ataaggatgg cttctttatc gagctcaccg ccgagaggac aagcagcacc    2400
ttccacagct tcagagacat cagcatcaag gagaagattg aa                       2442
```

<210> SEQ ID NO 37
<211> LENGTH: 814
<212> TYPE: PRT
<213> ORGANISM: Artificial
<220> FEATURE:
<223> OTHER INFORMATION: Axmi115 variant sequence

<400> SEQUENCE: 37

```
Met Ala His His His His His Gly Ser Thr Met Asn Met Asn Asn
1               5                   10                  15

Thr Lys Leu Asn Ala Arg Ala Leu Pro Ser Phe Ile Asp Tyr Phe Asn
            20                  25                  30

Gly Ile Tyr Gly Phe Ala Thr Gly Ile Lys Asp Ile Met Asn Met Ile
        35                  40                  45

Phe Lys Thr Asp Thr Gly Gly Asn Leu Thr Leu Asp Glu Ile Leu Lys
    50                  55                  60

Asn Gln Gln Leu Leu Asn Glu Ile Ser Gly Lys Leu Asp Gly Val Asn
65                  70                  75                  80

Gly Ser Leu Asn Asp Leu Ile Ala Gln Gly Asn Leu Asn Thr Glu Leu
                85                  90                  95

Ser Lys Glu Ile Leu Lys Ile Ala Asn Glu Gln Asn Gln Val Leu Asn
            100                 105                 110

Asp Val Asn Asn Lys Leu Asp Ala Ile Asn Thr Met Leu His Ile Tyr
        115                 120                 125

Leu Pro Lys Ile Thr Ser Met Leu Ser Asp Val Met Lys Gln Asn Tyr
    130                 135                 140

Ala Leu Ser Leu Gln Ile Glu Tyr Leu Ser Lys Gln Leu Gln Glu Ile
145                 150                 155                 160

Ser Asp Lys Leu Asp Ile Ile Asn Val Asn Val Leu Ile Asn Ser Thr
                165                 170                 175

Leu Thr Glu Ile Thr Pro Ala Tyr Gln Arg Ile Lys Tyr Val Asn Glu
            180                 185                 190
```

```
Lys Phe Asp Lys Leu Thr Phe Ala Thr Glu Ser Thr Leu Arg Ala Lys
            195                 200                 205

Gln Gly Ile Phe Asn Glu Asp Ser Phe Asp Asn Asn Thr Leu Glu Asn
    210                 215                 220

Leu Thr Asp Leu Ala Glu Leu Ala Lys Ser Ile Thr Lys Asn Asp Val
225                 230                 235                 240

Asp Ser Phe Glu Phe Tyr Leu His Thr Phe His Asp Val Leu Ile Gly
                245                 250                 255

Asn Asn Leu Phe Gly Arg Ser Ala Leu Lys Thr Ala Ser Glu Leu Ile
            260                 265                 270

Thr Lys Asp Glu Ile Lys Thr Ser Gly Ser Glu Ile Gly Lys Val Tyr
        275                 280                 285

Ser Phe Leu Ile Val Leu Thr Ser Leu Gln Ala Lys Ala Phe Leu Thr
    290                 295                 300

Leu Thr Thr Cys Arg Lys Leu Leu Gly Leu Ser Asp Ile Asp Tyr Thr
305                 310                 315                 320

Ser Ile Met Asn Glu His Leu Asn Asn Glu Lys Asn Glu Phe Arg Asp
                325                 330                 335

Asn Ile Leu Pro Ala Leu Ser Asn Lys Phe Ser Asn Pro Ser Tyr Ala
            340                 345                 350

Lys Thr Ile Gly Ser Asp Asn Tyr Ala Lys Val Ile Leu Glu Ser Glu
        355                 360                 365

Pro Gly Tyr Ala Leu Val Gly Phe Glu Ile Ile Asn Asp Pro Ile Pro
    370                 375                 380

Val Leu Lys Ala Tyr Lys Ala Lys Leu Lys Gln Asn Tyr Gln Val Asp
385                 390                 395                 400

Asn Gln Ser Leu Ser Glu Ile Val Tyr Leu Asp Ile Asp Lys Leu Phe
                405                 410                 415

Cys Pro Glu Asn Ser Glu Gln Lys Tyr Tyr Thr Lys Asn Leu Thr Phe
            420                 425                 430

Pro Asp Gly Tyr Val Ile Thr Lys Ile Thr Phe Glu Lys Lys Leu Asn
    435                 440                 445

Asn Leu Ile Tyr Glu Ala Thr Ala Asn Phe Tyr Asp Pro Ser Thr Gly
450                 455                 460

Asp Ile Asp Leu Asn Lys Lys Gln Val Glu Ser Thr Phe Pro Gln Thr
465                 470                 475                 480

Asp Tyr Ile Thr Met Asp Ile Gly Asp Asp Asp Gly Ile Tyr Met Pro
                485                 490                 495

Leu Gly Val Ile Ser Glu Thr Phe Leu Thr Pro Ile Asn Ser Phe Gly
            500                 505                 510

Leu Glu Val Asp Ala Lys Ser Lys Thr Leu Thr Leu Lys Cys Lys Ser
        515                 520                 525

Tyr Leu Arg Glu Tyr Leu Leu Glu Ser Asp Leu Lys Asn Lys Glu Thr
    530                 535                 540

Gly Leu Ile Ala Pro Pro Asn Val Phe Ile Ser Asn Val Val Lys Asn
545                 550                 555                 560

Trp Asp Ile Glu Glu Asp Ser Leu Glu Pro Trp Val Ala Asn Asn Lys
                565                 570                 575

Asn Ala Tyr Val Asp Asn Thr Gly Gly Ile Glu Arg Ser Lys Ala Leu
            580                 585                 590

Phe Thr Gln Gly Asp Gly Glu Phe Ser Gln Phe Ile Gly Asp Lys Leu
        595                 600                 605
```

-continued

```
Lys Pro Asn Thr Asp Tyr Ile Ile Gln Tyr Thr Val Lys Gly Lys Pro
610                 615                 620

Ala Ile Tyr Leu Lys Asn Lys Ser Thr Gly Tyr Ile Thr Tyr Glu Asp
625                 630                 635                 640

Thr Asn Gly Asn Ser Glu Glu Phe Gln Thr Ile Ala Val Lys Phe Thr
            645                 650                 655

Ser Glu Thr Asp Leu Ser Gln Thr His Leu Val Phe Lys Ser Gln Asn
            660                 665                 670

Gly Tyr Glu Ala Trp Gly Asp Asn Phe Ile Ile Leu Glu Ala Lys Leu
                675                 680                 685

Phe Glu Thr Pro Glu Ser Pro Glu Leu Ile Lys Phe Asn Asp Trp Glu
690                 695                 700

Arg Phe Gly Thr Thr Tyr Ile Thr Gly Asn Glu Leu Arg Ile Asp His
705                 710                 715                 720

Ser Arg Gly Gly Tyr Phe Arg Gln Ser Leu Asn Ile Asp Ser Tyr Ser
            725                 730                 735

Thr Tyr Asp Leu Ser Phe Ser Phe Ser Gly Leu Trp Ala Lys Val Ile
            740                 745                 750

Val Lys Asn Ser Arg Gly Val Val Leu Phe Glu Lys Val Lys Asn Asn
        755                 760                 765

Gly Ser Ser Tyr Glu Asp Ile Ser Glu Ser Phe Thr Thr Ala Ser Asn
770                 775                 780

Lys Asp Gly Phe Phe Ile Glu Leu Thr Ala Glu Arg Thr Ser Ser Thr
785                 790                 795                 800

Phe His Ser Phe Arg Asp Ile Ser Ile Lys Glu Lys Ile Glu
            805                 810
```

<210> SEQ ID NO 38
<211> LENGTH: 809
<212> TYPE: PRT
<213> ORGANISM: Artificial
<220> FEATURE:
<223> OTHER INFORMATION: Axmi115 variant sequence

<400> SEQUENCE: 38

```
Met Ala His His His His His His Gly Ser Thr Met Asn Met Asn Asn
1               5                   10                  15

Thr Lys Leu Asn Ala Arg Ala Leu Pro Ser Phe Ile Asp Tyr Phe Asn
            20                  25                  30

Gly Ile Tyr Gly Phe Ala Thr Gly Ile Lys Asp Ile Met Asn Met Ile
        35                  40                  45

Phe Lys Thr Asp Thr Gly Gly Asn Leu Thr Leu Asp Glu Ile Leu Lys
50                  55                  60

Asn Gln Gln Leu Leu Asn Glu Ile Ser Gly Lys Leu Asp Gly Val Asn
65                  70                  75                  80

Gly Ser Leu Asn Asp Leu Ile Ala Gln Gly Asn Leu Asn Thr Glu Leu
                85                  90                  95

Ser Lys Glu Ile Leu Lys Ile Ala Asn Glu Gln Asn Gln Val Leu Asn
            100                 105                 110

Asp Val Asn Asn Lys Leu Asp Ala Ile Asn Thr Met Leu His Ile Tyr
        115                 120                 125

Leu Pro Lys Ile Thr Ser Met Leu Ser Asp Val Met Lys Gln Asn Tyr
130                 135                 140

Ala Leu Ser Leu Gln Ile Glu Tyr Leu Ser Lys Gln Leu Gln Glu Ile
145                 150                 155                 160
```

```
Ser Asp Lys Leu Asp Ile Ile Asn Val Asn Val Leu Ile Asn Ser Thr
            165                 170                 175

Leu Thr Glu Ile Thr Pro Ala Tyr Gln Arg Ile Lys Tyr Val Asn Glu
            180                 185                 190

Lys Phe Glu Glu Leu Thr Phe Ala Thr Glu Thr Thr Leu Lys Val Lys
            195                 200                 205

Lys Asp Ser Ser Pro Ala Asp Ile Leu Asp Glu Leu Thr Glu Leu Thr
            210                 215                 220

Glu Leu Ala Lys Ser Val Thr Lys Asn Asp Val Asp Gly Phe Glu Phe
225                 230                 235                 240

Tyr Leu Asn Thr Phe His Asp Val Met Val Gly Asn Asn Leu Phe Gly
            245                 250                 255

Arg Ser Ala Leu Lys Thr Ala Ser Glu Leu Ile Ala Lys Glu Asn Val
            260                 265                 270

Lys Thr Ser Gly Ser Glu Val Gly Asn Val Tyr Asn Phe Leu Ile Val
            275                 280                 285

Leu Thr Ala Leu Gln Ala Lys Ala Phe Leu Thr Leu Thr Cys Arg
            290                 295                 300

Lys Leu Leu Gly Leu Ser Asp Ile Asp Tyr Thr Ser Ile Met Asn Glu
305                 310                 315                 320

His Leu Asn Asn Glu Lys Asn Glu Phe Arg Asp Asn Ile Leu Pro Ala
            325                 330                 335

Leu Ser Asn Lys Phe Ser Asn Pro Ser Tyr Ala Lys Thr Ile Gly Ser
            340                 345                 350

Asp Asn Tyr Ala Lys Val Ile Leu Glu Ser Glu Pro Gly Tyr Ala Leu
            355                 360                 365

Val Gly Phe Glu Ile Ile Asn Asp Pro Ile Pro Val Leu Lys Ala Tyr
            370                 375                 380

Lys Ala Lys Leu Lys Gln Asn Tyr Gln Val Asp Asn Gln Ser Leu Ser
385                 390                 395                 400

Glu Ile Val Tyr Leu Asp Ile Asp Lys Leu Phe Cys Pro Glu Asn Ser
            405                 410                 415

Glu Gln Lys Tyr Tyr Thr Lys Asn Leu Thr Phe Pro Asp Gly Tyr Val
            420                 425                 430

Ile Thr Lys Ile Thr Phe Glu Lys Lys Leu Asn Asn Leu Ile Tyr Glu
            435                 440                 445

Ala Thr Ala Asn Phe Tyr Asp Pro Ser Thr Gly Asp Ile Asp Leu Asn
450                 455                 460

Lys Lys Gln Val Glu Ser Thr Phe Pro Gln Thr Asp Tyr Ile Thr Met
465                 470                 475                 480

Asp Ile Gly Asp Asp Gly Ile Tyr Met Pro Leu Gly Val Ile Ser
            485                 490                 495

Glu Thr Phe Leu Thr Pro Ile Asn Ser Phe Gly Leu Glu Val Asp Ala
            500                 505                 510

Lys Ser Lys Thr Leu Thr Leu Lys Cys Lys Ser Tyr Leu Arg Glu Tyr
            515                 520                 525

Leu Leu Glu Ser Asp Leu Lys Asn Lys Glu Thr Gly Leu Ile Ala Pro
            530                 535                 540

Pro Asn Val Phe Ile Ser Asn Val Val Lys Asn Trp Asp Ile Glu Glu
545                 550                 555                 560

Asp Ser Leu Glu Pro Trp Val Ala Asn Asn Lys Asn Ala Tyr Val Asp
            565                 570                 575

Asn Thr Gly Gly Ile Glu Arg Ser Lys Ala Leu Phe Thr Gln Gly Asp
```

```
                    580                 585                 590
Gly Glu Phe Ser Gln Phe Ile Gly Asp Lys Leu Lys Pro Asn Thr Asp
            595                 600                 605

Tyr Ile Ile Gln Tyr Thr Val Lys Gly Lys Pro Ala Ile Tyr Leu Lys
            610                 615                 620

Asn Lys Ser Thr Gly Tyr Ile Thr Tyr Glu Asp Thr Asn Gly Asn Ser
625                 630                 635                 640

Glu Glu Phe Gln Thr Ile Ala Val Lys Phe Thr Ser Glu Thr Asp Leu
                645                 650                 655

Ser Gln Thr His Leu Val Phe Lys Ser Gln Asn Gly Tyr Glu Ala Trp
                660                 665                 670

Gly Asp Asn Phe Ile Ile Leu Glu Ala Lys Leu Phe Glu Thr Pro Glu
                675                 680                 685

Ser Pro Glu Leu Ile Lys Phe Asn Asp Trp Glu Arg Phe Gly Thr Thr
            690                 695                 700

Tyr Ile Thr Gly Asn Glu Leu Arg Ile Asp His Ser Arg Gly Gly Tyr
705                 710                 715                 720

Phe Arg Gln Ser Leu Asn Ile Asp Ser Tyr Ser Thr Tyr Asp Leu Ser
                725                 730                 735

Phe Ser Phe Ser Gly Leu Trp Ala Lys Val Ile Val Lys Asn Ser Arg
                740                 745                 750

Gly Val Val Leu Phe Glu Lys Val Lys Asn Asn Gly Ser Ser Tyr Glu
            755                 760                 765

Asp Ile Ser Glu Ser Phe Thr Thr Ala Ser Asn Lys Asp Gly Phe Phe
            770                 775                 780

Ile Glu Leu Thr Ala Glu Arg Thr Ser Ser Thr Phe His Ser Phe Arg
785                 790                 795                 800

Asp Ile Ser Ile Lys Glu Lys Ile Glu
                805

<210> SEQ ID NO 39
<211> LENGTH: 806
<212> TYPE: PRT
<213> ORGANISM: Artificial
<220> FEATURE:
<223> OTHER INFORMATION: Axmi115 variant sequence

<400> SEQUENCE: 39

Met Ala His His His His His His Gly Ser Thr Met Asn Met Asn Asn
1               5                   10                  15

Thr Lys Leu Asn Ala Arg Ala Leu Pro Ser Phe Ile Asp Tyr Phe Asn
            20                  25                  30

Gly Ile Tyr Gly Phe Ala Thr Gly Ile Lys Asp Ile Met Asn Met Ile
            35                  40                  45

Phe Lys Thr Asp Thr Gly Gly Asn Leu Thr Leu Asp Glu Ile Leu Lys
        50                  55                  60

Asn Gln Gln Leu Leu Asn Glu Ile Ser Gly Lys Leu Asp Gly Val Asn
65                  70                  75                  80

Gly Ser Leu Asn Asp Leu Ile Ala Gln Gly Asn Leu Asn Thr Glu Leu
                85                  90                  95

Ser Lys Glu Ile Leu Lys Ile Ala Glu Gln Asn Gln Val Leu Asn
                100                 105                 110

Asp Val Asn Asn Lys Leu Asp Ala Ile Asn Thr Met Leu His Ile Tyr
            115                 120                 125

Leu Pro Lys Ile Thr Ser Met Leu Ser Asp Val Met Lys Gln Asn Tyr
```

```
            130                 135                 140
Ala Leu Ser Leu Gln Ile Glu Tyr Leu Ser Lys Gln Leu Gln Glu Ile
145                 150                 155                 160

Ser Asp Lys Leu Asp Ile Ile Asn Val Asn Val Leu Ile Asn Ser Thr
                165                 170                 175

Leu Thr Glu Ile Thr Pro Ala Tyr Gln Arg Ile Lys Tyr Val Asn Glu
            180                 185                 190

Lys Phe Glu Glu Leu Thr Phe Ala Thr Glu Thr Thr Leu Lys Val Lys
        195                 200                 205

Lys Asp Ser Ser Pro Ala Asp Ile Leu Asp Glu Leu Thr Glu Leu Thr
    210                 215                 220

Glu Leu Ala Lys Ser Val Thr Lys Asn Asp Val Asp Gly Phe Glu Phe
225                 230                 235                 240

Tyr Leu Asn Thr Phe His Asp Val Met Val Gly Asn Asn Leu Phe Gly
                245                 250                 255

Arg Ser Ala Leu Lys Thr Ala Ser Glu Leu Ile Ala Lys Glu Asn Val
            260                 265                 270

Lys Thr Ser Gly Ser Glu Val Gly Asn Val Tyr Asn Phe Leu Ile Val
        275                 280                 285

Leu Thr Ala Leu Gln Ala Lys Ala Phe Leu Thr Leu Thr Thr Cys Arg
    290                 295                 300

Lys Leu Leu Gly Leu Ala Asp Ile Asp Tyr Thr Ser Ile Met Asn Glu
305                 310                 315                 320

His Leu Asn Lys Glu Lys Glu Glu Phe Arg Val Asn Ile Leu Pro Thr
                325                 330                 335

Leu Ser Asn Thr Phe Ser Asn Pro Asn Tyr Ala Lys Val Lys Gly Ser
            340                 345                 350

Asp Glu Asp Ala Lys Met Ile Val Glu Ala Lys Pro Gly His Ala Leu
        355                 360                 365

Val Gly Phe Glu Met Ser Asn Asp Ser Ile Thr Val Leu Lys Val Tyr
    370                 375                 380

Glu Ala Lys Leu Lys Gln Asn Tyr Gln Val Asp Lys Asp Ser Leu Ser
385                 390                 395                 400

Glu Val Ile Tyr Gly Asp Met Asp Lys Leu Leu Cys Pro Asp Gln Ser
                405                 410                 415

Glu Gln Ile Tyr Tyr Thr Asn Asn Ile Val Phe Pro Asn Glu Tyr Val
            420                 425                 430

Ile Thr Lys Ile Asp Phe Thr Lys Lys Met Lys Thr Leu Arg Tyr Glu
        435                 440                 445

Val Thr Ala Asn Ser Tyr Asp Ser Ser Thr Gly Glu Ile Asp Leu Asn
    450                 455                 460

Lys Lys Lys Val Glu Ser Ser Glu Ala Glu Tyr Arg Thr Leu Ser Ala
465                 470                 475                 480

Lys Asp Asp Gly Val Tyr Met Pro Leu Gly Val Ile Ser Glu Thr Phe
                485                 490                 495

Leu Thr Pro Ile Asn Gly Phe Gly Leu Gln Ala Asp Glu Asn Ser Arg
            500                 505                 510

Leu Ile Thr Leu Thr Cys Lys Ser Tyr Leu Arg Glu Leu Leu Leu Ala
        515                 520                 525

Thr Asp Leu Ser Asn Lys Glu Thr Lys Leu Ile Val Pro Pro Ser Gly
    530                 535                 540

Phe Ile Ser Asn Ile Val Glu Asn Gly Asn Leu Glu Gly Glu Asn Leu
545                 550                 555                 560
```

-continued

```
Glu Pro Trp Ile Ala Asn Asn Lys Asn Ala Tyr Val Asp His Thr Gly
                565                 570                 575
Gly Val Asn Gly Thr Arg Ala Leu Tyr Val His Lys Asp Gly Gly Phe
            580                 585                 590
Ser Gln Phe Ile Gly Asp Lys Leu Lys Pro Lys Thr Glu Tyr Val Ile
        595                 600                 605
Gln Tyr Thr Val Lys Gly Lys Pro Ala Ile Tyr Leu Lys Asn Lys Ser
    610                 615                 620
Thr Gly Tyr Ile Thr Tyr Glu Asp Thr Asn Gly Asn Ser Glu Glu Phe
625                 630                 635                 640
Gln Thr Ile Ala Val Lys Phe Thr Ser Glu Thr Asp Leu Ser Gln Thr
                645                 650                 655
His Leu Val Phe Lys Ser Gln Asn Gly Tyr Glu Ala Trp Gly Asp Asn
            660                 665                 670
Phe Ile Ile Leu Glu Ala Lys Leu Phe Glu Thr Pro Glu Ser Pro Glu
        675                 680                 685
Leu Ile Lys Phe Asn Asp Trp Glu Arg Phe Gly Thr Thr Tyr Ile Thr
    690                 695                 700
Gly Asn Glu Leu Arg Ile Asp His Ser Arg Gly Gly Tyr Phe Arg Gln
705                 710                 715                 720
Ser Leu Asn Ile Asp Ser Tyr Ser Thr Tyr Asp Leu Ser Phe Ser Phe
                725                 730                 735
Ser Gly Leu Trp Ala Lys Val Ile Val Lys Asn Ser Arg Gly Val Val
            740                 745                 750
Leu Phe Glu Lys Val Lys Asn Asn Gly Ser Ser Tyr Glu Asp Ile Ser
        755                 760                 765
Glu Ser Phe Thr Thr Ala Ser Asn Lys Asp Gly Phe Phe Ile Glu Leu
    770                 775                 780
Thr Ala Glu Arg Thr Ser Ser Thr Phe His Ser Phe Arg Asp Ile Ser
785                 790                 795                 800
Ile Lys Glu Lys Ile Glu
                805
```

<210> SEQ ID NO 40
<211> LENGTH: 814
<212> TYPE: PRT
<213> ORGANISM: Artificial
<220> FEATURE:
<223> OTHER INFORMATION: Axmi115 variant sequence

<400> SEQUENCE: 40

```
Met Ala His His His His His His Gly Ser Thr Met Asn Met Asn Asn
1               5                   10                  15
Thr Lys Leu Asn Ala Arg Ala Leu Pro Ser Phe Ile Asp Tyr Phe Asn
                20                  25                  30
Gly Ile Tyr Gly Phe Ala Thr Gly Ile Lys Asp Ile Met Asn Met Ile
            35                  40                  45
Phe Lys Thr Asp Thr Gly Gly Asn Leu Thr Leu Asp Glu Ile Leu Lys
        50                  55                  60
Asn Gln Gln Leu Leu Asn Glu Ile Ser Gly Lys Leu Asp Gly Val Asn
65                  70                  75                  80
Gly Ser Leu Asn Asp Leu Ile Ala Gln Gly Asn Leu Asn Thr Glu Leu
                85                  90                  95
Ser Lys Glu Ile Leu Lys Ile Ala Asn Glu Gln Asn Gln Val Leu Asn
                100                 105                 110
```

-continued

```
Asp Val Asn Asn Lys Leu Asp Ala Ile Asn Thr Met Leu His Ile Tyr
            115                 120                 125

Leu Pro Lys Ile Thr Ser Met Leu Ser Asp Val Met Lys Gln Asn Tyr
    130                 135                 140

Ala Leu Ser Leu Gln Ile Glu Tyr Leu Ser Lys Gln Leu Gln Glu Ile
145                 150                 155                 160

Ser Asp Lys Leu Asp Ile Ile Asn Val Asn Val Leu Ile Asn Ser Thr
                165                 170                 175

Leu Thr Glu Ile Thr Pro Ala Tyr Gln Arg Ile Lys Tyr Val Asn Glu
            180                 185                 190

Lys Phe Asp Lys Leu Thr Phe Ala Thr Glu Ser Thr Leu Arg Ala Lys
    195                 200                 205

Gln Gly Ile Phe Asn Glu Asp Ser Phe Asp Asn Asn Thr Leu Glu Asn
210                 215                 220

Leu Thr Asp Leu Ala Glu Leu Ala Lys Ser Ile Thr Lys Asn Asp Val
225                 230                 235                 240

Asp Ser Phe Glu Phe Tyr Leu His Thr Phe His Asp Val Leu Ile Gly
                245                 250                 255

Asn Asn Leu Phe Gly Arg Ser Ala Leu Lys Thr Ala Ser Glu Leu Ile
            260                 265                 270

Thr Lys Asp Glu Ile Lys Thr Ser Gly Ser Glu Ile Gly Lys Val Tyr
    275                 280                 285

Ser Phe Leu Ile Val Leu Thr Ser Leu Gln Ala Lys Ala Phe Leu Thr
290                 295                 300

Leu Thr Thr Cys Arg Lys Leu Leu Gly Leu Ser Asp Ile Asp Tyr Thr
305                 310                 315                 320

Ser Ile Met Asn Glu His Leu Asn Asn Glu Lys Asn Glu Phe Arg Asp
                325                 330                 335

Asn Ile Leu Pro Ala Leu Ser Asn Lys Phe Ser Asn Pro Ser Tyr Ala
            340                 345                 350

Lys Thr Ile Gly Ser Asp Asn Tyr Ala Lys Val Ile Leu Glu Ser Glu
    355                 360                 365

Pro Gly Tyr Ala Leu Val Gly Phe Glu Ile Ile Asn Asp Pro Ile Pro
370                 375                 380

Val Leu Lys Ala Tyr Lys Ala Lys Leu Lys Gln Asn Tyr Gln Val Asp
385                 390                 395                 400

Asn Gln Ser Leu Ser Glu Ile Val Tyr Leu Asp Ile Asp Lys Leu Phe
                405                 410                 415

Cys Pro Glu Asn Ser Glu Gln Lys Tyr Tyr Thr Lys Asn Leu Thr Phe
            420                 425                 430

Pro Asp Gly Tyr Val Ile Thr Lys Ile Thr Phe Glu Lys Lys Leu Asn
    435                 440                 445

Asn Leu Ile Tyr Glu Ala Thr Ala Asn Phe Tyr Asp Pro Ser Thr Gly
450                 455                 460

Asp Ile Asp Leu Asn Lys Lys Gln Val Glu Ser Thr Phe Pro Gln Thr
465                 470                 475                 480

Asp Tyr Ile Thr Met Asp Ile Gly Asp Asp Gly Ile Tyr Met Pro
                485                 490                 495

Leu Gly Val Ile Ser Glu Thr Phe Leu Thr Pro Ile Asn Ser Phe Gly
            500                 505                 510

Leu Glu Val Asp Ala Lys Ser Lys Thr Leu Thr Leu Lys Cys Lys Ser
    515                 520                 525
```

```
Tyr Leu Arg Glu Tyr Leu Leu Glu Ser Asp Leu Lys Asn Lys Glu Thr
            530                 535                 540

Gly Leu Ile Ala Pro Pro Asn Val Phe Ile Ser Asn Val Val Lys Asn
545                 550                 555                 560

Trp Asp Ile Glu Glu Asp Ser Leu Glu Pro Trp Val Ala Asn Asn Lys
                565                 570                 575

Asn Ala Tyr Val Asp Asn Thr Gly Gly Ile Glu Arg Ser Lys Ala Leu
            580                 585                 590

Phe Thr Gln Gly Asp Gly Glu Phe Ser Gln Phe Ile Gly Asp Lys Leu
        595                 600                 605

Lys Pro Asn Thr Asp Tyr Ile Ile Gln Tyr Thr Val Lys Gly Lys Pro
610                 615                 620

Ala Ile Tyr Leu Lys Asn Lys Ser Thr Gly Tyr Ile Thr Tyr Glu Asp
625                 630                 635                 640

Thr Asn Gly Asn Ser Glu Glu Phe Gln Thr Ile Ala Val Lys Phe Thr
                645                 650                 655

Ser Glu Thr Asp Leu Ser Gln Thr His Leu Val Phe Lys Ser Gln Asn
            660                 665                 670

Gly Tyr Glu Ala Trp Gly Asp Asn Phe Ile Ile Leu Glu Ala Lys Leu
        675                 680                 685

Phe Glu Thr Pro Glu Ser Pro Glu Leu Ile Lys Phe Asn Asp Trp Glu
690                 695                 700

Arg Phe Gly Thr Thr Tyr Ile Thr Gly Asn Glu Leu Arg Ile Asp His
705                 710                 715                 720

Ser Arg Gly Gly Tyr Phe Arg Gln Ser Leu Asn Ile Asp Ser Tyr Ser
                725                 730                 735

Thr Tyr Asp Leu Ser Phe Ser Phe Ser Gly Leu Trp Ala Lys Val Ile
            740                 745                 750

Val Lys Asn Ser Arg Gly Val Val Leu Phe Glu Lys Val Lys Asn Asn
        755                 760                 765

Gly Ser Ser Tyr Glu Asp Ile Ser Glu Asp Phe Thr Thr Asn Gly Phe
770                 775                 780

Lys Asp Gly Phe Tyr Ile Glu Leu Thr Ala Glu Arg Thr Ser Ser Thr
785                 790                 795                 800

Phe His Ser Phe Arg Asp Ile Ser Ile Lys Glu Lys Ile Glu
                805                 810
```

<210> SEQ ID NO 41
<211> LENGTH: 814
<212> TYPE: PRT
<213> ORGANISM: Artificial
<220> FEATURE:
<223> OTHER INFORMATION: Axmi115 variant sequence

<400> SEQUENCE: 41

```
Met Ala His His His His His His Gly Ser Thr Met Asn Met Asn Asn
1               5                   10                  15

Thr Lys Leu Asn Ala Arg Ala Leu Pro Ser Phe Ile Asp Tyr Phe Asn
            20                  25                  30

Gly Ile Tyr Gly Phe Ala Thr Gly Ile Lys Asp Ile Met Asn Met Ile
        35                  40                  45

Phe Lys Thr Asp Thr Gly Gly Asn Leu Thr Leu Asp Glu Ile Leu Lys
    50                  55                  60

Asn Gln Gln Leu Leu Asn Glu Ile Ser Gly Lys Leu Asp Gly Val Asn
65                  70                  75                  80
```

Gly Ser Leu Asn Asp Leu Ile Ala Gln Gly Asn Leu Asn Thr Glu Leu
                85                  90                  95

Ser Lys Glu Ile Leu Lys Ile Ala Asn Glu Gln Asn Gln Val Leu Asn
            100                 105                 110

Asp Val Asn Asn Lys Leu Asp Ala Ile Asn Thr Met Leu His Ile Tyr
            115                 120                 125

Leu Pro Lys Ile Thr Ser Met Leu Ser Asp Val Met Lys Gln Asn Tyr
            130                 135                 140

Ala Leu Ser Leu Gln Ile Glu Tyr Leu Ser Lys Gln Leu Gln Glu Ile
145                 150                 155                 160

Ser Asp Lys Leu Asp Ile Ile Asn Val Asn Val Leu Ile Asn Ser Thr
            165                 170                 175

Leu Thr Glu Ile Thr Pro Ala Tyr Gln Arg Ile Lys Tyr Val Asn Glu
            180                 185                 190

Lys Phe Asp Lys Leu Thr Phe Ala Thr Glu Ser Thr Leu Arg Ala Lys
            195                 200                 205

Gln Gly Ile Phe Asn Glu Asp Ser Phe Asp Asn Thr Leu Glu Asn
            210                 215                 220

Leu Thr Asp Leu Ala Glu Leu Ala Lys Ser Ile Thr Lys Asn Asp Val
225                 230                 235                 240

Asp Ser Phe Glu Phe Tyr Leu His Thr Phe His Asp Val Leu Ile Gly
            245                 250                 255

Asn Asn Leu Phe Gly Arg Ser Ala Leu Lys Thr Ala Ser Glu Leu Ile
            260                 265                 270

Thr Lys Asp Glu Ile Lys Thr Ser Gly Ser Glu Ile Gly Lys Val Tyr
            275                 280                 285

Ser Phe Leu Ile Val Leu Thr Ser Leu Gln Ala Lys Ala Phe Leu Thr
            290                 295                 300

Leu Thr Thr Cys Arg Lys Leu Leu Gly Leu Ser Asp Ile Asp Tyr Thr
305                 310                 315                 320

Ser Ile Met Asn Glu His Leu Asn Asn Glu Lys Asn Glu Phe Arg Asp
            325                 330                 335

Asn Ile Leu Pro Ala Leu Ser Asn Lys Phe Ser Asn Pro Ser Tyr Ala
            340                 345                 350

Lys Thr Ile Gly Ser Asp Asn Tyr Ala Lys Val Ile Leu Glu Ser Glu
            355                 360                 365

Pro Gly Tyr Ala Leu Val Gly Phe Glu Ile Ile Asn Asp Pro Ile Pro
            370                 375                 380

Val Leu Lys Ala Tyr Lys Ala Lys Leu Lys Gln Asn Tyr Gln Val Asp
385                 390                 395                 400

Asn Gln Ser Leu Ser Glu Ile Val Tyr Leu Asp Ile Asp Lys Leu Phe
            405                 410                 415

Cys Pro Glu Asn Ser Glu Gln Lys Tyr Tyr Thr Lys Asn Leu Thr Phe
            420                 425                 430

Pro Asp Gly Tyr Val Ile Thr Lys Ile Thr Phe Glu Lys Lys Leu Asn
            435                 440                 445

Asn Leu Ile Tyr Glu Ala Thr Ala Asn Phe Tyr Asp Pro Ser Thr Gly
            450                 455                 460

Asp Ile Asp Leu Asn Lys Lys Gln Val Glu Ser Thr Phe Pro Gln Thr
465                 470                 475                 480

Asp Tyr Ile Thr Met Asp Ile Gly Asp Asp Gly Ile Tyr Met Pro
            485                 490                 495

Leu Gly Val Ile Ser Glu Thr Phe Leu Thr Pro Ile Asn Ser Phe Gly

```
                500               505               510
Leu Glu Val Asp Ala Lys Ser Lys Thr Leu Thr Leu Lys Cys Lys Ser
            515                   520                   525
Tyr Leu Arg Glu Tyr Leu Leu Glu Ser Asp Leu Lys Asn Lys Glu Thr
        530                   535                   540
Gly Leu Ile Ala Pro Pro Asn Val Phe Ile Ser Asn Val Val Lys Asn
545                   550                   555                   560
Trp Asp Ile Glu Glu Asp Ser Leu Glu Pro Trp Val Ala Asn Asn Lys
                565                   570                   575
Asn Ala Tyr Val Asp Asn Thr Gly Gly Ile Glu Arg Ser Lys Ala Leu
            580                   585                   590
Phe Thr Gln Gly Asp Gly Glu Phe Ser Gln Phe Ile Gly Asp Lys Leu
        595                   600                   605
Lys Pro Asn Thr Asp Tyr Ile Ile Gln Tyr Thr Val Lys Gly Lys Pro
610                   615                   620
Ala Ile Tyr Leu Lys Asn Lys Ser Thr Gly Tyr Ile Thr Tyr Glu Asp
625                   630                   635                   640
Thr Asn Gly Asn Ser Glu Glu Phe Gln Thr Ile Ala Val Lys Phe Thr
                645                   650                   655
Ser Glu Thr Asp Leu Ser Gln Thr His Leu Val Phe Lys Ser Gln Asn
            660                   665                   670
Gly Tyr Glu Ala Trp Gly Asp Asn Phe Ile Ile Leu Glu Ala Lys Leu
        675                   680                   685
Phe Glu Thr Pro Glu Ser Pro Glu Leu Ile Lys Phe Asn Asp Trp Glu
        690                   695                   700
Arg Phe Gly Thr Thr Tyr Ile Thr Gly Asn Glu Leu Arg Ile Asp His
705                   710                   715                   720
Ser Arg Gly Gly Tyr Phe Arg Gln Ser Leu Asn Ile Asp Ser Tyr Ser
                725                   730                   735
Thr Tyr Asp Leu Ser Phe Ser Phe Ser Gly Leu Trp Ala Lys Val Ile
            740                   745                   750
Val Lys Asn Ser Arg Gly Val Val Leu Phe Glu Lys Val Lys Asn Asn
        755                   760                   765
Gly Ser Ser Tyr Glu Asp Ile Ser Glu His Phe Thr Thr Trp Gly Tyr
        770                   775                   780
Lys Asp Gly Phe Phe Ile Glu Leu Thr Ala Glu Arg Thr Ser Ser Thr
785                   790                   795                   800
Phe His Ser Phe Arg Asp Ile Ser Ile Lys Glu Lys Ile Glu
                805                   810

<210> SEQ ID NO 42
<211> LENGTH: 2412
<212> TYPE: DNA
<213> ORGANISM: Artificial
<220> FEATURE:
<223> OTHER INFORMATION: Axmi115 optimized sequence

<400> SEQUENCE: 42
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg ccgacctcac cttggatgag atcctcaaga ccagcagct gctgaatgag      180 atctcaggca gctggacgg cgtcaatgga agcctcaacg acctcattgc tcaaggcaac      240
ctcaacaccg agctgagcaa ggagatcctc aagattgcaa atgagcagaa ccaggtgctg      300
```

| | |
|---|---|
| aatgatgtca caacaagct ggacgccatc aacaccatgc tcaacatcta cctgccaaag | 360 |
| atcacctcaa tgctctctga tgtgatgaag cagaactacg cgctgagcct ccagattgag | 420 |
| tacctctcaa ggcagctgca agagatctcc gacaagctgg atgtcatcaa cctcaatgtg | 480 |
| ctcatcaaca gcaccttgac agagatcacg ccaagctacc agaggatcaa gtatgtcaat | 540 |
| gagaagttcg acaagctcac cttcgccacc gagagcaccc tccgcgccaa gcaaggcatc | 600 |
| ttcaatgaag attcatttga caacaacacc ttggagaact tgacagacct cgccgagctg | 660 |
| gccaagagca tcaccaagaa tgatgtggac agcttcgagt tctacctcca caccttccat | 720 |
| gatgtgctca tcggcaacaa cctctttgga agaagcgcgc tcaagacggc atcagagctc | 780 |
| atcaccaagg atgagatcaa gacaagcggc agcgagatcg gcaaggtcta cagcttcctc | 840 |
| atcgtgctga catcattgca agccaaggcc ttcctcacct tgacaacctg ccgcaagttg | 900 |
| ctgggcctct ccgacatcga ctacacctcc atcatgaatg agcacctcaa caatgagaag | 960 |
| aatgagttca gagacaacat cctgccggcg ctgagcaaca agttcagcaa cccaagctac | 1020 |
| gccaagacca tcggctcaga caactacgcc aaggtgatcc tggagagcga gcctggctac | 1080 |
| gcgctggtgg gcttcgagat catcaatgat ccaattcctg ttctcaaggc ctacaaggcc | 1140 |
| aagctgaagc agaactacca ggtggacaac cagagcttga gcgagatcgt ctacctggac | 1200 |
| atcgacaagc tcttctgccc ggagaactca gagcagaagt actacaccaa gaacctcacc | 1260 |
| ttccctgatg gatatgtcat caccaagatc accttcgaga agaagctgaa caacctcatc | 1320 |
| tacgaggcca ccgccaactt ctatgatcca tcaacaggag acatcgacct caacaagaag | 1380 |
| caagtggaga gcaccttccc tcaaacagac tacatcacca tggacattgg agatgatgat | 1440 |
| ggcatctaca tgccgctcgg cgtcatctca gaaaccttct tgacgcccat caacagcttc | 1500 |
| ggcctggagg tggacgccaa gagcaagacc ttgacgctca agtgcaagag ctacctcagg | 1560 |
| gagtacctgc tggagagtga tttgaagaac aaggagacag ggctgatcgc gccgccaaat | 1620 |
| gtgttcatca gcaatgtggt gaagaactgg gacatcgagg aggattcatt ggagccatgg | 1680 |
| gtggccaaca acaagaatgc ttatgtggac aacaccggcg gcattgaaag aagcaaggcg | 1740 |
| ctcttcaccc aaggagatgg agagttcagc cagttcatcg cgacaagct aaagcccaac | 1800 |
| accgactaca tcatccagta caccgtcaag ggcaagccgg ccatctacct caagaacaag | 1860 |
| agcaccggct acatcaccta cgaggacacc aatggaaatt ctgaggagtt ccaaacaatt | 1920 |
| gctgtgaagt tcacctcaga aacagatttg agccagaccc acctggtgtt caagagccaa | 1980 |
| aatggatatg aagcatgggg agacaacttc atcatcctgg aggccaagct cttcgagaca | 2040 |
| ccagaaagcc cggagctcat caagttcaat gattgggaga ggttcggcac cacctacatc | 2100 |
| accggcaatg agctgaggat tgatcattca agaggaggct acttccgcca agcctcaac | 2160 |
| atcgacagct acagcaccta cgacctcagc ttcagcttca gcggcctctg ggccaaggtg | 2220 |
| attgtgaaga acagccgcgg cgtggtgctc ttcgagaagg tgaagaacaa tggaagcagc | 2280 |
| tatgaggaca tctcagagag cttcaccacc gccagcaaca aggatggctt cttcatcgag | 2340 |
| ctcaccgccg agaggacaag cagcaccttc cacagcttca gagacatcag catcaaggag | 2400 |
| aagattgaat aa | 2412 |

<210> SEQ ID NO 43
<211> LENGTH: 803
<212> TYPE: PRT
<213> ORGANISM: Bacillus thuringiensis

<400> SEQUENCE: 43

-continued

```
Met Asn Met Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asp Leu Thr Leu
                35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65              70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu Asn Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Arg
130                 135                 140

Gln Leu Gln Glu Ile Ser Asp Lys Leu Asp Val Ile Asn Leu Asn Val
145                 150                 155                 160

Leu Ile Asn Ser Thr Leu Thr Glu Ile Thr Pro Ser Tyr Gln Arg Ile
                165                 170                 175

Lys Tyr Val Asn Glu Lys Phe Asp Lys Leu Thr Phe Ala Thr Glu Ser
            180                 185                 190

Thr Leu Arg Ala Lys Gln Gly Ile Phe Asn Glu Asp Ser Phe Asp Asn
        195                 200                 205

Asn Thr Leu Glu Asn Leu Thr Asp Leu Ala Glu Leu Ala Lys Ser Ile
210                 215                 220

Thr Lys Asn Asp Val Asp Ser Phe Glu Phe Tyr Leu His Thr Phe His
225                 230                 235                 240

Asp Val Leu Ile Gly Asn Asn Leu Phe Gly Arg Ser Ala Leu Lys Thr
                245                 250                 255

Ala Ser Glu Leu Ile Thr Lys Asp Glu Ile Lys Thr Ser Gly Ser Glu
            260                 265                 270

Ile Gly Lys Val Tyr Ser Phe Leu Ile Val Leu Thr Ser Leu Gln Ala
        275                 280                 285

Lys Ala Phe Leu Thr Leu Thr Thr Cys Arg Lys Leu Leu Gly Leu Ser
290                 295                 300

Asp Ile Asp Tyr Thr Ser Ile Met Asn Glu His Leu Asn Asn Glu Lys
305                 310                 315                 320

Asn Glu Phe Arg Asp Asn Ile Leu Pro Ala Leu Ser Asn Lys Phe Ser
                325                 330                 335

Asn Pro Ser Tyr Ala Lys Thr Ile Gly Ser Asp Asn Tyr Ala Lys Val
            340                 345                 350

Ile Leu Glu Ser Glu Pro Gly Tyr Ala Leu Val Gly Phe Glu Ile Ile
        355                 360                 365

Asn Asp Pro Ile Pro Val Leu Lys Ala Tyr Lys Ala Lys Leu Lys Gln
370                 375                 380

Asn Tyr Gln Val Asp Asn Gln Ser Leu Ser Glu Ile Val Tyr Leu Asp
385                 390                 395                 400

Ile Asp Lys Leu Phe Cys Pro Glu Asn Ser Glu Gln Lys Tyr Tyr Thr
                405                 410                 415
```

```
Lys Asn Leu Thr Phe Pro Asp Gly Tyr Val Ile Thr Lys Ile Thr Phe
                420                 425                 430

Glu Lys Lys Leu Asn Asn Leu Ile Tyr Glu Ala Thr Ala Asn Phe Tyr
            435                 440                 445

Asp Pro Ser Thr Gly Asp Ile Asp Leu Asn Lys Lys Gln Val Glu Ser
        450                 455                 460

Thr Phe Pro Gln Thr Asp Tyr Ile Thr Met Asp Ile Gly Asp Asp Asp
465                 470                 475                 480

Gly Ile Tyr Met Pro Leu Gly Val Ile Ser Glu Thr Phe Leu Thr Pro
                485                 490                 495

Ile Asn Ser Phe Gly Leu Glu Val Asp Ala Lys Ser Lys Thr Leu Thr
            500                 505                 510

Leu Lys Cys Lys Ser Tyr Leu Arg Glu Tyr Leu Leu Glu Ser Asp Leu
        515                 520                 525

Lys Asn Lys Glu Thr Gly Leu Ile Ala Pro Pro Asn Val Phe Ile Ser
        530                 535                 540

Asn Val Val Lys Asn Trp Asp Ile Glu Glu Asp Ser Leu Glu Pro Trp
545                 550                 555                 560

Val Ala Asn Asn Lys Asn Ala Tyr Val Asp Asn Thr Gly Gly Ile Glu
                565                 570                 575

Arg Ser Lys Ala Leu Phe Thr Gln Gly Asp Gly Glu Phe Ser Gln Phe
            580                 585                 590

Ile Gly Asp Lys Leu Lys Pro Asn Thr Asp Tyr Ile Ile Gln Tyr Thr
        595                 600                 605

Val Lys Gly Lys Pro Ala Ile Tyr Leu Lys Asn Lys Ser Thr Gly Tyr
    610                 615                 620

Ile Thr Tyr Glu Asp Thr Asn Gly Asn Ser Glu Glu Phe Gln Thr Ile
625                 630                 635                 640

Ala Val Lys Phe Thr Ser Glu Thr Asp Leu Ser Gln Thr His Leu Val
                645                 650                 655

Phe Lys Ser Gln Asn Gly Tyr Glu Ala Trp Gly Asp Asn Phe Ile Ile
            660                 665                 670

Leu Glu Ala Lys Leu Phe Glu Thr Pro Glu Ser Pro Glu Leu Ile Lys
        675                 680                 685

Phe Asn Asp Trp Glu Arg Phe Gly Thr Thr Tyr Ile Thr Gly Asn Glu
690                 695                 700

Leu Arg Ile Asp His Ser Arg Gly Gly Tyr Phe Arg Gln Ser Leu Asn
705                 710                 715                 720

Ile Asp Ser Tyr Ser Thr Tyr Asp Leu Ser Phe Ser Phe Ser Gly Leu
                725                 730                 735

Trp Ala Lys Val Ile Val Lys Asn Ser Arg Gly Val Val Leu Phe Glu
            740                 745                 750

Lys Val Lys Asn Asn Gly Ser Ser Tyr Glu Asp Ile Ser Glu Ser Phe
        755                 760                 765

Thr Thr Ala Ser Asn Lys Asp Gly Phe Phe Ile Glu Leu Thr Ala Glu
        770                 775                 780

Arg Thr Ser Ser Thr Phe His Ser Phe Arg Asp Ile Ser Ile Lys Glu
785                 790                 795                 800

Lys Ile Glu

<210> SEQ ID NO 44
<211> LENGTH: 2367
<212> TYPE: DNA
<213> ORGANISM: Artificial
```

<220> FEATURE:
<223> OTHER INFORMATION: Axmi005 optimized sequence

<400> SEQUENCE: 44

```
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg gcaacctcac cttggatgag atcctcaaga accagcagct gctgaatgag     180
atctcaggca agctggacgg cgtcaatgga agcctcaacg acctcattgc tcaaggcaac     240
ctcaacaccg agctgagcaa ggagatcctc aagattgcaa atgagcagaa ccaggtgctg     300
aatgatgtca acaacaagct ggacgccatc aacaccatgc tgcacatcta cctgccaaag     360
atcacctcaa tgctctctga tgtgatgaag cagaactacg cgctgagcct ccagattgag     420
tacctctcaa gcagctgca agagatctcc gacaagctgg acatcatcaa tgtcaatgtg     480
ctcatcaaca gcaccttgac agagatcacg ccggcctacc agaggatcaa gtatgtcaat     540
gagaagtttg aggagctcac cttcgccacc gagacaacat gaaggtgaa gaaggacagc     600
tcgccggcgg acatcctgga tgagctcacc gagctaacag agctggccaa gagcgtcacc     660
aagaatgatg ttgatggctt cgagttctac ctcaacaccct tccatgatgt gatggtgggc     720
aacaacctct tcggccgctc ggcgctcaag acggcgtcgg agctgatcgc caaggagaat     780
gtcaagacaa gtggatcaga ggtgggcaat gtctacaact tcctcatcgt gctgacggcg     840
ctgcaagcca aggccttcct caccttgaca acctgccgca gttgctgggg cctcgccgac     900
atcgactaca cctccatcat gaatgagcac ctcaacaagg agaaggagga gttccgcgtc     960
aacatcctgc aacattgag caacaccttc agcaaccca actacgccaa ggtgaagggc     1020
tcagatgaag atgccaagat gattgtggag gccaagcctg ccatgctct ggtgggcttc     1080
gagatgagca acgacagcat caccgtgctg aaggtctacg aggccaagct gaagcagaac     1140
taccaggtgg acaaggacag cttgtctgag gtgatctacg cgacatgga caagctgcta     1200
tgtccagatc aaagcgagca gatctactac accaacaaca tcgtcttcc aaatgaatat     1260
gtcatcacca agatcgactt caccaagaag atgaaaacat tgagatatga ggtgacggcc     1320
aacagctacg acagcagcac cggcgagatc gacctcaaca agaagaaggt ggagagctca     1380
gaagctgagt acaggacgct ctccgccaag gatgatggcg tctacatgcc gctcggcgtc     1440
atctcagaaa ccttcttgac gcccatcaat ggcttcggcc tccaagctga tgagaacagc     1500
aggctcatca ccttgacctg caagagctac ctcagggagc tgctgctggc caccgacctc     1560
agcaacaagg agacaaagct catcgtgccg ccatcaggct tcatcagcaa catcgtggag     1620
aatggcaacc tggaaggaga gaacctggag ccatggatag ccaacaacaa gaatgcttat     1680
gttgatcaca ccggcggcgt caatggaaca agggcgctct atgttcacaa ggatggaggc     1740
ttcagccagt tcatcggcga caagctgaag cccaagacag aatatgtcat ccagtacacc     1800
gtcaagggca agccatcaat ccacctcaag aatgagaaca ccggctacat ccactacgag     1860
gacaccaaca acaacctgga ggactaccag accatcacca agaggttcac caccggcacc     1920
gacctcaagg gcgtctacct catcttgaag agccaaaatg gagatgaagc atggggagac     1980
aacttcacca tcctggagat ctcgccatca gagaagctgc tctcgccgga gctcatcaat     2040
gtcaacaact ggatcagaac tggaagcacc cacatcagcg gcaacacctt gacgctctac     2100
caaggaggag gaggcaacct caagcagaac ctccagcttg acagcttctc cacctacagg     2160
gtgaacttct ccgtcaccgg cgacgccaat gtgaggatca gaaattcaag ggaggtgctc     2220
```

```
ttcgagaaga gatacatgag cggcgccaag gatgtttctg agatcttcac caccaagctg    2280
ggcaaggaca acttctacat cgagctgagc caaggcaaca acctctatgg agggccgctg    2340
gtgaagttca atgatgtgag catcaag                                        2367
```

<210> SEQ ID NO 45
<211> LENGTH: 789
<212> TYPE: PRT
<213> ORGANISM: Bacillus thuringiensis

<400> SEQUENCE: 45

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
            20                  25                  30

Ile Met Asn Met Ile Phe Lys Thr Asp Thr Gly Gly Asn Leu Thr Leu
        35                  40                  45

Asp Glu Ile Leu Lys Asn Gln Gln Leu Leu Asn Glu Ile Ser Gly Lys
    50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205

Leu Thr Glu Leu Thr Glu Leu Ala Lys Ser Val Thr Lys Asn Asp Val
    210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
                245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
    290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Asn Pro Asn Tyr Ala
                325                 330                 335

Lys Val Lys Gly Ser Asp Glu Asp Ala Lys Met Ile Val Glu Ala Lys
            340                 345                 350
```

```
Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
    370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
                405                 410                 415

Pro Asn Glu Tyr Val Ile Thr Lys Ile Asp Phe Thr Lys Lys Met Lys
                420                 425                 430

Thr Leu Arg Tyr Glu Val Thr Ala Asn Ser Tyr Asp Ser Ser Thr Gly
            435                 440                 445

Glu Ile Asp Leu Asn Lys Lys Lys Val Glu Ser Ser Glu Ala Glu Tyr
        450                 455                 460

Arg Thr Leu Ser Ala Lys Asp Asp Gly Val Tyr Met Pro Leu Gly Val
465                 470                 475                 480

Ile Ser Glu Thr Phe Leu Thr Pro Ile Asn Gly Phe Gly Leu Gln Ala
                485                 490                 495

Asp Glu Asn Ser Arg Leu Ile Thr Leu Thr Cys Lys Ser Tyr Leu Arg
                500                 505                 510

Glu Leu Leu Leu Ala Thr Asp Leu Ser Asn Lys Glu Thr Lys Leu Ile
            515                 520                 525

Val Pro Pro Ser Gly Phe Ile Ser Asn Ile Val Glu Asn Gly Asn Leu
        530                 535                 540

Glu Gly Glu Asn Leu Glu Pro Trp Ile Ala Asn Lys Asn Ala Tyr
545                 550                 555                 560

Val Asp His Thr Gly Gly Val Asn Gly Thr Arg Ala Leu Tyr Val His
                565                 570                 575

Lys Asp Gly Gly Phe Ser Gln Phe Ile Gly Asp Lys Leu Lys Pro Lys
                580                 585                 590

Thr Glu Tyr Val Ile Gln Tyr Thr Val Lys Gly Lys Pro Ser Ile His
            595                 600                 605

Leu Lys Asn Glu Asn Thr Gly Tyr Ile His Tyr Glu Asp Thr Asn Asn
        610                 615                 620

Asn Leu Glu Asp Tyr Gln Thr Ile Thr Lys Arg Phe Thr Thr Gly Thr
625                 630                 635                 640

Asp Leu Lys Gly Val Tyr Leu Ile Leu Lys Ser Gln Asn Gly Asp Glu
                645                 650                 655

Ala Trp Gly Asp Asn Phe Thr Ile Leu Glu Ile Ser Pro Ser Glu Lys
                660                 665                 670

Leu Leu Ser Pro Glu Leu Ile Asn Val Asn Asn Trp Ile Arg Thr Gly
            675                 680                 685

Ser Thr His Ile Ser Gly Asn Thr Leu Thr Leu Tyr Gln Gly Gly Gly
        690                 695                 700

Gly Asn Leu Lys Gln Asn Leu Gln Leu Asp Ser Phe Ser Thr Tyr Arg
705                 710                 715                 720

Val Asn Phe Ser Val Thr Gly Asp Ala Asn Val Arg Ile Arg Asn Ser
                725                 730                 735

Arg Glu Val Leu Phe Glu Lys Arg Tyr Met Ser Gly Ala Lys Asp Val
                740                 745                 750

Ser Glu Ile Phe Thr Thr Lys Leu Gly Lys Asp Asn Phe Tyr Ile Glu
            755                 760                 765
```

```
Leu Ser Gln Gly Asn Asn Leu Tyr Gly Gly Pro Leu Val Lys Phe Asn
    770                 775                 780

Asp Val Ser Ile Lys
785

<210> SEQ ID NO 46
<211> LENGTH: 4
<212> TYPE: PRT
<213> ORGANISM: Artificial
<220> FEATURE:
<223> OTHER INFORMATION: Axmi115 variant sequence

<400> SEQUENCE: 46

Lys Asp Glu Leu
1

<210> SEQ ID NO 47
<211> LENGTH: 2367
<212> TYPE: DNA
<213> ORGANISM: Artificial
<220> FEATURE:
<223> OTHER INFORMATION: Axmi115v02(evo38)

<400> SEQUENCE: 47
atgaacatga acaacaccaa gctcaatgca agggcgctgc cgagcttcat cgactacttc      60
aatggcatct atggcttcgc caccggcatc aaggacatca tgaacatgat cttcaagacc     120
gacaccggcg gcaacctcac cttggatgag atcctcaaga accagcagct gctgaatgag     180
atctcaggca gctggacgg cgtcaatgga agcctcaacg acctcattgc tcaaggcaac     240
ctcaacaccg agctgagcaa ggagatcctc aagattgcaa atgagcagaa ccaggtgctg     300
aatgatgtca acaacaagct ggacgccatc aacaccatgc tgcacatcta cctgccaaag     360
atcacctcaa tgctctctga tgtgatgaag cagaactacg cgctgagcct ccagattgag     420
tacctctcaa gcagctgca agagatctcc gacaagctgg acatcatcaa tgtcaatgtg     480
ctcatcaaca gcaccttgac agagatcacg ccggcctacc agaggatcaa gtatgtcaat     540
gagaagttcg aggagctcac cttcgccacc gagacaaccc tcaaggtcaa gaaagattca     600
tctcccgccg acatcttgga tgagttgaca gagctcaccg agctggccaa gagcgtcacc     660
aagaatgatg tggacggctt cgagttctac ctcaacaccct tccatgatgt gatggtcggc     720
aacaacctct ttggaagaag cgcgctcaag acggcatcag agctcatcgc caaggagaat     780
gtcaagacaa gcggcagcga ggtcggcaat gtctacaact tcctcatcgt gctgacagca     840
ttgcaagcca aggccttcct caccttgaca acctgccgca gttgctgggg cctcgccgac     900
atcgactaca cctccatcat gaatgagcac ctcaacaagg agaaggagga gttcagagtc     960
aacatcctgc cgacgctgag caacacgttc agcaacccaa actacgccaa ggtcaagggc    1020
tcagacgaag acgccaagat gatcgtggag gccaagcctg ccacgcgcgt ggtgggcttc    1080
gagatgagca atgattcaat tactgttctc aaggtctacg aggccaagct gaagcagaac    1140
taccaggtgg acaaggacag cttgagcgag gtgatctacg ggacatggga caagctcctc    1200
tgcccggatc aatcagagca gatctactac accaacaaca tcgtcttccc taatgaatat    1260
gtcatcacca agatcgactt cacgaagaag atgaaaaccc tcagatacga ggtcaccgcc    1320
aacagctatg attcatcaac aggagagatc gacctcaaca agaagaaagt ggagagctct    1380
gaagcagagt acaggaccct gtccgctaag gatgatggcg tctacatgcc gctcggcgtc    1440
atctcagaaa ccttcttgac gcccatcaac ggcttcggcc tgcaagcgga cgagaacagc    1500
```

| | | |
|---|---|---|
| aggctcatca cgctcacgtg caagagctac ctcagggagc tcctgctggc gaccgatttg | 1560 | |
| agcaacaagg agacaaagct gatcgtgccg ccaagtgggt tcatcagcaa tatcgtggag | 1620 | |
| aacgggaacc tcgaggggga gaacttggag ccatggatag ccaacaacaa gaatgcttat | 1680 | |
| gtggaccaca ccggcggcgt taatggaacc agggcgctct acgtccacaa agatggaggg | 1740 | |
| ttcagccagt tcatcggcga caagctaaag cccaagaccg aatacgtcat ccagtacacc | 1800 | |
| gtcaagggca agccgtccat ccacctcaag aacgagaaca ccggctacat ccactacgag | 1860 | |
| gacaccaata acaatcttga ggactaccaa acaattacta agaggttcac cacaggaaca | 1920 | |
| gatttgagcc agacccacct gatcttgaag agccaaaatg gagatgaagc atggggagac | 1980 | |
| aacttcacca tcctggagat ctcgccctcc gagaaactac taagcccgga gctcatcaat | 2040 | |
| gtcaataatt ggatcaggac cggcagcacc cacatcagcg gcaatacgct gacgctttat | 2100 | |
| caaggaggag gaggcaacct caagcaaaac ctccagctcg acagcttcag cacctaccgc | 2160 | |
| gtcaacttca gcgtcaccgg cgacgccaat gtgaggatca ggaacagccg cgaagtgctc | 2220 | |
| ttcgagaaga ggtacatgag tggagctaag gacgtctcag agatcttcac caccaaactc | 2280 | |
| ggcaaggata acttctacat cgagctctcc caggggaata acctctatgg cggcccctc | 2340 | |
| gtcaagttca atgacgtcag catcaag | 2367 | |

<210> SEQ ID NO 48
<211> LENGTH: 789
<212> TYPE: PRT
<213> ORGANISM: Artificial
<220> FEATURE:
<223> OTHER INFORMATION: Axmi115v02(evo38)

<400> SEQUENCE: 48

```
Met Asn Met Asn Asn Thr Lys Leu Asn Ala Arg Ala Leu Pro Ser Phe
1               5                   10                  15

Ile Asp Tyr Phe Asn Gly Ile Tyr Gly Phe Ala Thr Gly Ile Lys Asp
                20                  25                  30

Ile Met Asn Met Ile Phe Lys Thr Asp Thr Gly Gly Asn Leu Thr Leu
            35                  40                  45

Asp Glu Ile Leu Lys Asn Gln Gln Leu Leu Asn Glu Ile Ser Gly Lys
        50                  55                  60

Leu Asp Gly Val Asn Gly Ser Leu Asn Asp Leu Ile Ala Gln Gly Asn
65                  70                  75                  80

Leu Asn Thr Glu Leu Ser Lys Glu Ile Leu Lys Ile Ala Asn Glu Gln
                85                  90                  95

Asn Gln Val Leu Asn Asp Val Asn Asn Lys Leu Asp Ala Ile Asn Thr
            100                 105                 110

Met Leu His Ile Tyr Leu Pro Lys Ile Thr Ser Met Leu Ser Asp Val
        115                 120                 125

Met Lys Gln Asn Tyr Ala Leu Ser Leu Gln Ile Glu Tyr Leu Ser Lys
    130                 135                 140

Gln Leu Gln Glu Ile Ser Asp Lys Leu Asp Ile Ile Asn Val Asn Val
145                 150                 155                 160

Leu Ile Asn Ser Thr Leu Thr Glu Ile Thr Pro Ala Tyr Gln Arg Ile
                165                 170                 175

Lys Tyr Val Asn Glu Lys Phe Glu Glu Leu Thr Phe Ala Thr Glu Thr
            180                 185                 190

Thr Leu Lys Val Lys Lys Asp Ser Ser Pro Ala Asp Ile Leu Asp Glu
        195                 200                 205
```

-continued

Leu Thr Glu Leu Thr Glu Leu Ala Lys Ser Val Thr Lys Asn Asp Val
210                 215                 220

Asp Gly Phe Glu Phe Tyr Leu Asn Thr Phe His Asp Val Met Val Gly
225                 230                 235                 240

Asn Asn Leu Phe Gly Arg Ser Ala Leu Lys Thr Ala Ser Glu Leu Ile
            245                 250                 255

Ala Lys Glu Asn Val Lys Thr Ser Gly Ser Glu Val Gly Asn Val Tyr
            260                 265                 270

Asn Phe Leu Ile Val Leu Thr Ala Leu Gln Ala Lys Ala Phe Leu Thr
        275                 280                 285

Leu Thr Thr Cys Arg Lys Leu Leu Gly Leu Ala Asp Ile Asp Tyr Thr
290                 295                 300

Ser Ile Met Asn Glu His Leu Asn Lys Glu Lys Glu Glu Phe Arg Val
305                 310                 315                 320

Asn Ile Leu Pro Thr Leu Ser Asn Thr Phe Ser Pro Asn Tyr Ala
                325                 330                 335

Lys Val Lys Gly Ser Asp Glu Asp Ala Lys Met Ile Val Glu Ala Lys
            340                 345                 350

Pro Gly His Ala Leu Val Gly Phe Glu Met Ser Asn Asp Ser Ile Thr
        355                 360                 365

Val Leu Lys Val Tyr Glu Ala Lys Leu Lys Gln Asn Tyr Gln Val Asp
370                 375                 380

Lys Asp Ser Leu Ser Glu Val Ile Tyr Gly Asp Met Asp Lys Leu Leu
385                 390                 395                 400

Cys Pro Asp Gln Ser Glu Gln Ile Tyr Tyr Thr Asn Asn Ile Val Phe
            405                 410                 415

Pro Asn Glu Tyr Val Ile Thr Lys Ile Asp Phe Thr Lys Lys Met Lys
        420                 425                 430

Thr Leu Arg Tyr Glu Val Thr Ala Asn Ser Tyr Asp Ser Ser Thr Gly
        435                 440                 445

Glu Ile Asp Leu Asn Lys Lys Val Glu Ser Glu Ala Glu Tyr
450                 455                 460

Arg Thr Leu Ser Ala Lys Asp Asp Gly Val Tyr Met Pro Leu Gly Val
465                 470                 475                 480

Ile Ser Glu Thr Phe Leu Thr Pro Ile Asn Gly Phe Gly Leu Gln Ala
            485                 490                 495

Asp Glu Asn Ser Arg Leu Ile Thr Leu Thr Cys Lys Ser Tyr Leu Arg
            500                 505                 510

Glu Leu Leu Leu Ala Thr Asp Leu Ser Asn Lys Glu Thr Lys Leu Ile
        515                 520                 525

Val Pro Pro Ser Gly Phe Ile Ser Asn Ile Val Glu Asn Gly Asn Leu
530                 535                 540

Glu Gly Glu Asn Leu Glu Pro Trp Ile Ala Asn Asn Lys Asn Ala Tyr
545                 550                 555                 560

Val Asp His Thr Gly Gly Val Asn Gly Thr Arg Ala Leu Tyr Val His
            565                 570                 575

Lys Asp Gly Gly Phe Ser Gln Phe Ile Gly Asp Lys Leu Lys Pro Lys
        580                 585                 590

Thr Glu Tyr Val Ile Gln Tyr Thr Val Lys Gly Lys Pro Ser Ile His
        595                 600                 605

Leu Lys Asn Glu Asn Thr Gly Tyr Ile His Tyr Glu Asp Thr Asn Asn
610                 615                 620

Asn Leu Glu Asp Tyr Gln Thr Ile Thr Lys Arg Phe Thr Thr Gly Thr

-continued

```
625                 630                 635                 640
Asp Leu Ser Gln Thr His Leu Ile Leu Lys Ser Gln Asn Gly Asp Glu
                645                 650                 655
Ala Trp Gly Asp Asn Phe Thr Ile Leu Glu Ile Ser Pro Ser Glu Lys
                660                 665                 670
Leu Leu Ser Pro Glu Leu Ile Asn Val Asn Asn Trp Ile Arg Thr Gly
            675                 680                 685
Ser Thr His Ile Ser Gly Asn Thr Leu Thr Leu Tyr Gln Gly Gly Gly
        690                 695                 700
Gly Asn Leu Lys Gln Asn Leu Gln Leu Asp Ser Phe Ser Thr Tyr Arg
705                 710                 715                 720
Val Asn Phe Ser Val Thr Gly Asp Ala Asn Val Arg Ile Arg Asn Ser
                725                 730                 735
Arg Glu Val Leu Phe Glu Lys Arg Tyr Met Ser Gly Ala Lys Asp Val
                740                 745                 750
Ser Glu Ile Phe Thr Thr Lys Leu Gly Lys Asp Asn Phe Tyr Ile Glu
            755                 760                 765
Leu Ser Gln Gly Asn Asn Leu Tyr Gly Gly Pro Leu Val Lys Phe Asn
        770                 775                 780
Asp Val Ser Ile Lys
785
```

AXMI115 VARIANT INSECTICIDAL GENE AND METHODS FOR ITS USE

CROSS REFERENCE TO RELATED APPLICATION

This is a divisional of U.S. patent application Ser. No. 13/439,269, filed Apr. 4, 2012, which claims the benefit of U.S. Provisional Application Ser. No. 61/471,848, filed Apr. 5, 2011, the contents of which are herein incorporated by reference in their entirety.

REFERENCE TO SEQUENCE LISTING SUBMITTED ELECTRONICALLY

The official copy of the sequence listing is submitted electronically via EFS-Web as an ASCII formatted sequence listing with a file named "APA116021USSEQLIST.txt", created on Sep. 11, 2015, and having a size of 241 kilobytes and is filed concurrently with the specification. The sequence listing contained in this ASCII formatted document is part of the specification and is herein incorporated by reference in its entirety.

FIELD OF THE INVENTION

This invention relates to the field of molecular biology. Provided are novel genes that encode pesticidal proteins. These proteins and the nucleic acid sequences that encode them are useful in preparing pesticidal formulations and in the production of transgenic pest-resistant plants.

BACKGROUND OF THE INVENTION

*Bacillus thuringiensis* is a Gram-positive spore forming soil bacterium characterized by its ability to produce crystalline inclusions that are specifically toxic to certain orders and species of insects, but are harmless to plants and other non-targeted organisms. For this reason, compositions including *Bacillus thuringiensis* strains or their insecticidal proteins can be used as environmentally-acceptable insecticides to control agricultural insect pests or insect vectors for a variety of human or animal diseases.

Crystal (Cry) proteins (delta-endotoxins) from *Bacillus thuringiensis* have potent insecticidal activity against predominantly Lepidopteran, Hemipteran, Dipteran, and Coleopteran larvae. These proteins also have shown activity against Hymenoptera, Homoptera, Phthiraptera, Mallophaga, and Acari pest orders, as well as other invertebrate orders such as Nemathelminthes, Platyhelminthes, and Sarcomastigorphora (Feitelson (1993) The *Bacillus Thuringiensis* family tree. In *Advanced Engineered Pesticides*, Marcel Dekker, Inc., New York, N.Y.) The crystal protein does not exhibit insecticidal activity until it has been ingested and solubilized in the insect midgut. The ingested protoxin is hydrolyzed by proteases in the insect digestive tract to an active toxic molecule. (Höfte and Whiteley (1989) *Microbiol. Rev.* 53:242-255). This toxin binds to apical brush border receptors in the midgut of the target larvae and inserts into the apical membrane creating ion channels or pores, resulting in larval death.

In addition to the endotoxins, *B. thuringiensis* also produces secreted insecticidal proteins during its vegetative growth stage, namely, vegetative insecticidal proteins (Vip). Since the discovery of the first Vip toxin, two major groups of Vip toxins have been identified in *B. thuringiensis*. One group of Vip toxins consists of binary toxins which are made of two components, Vip1 and Vip2 (Warren (1997) In N. B. Carozzi and M. G. Koziel (ed.), Advances in insect control: the role of transgenic plants. Taylor & Francis, London, United Kingdom). The combination of Vip1 and Vip2 is highly insecticidal to an agriculturally important insect, the western corn rootworm (*Diabrotica virgifera*), but does not show any insecticidal activity for any lepidopteran insects (Han et al. (1999) *Nat. Struct. Biol.* 6:932-936). The other group consists of Vip3 toxins, which share no sequence similarity to Vip1 or Vip2. The first-identified Vip3 toxin, Vip3Aa1, is highly insecticidal to several major lepidopteran pests of maize and cotton, including the fall armyworm *Spodoptera frugiperda* and the cotton bollworm *Helicoverpa zea*, but shows no activity against the European corn borer *Ostrinia nubilalis*, a major pest of maize (Estruch et al. (1996) *Proc. Natl. Acad. Sci. USA* 93:5389-5394). The deletion of the vip3Aa1 gene from a *B. thuringiensis* strain resulted in a significant reduction of the insecticidal activity of that *B. thuringiensis* strain, suggesting that Vip3 contributes to the overall toxicity of *B. thuringiensis* strains (Donovan et al. (2001) *J. Invertebr. Pathol.* 78:45-51). It was also observed that Vip3Aa1 kills insects by lysing insect midgut cells (Yu et al. (1997) *Appl. Environ. Microbiol.* 63:532-536) via cell membrane pore formation (Lee et al. (2003) *Appl. Environ. Microbiol.* 69:4648-4657).

The intensive use of *B. thuringiensis*-based insecticides has already given rise to resistance in field populations of the diamondback moth, *Plutella xylostella* (Ferre and Van Rie (2002) *Annu. Rev. Entomol.* 47:501-533). The most common mechanism of resistance is the reduction of binding of the toxin to its specific midgut receptor(s). This may also confer cross-resistance to other toxins that share the same receptor (Ferre and Van Rie (2002)).

SUMMARY OF INVENTION

Compositions and methods for conferring pesticidal activity to bacteria, plants, plant cells, tissues and seeds are provided. Compositions include nucleic acid molecules encoding sequences for pesticidal and insectidal polypeptides, vectors comprising those nucleic acid molecules, and host cells comprising the vectors. Compositions also include the pesticidal polypeptide sequences and antibodies to those polypeptides. The nucleotide sequences can be used in DNA constructs or expression cassettes for transformation and expression in organisms, including microorganisms and plants. The nucleotide or amino acid sequences may be synthetic sequences that have been designed for expression in an organism including, but not limited to, a microorganism or a plant. Compositions also comprise bacteria, plants, plant cells, tissues, and seeds comprising the nucleotide sequence of the invention.

In particular, isolated nucleic acid molecules are provided that encode a pesticidal protein. Additionally, amino acid sequences corresponding to the pesticidal protein are encompassed. In particular, the present invention provides for an isolated or recombinant nucleic acid molecule comprising a nucleotide sequence encoding a fusion protein, as well as biologically active variants and fragments thereof, wherein the fusion protein comprises the C-terminal portion of SEQ ID NO:43. In various embodiments, the fusion protein comprises the N-terminal portion of SEQ ID NO:45. In specific embodiments, the nucleic acid molecule encompassed by the present invention (including vectors, host cells, plants, and seeds comprising the nucleic acid molecule) comprises the nucleotide sequence set forth in SEQ ID NO:47 and 1-14, or a nucleotide sequence encoding the amino acid sequence set forth in SEQ ID NO:2, 3, 7-14 and 47, including biologically active variants and fragments thereof. Nucleotide sequences that are complementary to a nucleotide sequence of the invention, or that hybridize to a sequence of the invention or a complement thereof are also encompassed. Isolated or recombinant fusion proteins encoded by the nucleci acid molecule of the invention are also encompassed herein.

Methods are provided for producing the polypeptides of the invention, and for using those polypeptides for controlling or killing a lepidopteran, hemipteran, coleopteran, nematode, or dipteran pest. Methods and kits for detecting the nucleic acids and polypeptides of the invention in a sample are also included.

The compositions and methods of the invention are useful for the production of organisms with enhanced pest resistance or tolerance. These organisms and compositions comprising the organisms are desirable for agricultural purposes. The compositions of the invention are also useful for generating altered or improved proteins that have pesticidal activity, or for detecting the presence of pesticidal proteins or nucleic acids in products or organisms.

DETAILED DESCRIPTION

Figure 1:
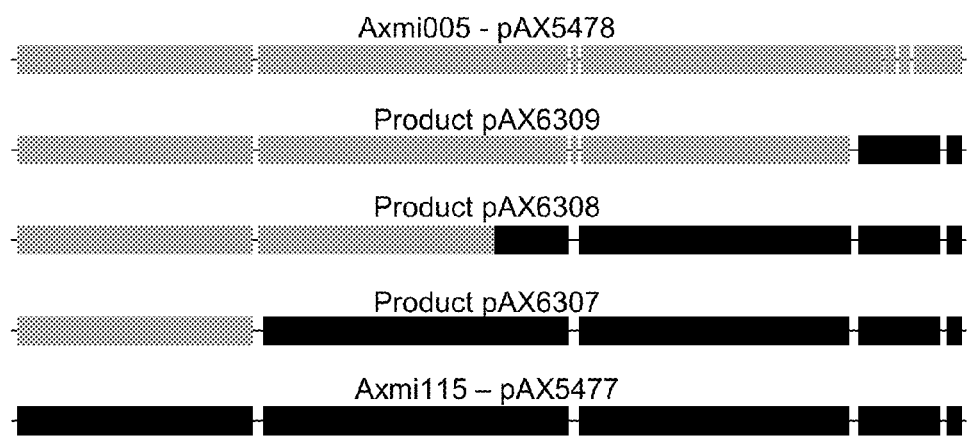
FIG. 1 shows a diagram of the fusion constructs.

The present invention is drawn to compositions and methods for regulating pest resistance or tolerance in organisms, particularly plants or plant cells. By "resistance" is intended that the pest (e.g., insect) is killed upon ingestion or other contact with the polypeptides of the invention. By "tolerance" is intended an impairment or reduction in the movement, feeding, reproduction, or other functions of the pest. The methods involve transforming organisms with a nucleotide sequence encoding a pesticidal protein of the invention. In particular, the nucleotide sequences of the invention are useful for preparing plants and microorganisms that possess pesticidal activity. Thus, transformed bacteria, plants, plant cells, plant tissues and seeds are provided. Compositions are pesticidal nucleic acids and proteins of Bacillus or other species. The sequences find use in the construction of expression vectors for subsequent transformation into organisms of interest, as probes for the isolation of other homologous (or partially homologous) genes, and for the generation of altered pesticidal proteins by methods known in the art, such as domain swapping or DNA shuffling, for example, with members of the Vip1, Vip2, or Vip3 families of toxins. The proteins find use in controlling or killing lepidopteran, hemipteran, coleopteran, dipteran, and nematode pest populations and for producing compositions with pesticidal activity.

By "pesticidal toxin" or "pesticidal protein" is intended a toxin that has toxic activity against one or more pests, including, but not limited to, members of the Lepidoptera, Diptera, and Coleoptera orders, or the Nematoda phylum, or a protein that has homology to such a protein. Pesticidal proteins have been isolated from organisms including, for example, Bacillus sp., Clostridium bifermentans and Paenibacillus popilliae. Pesticidal proteins include amino acid sequences deduced from the full-length nucleotide sequences disclosed herein, and amino acid sequences that are shorter than the full-length sequences, either due to the use of an alternate downstream start site, or due to processing that produces a shorter protein having pesticidal activity. Processing may occur in the organism the protein is expressed in, or in the pest after ingestion of the protein.

Thus, provided herein are novel isolated or recombinant nucleotide sequences that confer pesticidal activity. These nucleotide sequences encode polypeptides with homology to known toxins. Also provided are the amino acid sequences of the pesticidal proteins. The protein resulting from translation of this gene allows cells to control or kill pests that ingest it.

Isolated Nucleic Acid Molecules, and Variants and Fragments Thereof

One aspect of the invention pertains to isolated or recombinant nucleic acid molecules comprising nucleotide sequences encoding pesticidal proteins and polypeptides or biologically active portions thereof, as well as nucleic acid molecules sufficient for use as hybridization probes to identify nucleic acid molecules encoding proteins with regions of sequence homology. Also encompassed herein are nucleotide sequences capable of hybridizing to the nucleotide sequences of the invention under stringent conditions as defined elsewhere herein. As used herein, the term "nucleic acid molecule" is intended to include DNA molecules (e.g., recombinant DNA, cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" or "recombinant" nucleic acid sequence (or DNA) is used herein to refer to a nucleic acid sequence (or DNA) that is no longer in its natural environment, for example in an in vitro or in a recombinant bacterial or plant host cell. In some embodiments, an isolated or recombinant nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the invention, "isolated" when used to refer to nucleic acid molecules excludes isolated chromosomes. For example, in various embodiments, the isolated delta-endotoxin encoding nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived. In various embodiments, a delta-endotoxin protein that is substantially free of cellular material includes preparations of protein having less than about 30%, 20%, 10%, or 5% (by dry weight) of non-delta-endotoxin protein (also referred to herein as a "contaminating protein").

Nucleotide sequences encoding the proteins of the present invention include the sequence set forth in SEQ ID NO:47 and 1-14, and variants, fragments, and complements thereof. By "complement" is intended a nucleotide sequence that is sufficiently complementary to a given nucleotide sequence such that it can hybridize to the given nucleotide sequence to thereby form a stable duplex. The corresponding amino acid sequences for the pesticidal proteins encoded by these nucleotide sequences are set forth in SEQ ID NO:2, 3, 7-14 and 47.

Nucleic acid molecules that are fragments of these nucleotide sequences encoding pesticidal proteins are also encompassed by the present invention. By "fragment" is intended a portion of the nucleotide sequence encoding a pesticidal protein. A fragment of a nucleotide sequence may encode a biologically active portion of a pesticidal protein, or it may be a fragment that can be used as a hybridization probe or PCR primer using methods disclosed below. Nucleic acid molecules that are fragments of a nucleotide sequence encoding a pesticidal protein comprise at least about 50, 100, 200, 300, 400, 500, 600, 700, 800, 900, 1000, 1100, 1200, 1300, 1350, 1400 contiguous nucleotides, or up to the number of nucleotides present in a full-length nucleotide sequence encoding a pesticidal protein disclosed herein, depending upon the intended use. By "contiguous" nucleotides is intended nucleotide residues that are immediately adjacent to one another. Fragments of the nucleotide sequences of the present invention will encode protein fragments that retain the biological activity of the pesticidal protein and, hence, retain pesticidal activity. Thus, biologically-active fragments of the polypeptides disclosed herein are also encompassed. By "retains activity" is intended that the fragment will have at least about 30%, at least about 50%, at least about 70%, 80%, 90%, 95% or higher of the pesticidal activity of the pesticidal protein. In various embodiments, the activity may be improved or extended relative to a reference pesticidal protein (e.g., improved or extended relative to the activity of SEQ ID NO:43 or 45) as defined elsewhere herein. In one embodiment, the pesticidal activity is coleoptericidal activity. In another embodiment, the pesticidal activity is lepidoptericidal activity. In another embodiment, the pesticidal activity is nematocidal activity. In another embodiment, the pesticidal activity is diptericidal activity. In another embodiment, the pesticidal activity is hemiptericidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

A fragment of a nucleotide sequence encoding a pesticidal protein that encodes a biologically active portion of a protein of the invention will encode at least about 15, 25, 30, 50, 75, 100, 125, 150, 175, 200, 250, 300, 350, 400, 450 contiguous amino acids, or up to the total number of amino acids present in a full-length pesticidal protein of the invention. In some embodiments, the fragment is a proteolytic cleavage fragment. For example, the proteolytic cleavage fragment may have an N-terminal or a C-terminal truncation of at least about 100 amino acids, about 120, about 130, about 140, about 150, or about 160 amino acids relative to SEQ ID NO:2, 3, 7-14 and 47. In some embodiments, the fragments encompassed herein result from the removal of the C-terminal crystallization domain, e.g., by proteolysis or by insertion of a stop codon in the coding sequence. In other embodiments, the fusion protein comprises a fragment of the C-terminal domain of SEQ ID NO:43 and/or a fragment of the N-terminal domain of SEQ ID NO:45.

Preferred pesticidal proteins of the present invention are encoded by a nucleotide sequence sufficiently identical to the nucleotide sequence of SEQ ID NO:47 and 1-14, or the pesticidal proteins are sufficiently identical to the amino acid sequence set forth in SEQ ID NO:2, 3, 7-14 and 47. In another embodiment, the nucleotide sequence encodes a fusion protein, wherein the N-terminal portion is sufficiently identical to the N-terminal portion of SEQ ID NO:45, or wherein the N-terminal portion is sufficiently identical to the N-terminal portion of SEQ ID NO:45 and the C-terminal portion is sufficiently identical to SEQ ID NO:43. By "sufficiently identical" is intended an amino acid or nucleotide sequence that has at least about 60% or 65% sequence identity, about 70% or 75% sequence identity, about 80% or 85% sequence identity, about 90%, 91%, 92%, 93%, 94%, 95%, 96%, 97%, 98%, 99% or greater sequence identity compared to a reference sequence using one of the alignment programs described herein using standard parameters. One of skill in the art will recognize that these values can be appropriately adjusted to determine corresponding identity of proteins encoded by two nucleotide sequences by taking into account codon degeneracy, amino acid similarity, reading frame positioning, and the like.

To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences are the same length. In another embodiment, the percent identity is calculated across the entirety of the reference sequence (i.e., the sequence disclosed herein as any of SEQ ID NO:1-31, 47 or 48). The percent identity between two sequences can be determined using techniques similar to those described below, with or without allowing gaps. In calculating percent identity, typically exact matches are counted. A gap, i.e. a position in an alignment where a residue is present in one sequence but not in the other, is regarded as a position with non-identical residues.

The determination of percent identity between two sequences can be accomplished using a mathematical algorithm. A nonlimiting example of a mathematical algorithm utilized for the comparison of two sequences is the algorithm of Karlin and Altschul (1990) *Proc. Natl. Acad. Sci. USA* 87:2264, modified as in Karlin and Altschul (1993) *Proc. Natl. Acad. Sci. USA* 90:5873-5877. Such an algorithm is incorporated into the BLASTN and BLASTX programs of Altschul et al. (1990) *J. Mol. Biol.* 215:403. BLAST nucleotide searches can be performed with the BLASTN program, score=100, wordlength=12, to obtain nucleotide sequences homologous to pesticidal-like nucleic acid molecules of the invention. BLAST protein searches can be performed with the BLASTX program, score=50, wordlength=3, to obtain amino acid sequences homologous to pesticidal protein molecules of the invention. To obtain gapped alignments for comparison purposes, Gapped BLAST (in BLAST 2.0) can be utilized as described in Altschul et al. (1997) *Nucleic Acids Res.* 25:3389. Alternatively, PSI-Blast can be used to perform an iterated search that detects distant relationships between molecules. See Altschul et al. (1997) supra. When utilizing BLAST, Gapped BLAST, and PSI-Blast programs, the default parameters of the respective programs (e.g., BLASTX and BLASTN) can be used. Alignment may also be performed manually by inspection.

Another non-limiting example of a mathematical algorithm utilized for the comparison of sequences is the ClustalW algorithm (Higgins et al. (1994) *Nucleic Acids Res.* 22:4673-4680). ClustalW compares sequences and aligns the entirety of the amino acid or DNA sequence, and thus can provide data about the sequence conservation of the entire amino acid sequence. The ClustalW algorithm is used in several commercially available DNA/amino acid analysis software packages, such as the ALIGNX module of the Vector NTI Program Suite (Invitrogen Corporation, Carlsbad, Calif.). After alignment of amino acid sequences with ClustalW, the percent amino acid identity can be assessed. A non-limiting example of a software program useful for analysis of ClustalW alignments is GENEDOC™. GENE- DOC™ (Karl Nicholas) allows assessment of amino acid (or DNA) similarity and identity between multiple proteins. Another non-limiting example of a mathematical algorithm utilized for the comparison of sequences is the algorithm of Myers and Miller (1988) *CABIOS* 4:11-17. Such an algorithm is incorporated into the ALIGN program (version 2.0), which is part of the GCG Wisconsin Genetics Software Package, Version 10 (available from Accelrys, Inc., 9685 Scranton Rd., San Diego, Calif., USA). When utilizing the ALIGN program for comparing amino acid sequences, a PAM120 weight residue table, a gap length penalty of 12, and a gap penalty of 4 can be used.

Unless otherwise stated, GAP Version 10, which uses the algorithm of Needleman and Wunsch (1970) *J. Mol. Biol.* 48(3):443-453, will be used to determine sequence identity or similarity using the following parameters: % identity and % similarity for a nucleotide sequence using GAP Weight of 50 and Length Weight of 3, and the nwsgapdna.cmp scoring matrix; % identity or % similarity for an amino acid sequence using GAP weight of 8 and length weight of 2, and the BLOSUM62 scoring program. Equivalent programs may also be used. By "equivalent program" is intended any sequence comparison program that, for any two sequences in question, generates an alignment having identical nucleotide residue matches and an identical percent sequence identity when compared to the corresponding alignment generated by GAP Version 10.

The invention also encompasses variant nucleic acid molecules. "Variants" of the pesticidal protein encoding nucleotide sequences include those sequences that encode the pesticidal proteins disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleotide sequences also include synthetically derived nucleotide sequences that have been generated, for example, by using site-directed mutagenesis but which still encode the pesticidal proteins disclosed in the present invention as discussed below. Variant proteins encompassed by the present invention are biologically active, that is they continue to possess the desired biological activity of the native protein, that is, pesticidal activity. By "retains activity" is intended that the variant will have at least about 30%, at least about 50%, at least about 70%, or at least about 80% of the pesticidal activity of the native protein. In some embodiments, the activity is improved or extended relative to a reference protein as defined elsewhere herein. Methods for measuring pesticidal activity are well known in the art. See, for example, Czapla and Lang (1990) *J. Econ. Entomol.* 83: 2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

The skilled artisan will further appreciate that changes can be introduced by mutation of the nucleotide sequences of the invention thereby leading to changes in the amino acid sequence of the encoded pesticidal proteins, without altering the biological activity of the proteins. Thus, variant isolated nucleic acid molecules can be created by introducing one or more nucleotide substitutions, additions, or deletions into the corresponding nucleotide sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleotide sequences are also encompassed by the present invention.

For example, conservative amino acid substitutions may be made at one or more, predicted, nonessential amino acid residues. A "nonessential" amino acid residue is a residue that can be altered from the wild-type sequence of a pesticidal protein without altering the biological activity, whereas an "essential" amino acid residue is required for biological activity. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

Amino acid substitutions may be made in nonconserved regions that retain function. In general, such substitutions would not be made for conserved amino acid residues, or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the invention (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the invention (e.g., residues that have only conservative substitutions between all proteins contained in the alignment homologous proteins). However, one of skill in the art would understand that functional variants may have minor conserved or nonconserved alterations in the conserved residues.

Alternatively, variant nucleotide sequences can be made by introducing mutations randomly along all or part of the coding sequence, such as by saturation mutagenesis, and the resultant mutants can be screened for ability to confer pesticidal activity to identify mutants that retain activity. Following mutagenesis, the encoded protein can be expressed recombinantly, and the activity of the protein can be determined using standard assay techniques.

Using methods such as PCR, hybridization, and the like corresponding pesticidal sequences can be identified, such sequences having substantial identity to the sequences of the invention. See, for example, Sambrook and Russell (2001) *Molecular Cloning: A Laboratory Manual.* (Cold Spring Harbor Laboratory Press, Cold Spring Harbor, N.Y.) and Innis, et al. (1990) *PCR Protocols: A Guide to Methods and Applications* (Academic Press, NY).

In a hybridization method, all or part of the pesticidal nucleotide sequence can be used to screen cDNA or genomic libraries. Methods for construction of such cDNA and genomic libraries are generally known in the art and are disclosed in Sambrook and Russell, 2001, supra. The so-called hybridization probes may be genomic DNA fragments, cDNA fragments, RNA fragments, or other oligonucleotides, and may be labeled with a detectable group such as $^{32}$P, or any other detectable marker, such as other radioisotopes, a fluorescent compound, an enzyme, or an enzyme co-factor. Probes for hybridization can be made by labeling synthetic oligonucleotides based on the known pesticidal protein-encoding nucleotide sequence disclosed herein. Degenerate primers designed on the basis of conserved nucleotides or amino acid residues in the nucleotide sequence or encoded amino acid sequence can additionally be used. The probe typically comprises a region of nucleotide sequence that hybridizes under stringent conditions to at least about 12, at least about 25, at least about 50, 75, 100, 125, 150, 175, or 200 consecutive nucleotides of nucleotide sequence encoding a pesticidal protein of the invention or a fragment or variant thereof. Methods for the preparation of probes for hybridization are generally known in the art and are disclosed in Sambrook and Russell, 2001, supra herein incorporated by reference.

For example, an entire pesticidal sequence disclosed herein, or one or more portions thereof, may be used as a probe capable of specifically hybridizing to corresponding pesticidal protein-like sequences and messenger RNAs. To achieve specific hybridization under a variety of conditions, such probes include sequences that are unique and are preferably at least about 10 nucleotides in length, or at least about 20 nucleotides in length. Such probes may be used to amplify corresponding pesticidal sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Cold Spring Harbor, N.Y.).

Thus, the present invention encompasses probes for hybridization, as well as nucleotide sequences capable of hybridization to all or a portion of a nucleotide sequence of the invention (e.g., at least about 300 nucleotides, at least about 400, at least about 500, 1000, 1200, 1500, 2000, 2500, 3000, 3500, or up to the full length of a nucleotide sequence disclosed herein). Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the $T_m$ can be approximated from the equation of Meinkoth and Wahl (1984) *Anal. Biochem.* 138:267-284: $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York). See Sambrook et al. (1989) *Molecular Cloning: A Laboratory Manual* (2d ed., Cold Spring Harbor Laboratory Press, Cold Spring Harbor, N.Y.).

Isolated Proteins and Variants and Fragments Thereof

Pesticidal proteins are also encompassed within the present invention. By "pesticidal protein" is intended a protein having the amino acid sequence set forth in SEQ ID NO:2, 3, 7-14 and 47. Fragments, biologically active portions, and variants thereof are also provided, and may be used to practice the methods of the present invention. An "isolated protein" or a "recombinant protein" is used to refer to a protein that is no longer in its natural environment, for example in vitro or in a recombinant bacterial or plant host cell.

"Fragments" or "biologically active portions" include polypeptide fragments comprising amino acid sequences sufficiently identical to the amino acid sequence set forth in SEQ ID NO:2, 3, 7-14 and 47, and that exhibit pesticidal activity. A biologically active portion of a pesticidal protein can be a polypeptide that is, for example, 10, 25, 50, 100, 150, 200, 250, 300, 350, 400, 450, 500, 550, 600, 650, 700, 750, 800, 850, 900, 950, 1000, 1050, 1100, 1150, 1200, 1250, 1300, 1350, or more amino acids in length. Such biologically active portions can be prepared by recombinant techniques and evaluated for pesticidal activity. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety. As used here, a fragment comprises at least 8 contiguous amino acids of SEQ ID NO:2, 3, 7-14 and 47. The invention encompasses other fragments, however, such as any fragment in the protein greater than about 10, 20, 30, 50, 100, 150, 200, 250, 300, 350, 400, 450, 500, 550, 600, 650, 700, 750, 800, 850, 900, 950, 1000, 1050, 1100, 1150, 1200, 1250, 1300, 1350 or more amino acids in length.

By "variants" is intended proteins or polypeptides having an amino acid sequence that is at least about 60%, 65%, about 70%, 75%, about 80%, 85%, about 90%, 91%, 92%, 93%, 94%, 95%, 96%, 97%, 98% or 99% identical to the amino acid sequence of any of SEQ ID NO:2, 3, 7-14 and 47. Variants also include polypeptides encoded by a nucleic acid molecule that hybridizes to the nucleic acid molecule of SEQ ID NO:47 and 1-14, or a complement thereof, under stringent conditions. Variants include polypeptides that differ in amino acid sequence due to mutagenesis. Variant proteins encompassed by the present invention are biologically active, that is they continue to possess the desired biological activity of the native protein, that is, retaining pesticidal activity. In some embodiments, the variants have improved activity relative to the native protein. Methods for measuring pesticidal activity are well known in the art. See, for example, Czapla and Lang (1990) *J. Econ. Entomol.* 83:2480-2485; Andrews et al. (1988) *Biochem. J.* 252:199-206; Marrone et al. (1985) *J. of Economic Entomology* 78:290-293; and U.S. Pat. No. 5,743,477, all of which are herein incorporated by reference in their entirety.

Bacterial genes, such as the axmi genes of this invention, quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to generation of pesticidal proteins. These pesticidal proteins are encompassed in the present invention and may be used in the methods of the present invention. It will be understood that, when expressed in plants, it will be necessary to alter the alternate start codon to ATG for proper translation.

Antibodies to the polypeptides of the present invention, or to variants or fragments thereof, are also encompassed. Methods for producing antibodies are well known in the art (see, for example, Harlow and Lane (1988) *Antibodies: A Laboratory Manual*, Cold Spring Harbor Laboratory, Cold Spring Harbor, N.Y.; U.S. Pat. No. 4,196,265).

Altered or Improved Variants

It is recognized that DNA sequences of a pesticidal protein may be altered by various methods, and that these alterations may result in DNA sequences encoding proteins with amino acid sequences different than that encoded by a pesticidal protein of the present invention. This protein may be altered in various ways including amino acid substitutions, deletions, truncations, and insertions of one or more amino acids of SEQ ID NO:2, 3, 7-14 and 47, including up to about 2, about 3, about 4, about 5, about 6, about 7, about 8, about 9, about 10, about 15, about 20, about 25, about 30, about 35, about 40, about 45, about 50, about 55, about 60, about 65, about 70, about 75, about 80, about 85, about 90, about 100, about 105, about 110, about 115, about 120, about 125, about 130, about 135, about 140, about 145, about 150, about 155, or more amino acid substitutions, deletions or insertions within either the C-terminal portion or the N-terminal portion, or both. Methods for such manipulations are generally known in the art. For example, amino acid sequence variants of a pesticidal protein can be prepared by mutations in the DNA. This may also be accomplished by one of several forms of mutagenesis and/or in directed evolution. In some aspects, the changes encoded in the amino acid sequence will not substantially affect the function of the protein. Such variants will possess the desired pesticidal activity. However, it is understood that the ability of a pesticidal protein to confer pesticidal activity may be improved by the use of such techniques upon the compositions of this invention. For example, one may express a pesticidal protein in host cells that exhibit high rates of base misincorporation during DNA replication, such as XL-1 Red (Stratagene, La Jolla, Calif.). After propagation in such strains, one can isolate the DNA (for example by preparing plasmid DNA, or by amplifying by PCR and cloning the resulting PCR fragment into a vector), culture the pesticidal protein mutations in a non-mutagenic strain, and identify mutated genes with pesticidal activity, for example by performing an assay to test for pesticidal activity. Generally, the protein is mixed and used in feeding assays. See, for example Marrone et al. (1985) *J. of Economic Entomology* 78:290-293. Such assays can include contacting plants with one or more pests and determining the plant's ability to survive and/or cause the death of the pests. Examples of mutations that result in increased toxicity are found in Schnepf et al. (1998) *Microbiol. Mol. Biol. Rev.* 62:775-806.

Alternatively, alterations may be made to the protein sequence of many proteins at the amino or carboxy terminus without substantially affecting activity. This can include insertions, deletions, or alterations introduced by modern molecular methods, such as PCR, including PCR amplifications that alter or extend the protein coding sequence by virtue of inclusion of amino acid encoding sequences in the oligonucleotides utilized in the PCR amplification. Alternatively, the protein sequences added can include entire protein-coding sequences, such as those used commonly in the art to generate protein fusions. Such fusion proteins are often used to (1) increase expression of a protein of interest (2) introduce a binding domain, enzymatic activity, or epitope to facilitate either protein purification, protein detection, or other experimental uses known in the art (3) target secretion or translation of a protein to a subcellular organelle, such as the periplasmic space of Gram-negative bacteria, or the endoplasmic reticulum of eukaryotic cells, the latter of which often results in glycosylation of the protein.

Variant nucleotide and amino acid sequences of the present invention also encompass sequences derived from mutagenic and recombinogenic procedures such as DNA shuffling. With such a procedure, one or more different pesticidal protein coding regions can be used to create a new pesticidal protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene of the invention and other known pesticidal genes to obtain a new gene coding for a protein with an improved property of interest, such as an increased insecticidal activity. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458.

Domain swapping or shuffling is another mechanism for generating altered pesticidal proteins. Domains may be swapped between pesticidal proteins, resulting in hybrid or chimeric toxins with improved pesticidal activity or target spectrum. Methods for generating recombinant proteins and testing them for pesticidal activity are well known in the art (see, for example, Naimov et al. (2001) *Appl. Environ. Microbiol.* 67:5328-5330; de Maagd et al. (1996) *Appl. Environ. Microbiol.* 62:1537-1543; Ge et al. (1991) *J. Biol. Chem.* 266:17954-17958; Schnepf et al. (1990) *J. Biol. Chem.* 265:20923-20930; Rang et al. 91999) *Appl. Environ. Microbiol.* 65:2918-2925).

Thus, in various embodiments of the present invention, the nucleic acid sequences encompassed herein (as well as compositions, vectors, host cells, plants, and seed comprising the nucleic acid sequence) comprise a portion of one or more toxin(s) and a portion of one of more different toxin(s). In one embodiment, the nucleic acid sequence comprises a nucleotide sequence encoding the N-terminal portion of Axmi005 (which is set forth in SEQ ID NO:45) and the C-terminal portion of Axmi115 (which is set forth in SEQ ID NO:43). In specific embodiments, the N-terminal portion of Axmi005 comprises from about amino acid residues 1 to 173, or from about amino acid residue 1, 2, 3, 4, 5, 6, 7, 8, 9, 10, 15, 20, 25, 30, 35, 40, 45, or 50 to about amino acid residue 150, 155, 160, 165, 170, 171, 172, 173, 174, 175, 176, 177, 178, 179, 180, 185, 190, 195, 200, 205, 210, 215, 220, 225, 230, 250, 300, 325, or 350 of Axmi005 and the C-terminal portion of Axmi115 comprises from about amino acid residue 174 to about amino acid residue 803 of Axmi115, or from about amino acid residue 170, 171, 172, 173, 174, 175, 176, 177, 178, 179, 180, 185, 190, 195, 200, 205, 210, 215, 220, 225, 230, 250, 300, 325, or 350 to about amino acid residue 600, 650, 700, 750, 760, 770, 780, 790, 795, 796, 797, 798, 799, 800, 801, 802, or 803. One of skill in the art will recognize that minor variants and deletions within each of the amino acid sequences can be made and still retain (or improve) activity of the fusion protein. In some embodiments, the nucleic acid sequences of the invention encode an Axmi005/Axmi115 fusion protein with a mutation (relative to the corresponding region of the parent Axmi005 or Axmi115 protein) at one or more of positions corresponding to the amino acid residues at positions 584, 588, and 771 relative to SEQ ID NO:43 (see, for example, the variant fusion sequences found in SEQ ID NO:18-22). In other embodiments, the nucleotide sequence encompassed herein is set forth in any of SEQ ID NO:47 and 1-14 and the amino acid sequence is set forth in any of SEQ ID NO:2, 3, 7-14 and 47.

In various embodiments, the fusion of Axmi005 with Axmi115 results in an amino acid sequence having improved or extended activity compared to the activity of either Axmi005 or Axmi115 alone. By "improved" activity is intended an increase in death to at least one pest, or an increase in the noticeable reduction of pest growth, feeding, or normal physiological development relative to the native protein. By "extended" activity is intended activity against a pest that was not demonstrated by both Axmi005 and Axmi115. For example, fusion of a portion of Axmi005 with a portion of Axmi115 could result in a single protein having the activity profile of both Axmi005 and Axmi115. In some embodiments, activity against an individual pest is improved in the fusion protein over one or both of Axmi005 and/or Axmi115.

Vectors

A pesticidal sequence of the invention may be provided in an expression cassette for expression in a plant of interest. By "plant expression cassette" is intended a DNA construct that is capable of resulting in the expression of a protein from an open reading frame in a plant cell. Typically these contain a promoter and a coding sequence. Often, such constructs will also contain a 3' untranslated region. Such constructs may contain a "signal sequence" or "leader sequence" to facilitate co-translational or post-translational transport of the peptide to certain intracellular structures such as the chloroplast (or other plastid), endoplasmic reticulum, or Golgi apparatus.

By "signal sequence" is intended a sequence that is known or suspected to result in cotranslational or post-translational peptide transport across the cell membrane. In eukaryotes, this typically involves secretion into the Golgi apparatus, with some resulting glycosylation. Insecticidal toxins of bacteria are often synthesized as protoxins, which are protolytically activated in the gut of the target pest (Chang (1987) *Methods Enzymol.* 153:507-516). In some embodiments of the present invention, the signal sequence is located in the native sequence, or may be derived from a sequence of the invention. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria, and the like.

By "plant transformation vector" is intended a DNA molecule that is necessary for efficient transformation of a plant cell. Such a molecule may consist of one or more plant expression cassettes, and may be organized into more than one "vector" DNA molecule. For example, binary vectors are plant transformation vectors that utilize two non-contiguous DNA vectors to encode all requisite cis- and trans-acting functions for transformation of plant cells (Hellens and Mullineaux (2000) *Trends in Plant Science* 5:446-451). "Vector" refers to a nucleic acid construct designed for transfer between different host cells. "Expression vector" refers to a vector that has the ability to incorporate, integrate and express heterologous DNA sequences or fragments in a foreign cell. The cassette will include 5' and/or 3' regulatory sequences operably linked to a sequence of the invention. By "operably linked" is intended a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame. The cassette may additionally contain at least one additional gene to be cotransformed into the organism. Alternatively, the additional gene(s) can be provided on multiple expression cassettes.

In various embodiments, the nucleotide sequence of the invention is operably linked to a promoter, e.g., a plant promoter. "Promoter" refers to a nucleic acid sequence that functions to direct transcription of a downstream coding sequence. The promoter together with other transcriptional and translational regulatory nucleic acid sequences (also termed "control sequences") are necessary for the expression of a DNA sequence of interest.

Such an expression cassette is provided with a plurality of restriction sites for insertion of the pesticidal sequence to be under the transcriptional regulation of the regulatory regions.

The expression cassette will include in the 5'-3' direction of transcription, a transcriptional and translational initiation region (i.e., a promoter), a DNA sequence of the invention, and a translational and transcriptional termination region (i.e., termination region) functional in plants. The promoter may be native or analogous, or foreign or heterologous, to the plant host and/or to the DNA sequence of the invention. Additionally, the promoter may be the natural sequence or alternatively a synthetic sequence. Where the promoter is "native" or "homologous" to the plant host, it is intended that the promoter is found in the native plant into which the promoter is introduced. Where the promoter is "foreign" or "heterologous" to the DNA sequence of the invention, it is intended that the promoter is not the native or naturally occurring promoter for the operably linked DNA sequence of the invention.

The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acid Res.* 15:9627-9639.

Where appropriate, the gene(s) may be optimized for increased expression in the transformed host cell. That is, the genes can be synthesized using host cell-preferred codons for improved expression, or may be synthesized using codons at a host-preferred codon usage frequency. Generally, the GC content of the gene will be increased. See, for example, Campbell and Gowri (1990) *Plant Physiol.* 92:1-11 for a discussion of host-preferred codon usage. Methods are available in the art for synthesizing plant-preferred genes. See, for example, U.S. Pat. Nos. 5,380,831, and 5,436,391, U.S. Patent Publication No. 20090137409, and Murray et al. (1989) *Nucleic Acids Res.* 17:477-498, herein incorporated by reference.

In one embodiment, the pesticidal protein is targeted to the chloroplast for expression. In this manner, where the pesticidal protein is not directly inserted into the chloroplast, the expression cassette will additionally contain a nucleic acid encoding a transit peptide to direct the pesticidal protein to the chloroplasts. Such transit peptides are known in the art. See, for example, Von Heijne et al. (1991) *Plant Mol. Biol. Rep.* 9:104-126; Clark et al. (1989) *J. Biol. Chem.* 264:17544-17550; Della-Cioppa et al. (1987) *Plant Physiol.* 84:965-968; Romer et al. (1993) *Biochem. Biophys. Res. Commun.* 196:1414-1421; and Shah et al. (1986) *Science* 233:478-481.

The pesticidal gene to be targeted to the chloroplast may be optimized for expression in the chloroplast to account for differences in codon usage between the plant nucleus and this organelle. In this manner, the nucleic acids of interest may be synthesized using chloroplast-preferred codons. See, for example, U.S. Pat. No. 5,380,831, herein incorporated by reference.

Plant Transformation

Methods of the invention involve introducing a nucleotide construct into a plant. By "introducing" is intended to present to the plant the nucleotide construct in such a manner that the construct gains access to the interior of a cell of the plant. The methods of the invention do not require that a particular method for introducing a nucleotide construct to a plant is used, only that the nucleotide construct gains access to the interior of at least one cell of the plant. Methods for introducing nucleotide constructs into plants are known in the art including, but not limited to, stable transformation methods, transient transformation methods, and virus-mediated methods.

By "plant" is intended whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

The transgenic plants of the invention express one or more of the novel toxin sequences disclosed herein. In various embodiments, the transgenic plant further comprises one or more additional genes for insect resistance (e.g., Cry1, such as members of the Cry1A, Cry1B, Cry1C, Cry1D, Cry1E, and Cry1F families; Cry2, such as members of the Cry2A family; Cry9, such as members of the Cry9A, Cry9B, Cry9C, Cry9D, Cry9E, and Cry9F families; etc.). It will be understood by one of skill in the art that the transgenic plant may comprise any gene imparting an agronomic trait of interest.

Transformation of plant cells can be accomplished by one of several techniques known in the art. The pesticidal gene of the invention may be modified to obtain or enhance expression in plant cells. Typically a construct that expresses such a protein would contain a promoter to drive transcription of the gene, as well as a 3' untranslated region to allow transcription termination and polyadenylation. The organization of such constructs is well known in the art. In some instances, it may be useful to engineer the gene such that the resulting peptide is secreted, or otherwise targeted within the plant cell. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically this "plant expression cassette" will be inserted into a "plant transformation vector". This plant transformation vector may be comprised of one or more DNA vectors needed for achieving plant transformation. For example, it is a common practice in the art to utilize plant transformation vectors that are comprised of more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) *The Plant Journal* 6:271-282; Ishida et al. (1996) *Nature Biotechnology* 14:745-750). Explants are typically transferred to a fresh supply of the same medium and cultured routinely. A general description of the techniques and methods for generating transgenic plants are found in Ayres and Park (1994) *Critical Reviews in Plant Science* 13:219-239 and Bommineni and Jauhar (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation (U.S. Published Application No. 20010026941; U.S. Pat. No. 4,945,050; International Publication No. WO 91/00915; U.S. Published Application No. 2002015066), Lec1 transformation, and various other non-particle direct-mediated methods to transfer DNA.

Methods for transformation of chloroplasts are known in the art. See, for example, Svab et al. (1990) *Proc. Natl. Acad. Sci. USA* 87:8526-8530; Svab and Maliga (1993) *Proc. Natl. Acad. Sci. USA* 90:913-917; Svab and Maliga (1993) *EMBO J.* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) *Molecular Cloning: A Laboratory Manual*. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformant, fractionated in a formaldehyde agarose gel, and blotted onto a nylon filter according to standard procedures that are routinely used in the art (Sambrook and Russell, 2001, supra). Expression of RNA encoded by the pesticidal gene is then tested by hybridizing the filter to a radioactive probe derived from a pesticidal gene, by methods known in the art (Sambrook and Russell, 2001, supra).

Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the pesticidal protein.

Pesticidal Activity in Plants

In another aspect of the invention, one may generate transgenic plants expressing a pesticidal protein that has pesticidal activity. Methods described above by way of example may be utilized to generate transgenic plants, but the manner in which the transgenic plant cells are generated is not critical to this invention. Methods known or described in the art such as *Agrobacterium*-mediated transformation, biolistic transformation, and non-particle-mediated methods may be used at the discretion of the experimenter. Plants expressing a pesticidal protein may be isolated by common methods described in the art, for example by transformation of callus, selection of transformed callus, and regeneration of fertile plants from such transgenic callus. In such process, one may use any gene as a selectable marker so long as its expression in plant cells confers ability to identify or select for transformed cells.

A number of markers have been developed for use with plant cells, such as resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) *J. Biol. Chem.* 263:6310-6314 (bromoxynil resistance nitrilase gene); and Sathasivan et al. (1990) *Nucl. Acids Res.* 18:2188 (AHAS imidazolinone resistance gene). Additionally, the genes disclosed herein are useful as markers to assess transformation of bacterial or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a pesticidal protein may be tested for pesticidal activity, and the plants showing optimal activity selected for further breeding. Methods are available in the art to assay for pest activity. Generally, the protein is mixed and used in feeding assays. See, for example Marrone et al. (1985) *J. of Economic Entomology* 78:290-293.

The present invention may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassava, coffee, coconut, pineapple, citrus trees, cocoa, tea, banana, avocado, fig, guava, mango, olive, papaya, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, hydrangea, hibiscus, roses, tulips, daffodils, petunias, carnation, poinsettia, and chrysanthemum. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

Use in Pesticidal Control

General methods for employing strains comprising a nucleotide sequence of the present invention, or a variant thereof, in pest control or in engineering other organisms as pesticidal agents are known in the art. See, for example U.S. Pat. No. 5,039,523 and EP 0480762A2.

The *Bacillus* strains containing a nucleotide sequence of the present invention, or a variant thereof, or the microorganisms that have been genetically altered to contain a pesticidal gene of the invention and protein may be used for protecting agricultural crops and products from pests. In one aspect of the invention, whole, i.e., unlysed, cells of a toxin (pesticide)-producing organism are treated with reagents that prolong the activity of the toxin produced in the cell when the cell is applied to the environment of target pest(s).

Alternatively, the pesticide is produced by introducing a pesticidal gene into a cellular host. Expression of the pesticidal gene results, directly or indirectly, in the intracellular production and maintenance of the pesticide. In one aspect of this invention, these cells are then treated under conditions that prolong the activity of the toxin produced in the cell when the cell is applied to the environment of the target pest(s). The resulting product retains the toxicity of the toxin. These naturally encapsulated pesticides may then be formulated in accordance with conventional techniques for application to the environment hosting a target pest, e.g., soil, water, and foliage of plants. See, for example EPA 0192319, and the references cited therein. Alternatively, one may formulate the cells expressing a gene of this invention such as to allow application of the resulting material as a pesticide.

The active ingredients of the present invention are normally applied in the form of compositions and can be applied to the crop area or plant to be treated, simultaneously or in succession, with other compounds. These compounds can be fertilizers, weed killers, cryoprotectants, surfactants, detergents, pesticidal soaps, dormant oils, polymers, and/or time-release or biodegradable carrier formulations that permit long-term dosing of a target area following a single application of the formulation. They can also be selective herbicides, chemical insecticides, virucides, microbicides, amoebicides, pesticides, fungicides, bacteriocides, nematocides, molluscicides or mixtures of several of these preparations, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise the formulations may be prepared into edible "baits" or fashioned into pest "traps" to permit feeding or ingestion by a target pest of the pesticidal formulation.

Methods of applying an active ingredient of the present invention or an agrochemical composition of the present invention that contains at least one of the pesticidal proteins produced by the bacterial strains of the present invention include leaf application, seed coating and soil application. The number of applications and the rate of application depend on the intensity of infestation by the corresponding pest.

The composition may be formulated as a powder, dust, pellet, granule, spray, emulsion, colloid, solution, or such like, and may be prepared by such conventional means as desiccation, lyophilization, homogenation, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

Lepidopteran, hemipteran, dipteran, or coleopteran pests may be killed or reduced in numbers in a given area by the methods of the invention, or may be prophylactically applied to an environmental area to prevent infestation by a susceptible pest. Preferably the pest ingests, or is contacted with, a pesticidally-effective amount of the polypeptide. By "pesticidally-effective amount" is intended an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

The pesticide compositions described may be made by formulating either the bacterial cell, the crystal and/or the spore suspension, or the isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline or other buffer. The formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. The term "agriculturally-acceptable carrier" covers all adjuvants, inert components, dispersants, surfactants, tackifiers, binders, etc. that are ordinarily used in pesticide formulation technology; these are well known to those skilled in pesticide formulation. The formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference.

"Pest" includes but is not limited to, insects, fungi, bacteria, nematodes, mites, ticks, and the like. Insect pests include insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, Lepidoptera, and Diptera.

The order Coleoptera includes the suborders Adephaga and Polyphaga. Suborder Adephaga includes the superfamilies Caraboidea and Gyrinoidea, while suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

The order Lepidoptera includes the families Papilionidae, Pieridae, Lycaenidae, Nymphalidae, Danaidae, Satyridae, Hesperiidae, Sphingidae, Saturniidae, Geometridae, Arctiidae, Noctuidae, Lymantriidae, Sesiidae, and Tineidae.

Insect pests of the invention for the major crops include: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus, sorghum* borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*; corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: Pseudaletia unipunctata, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; *Sitodiplosis mosellana*, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, bandedwinged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus leucopterus*, chinch bug; *Acrosternum hilare*, green stink bug; Soybean: *Pseudoplusia includens*, soybean looper; *Anticarsia gemmatalis*, velvetbean caterpillar; *Plathypena scabra*, green cloverworm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; Hylemya *platura*, seedcorn maggot; *Sericothrips variabilis*, soybean thrips; *Thrips tabaci*, onion thrips; *Tetranychus* turkestani, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

Nematodes include parasitic nematodes such as root-knot, cyst, and lesion nematodes, including *Heterodera* spp., *Meloidogyne* spp., and *Globodera* spp.; particularly members of the cyst nematodes, including, but not limited to, *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include *Pratylenchus* spp.

Methods for Increasing Plant Yield

Methods for increasing plant yield are provided. The methods comprise providing a plant or plant cell expressing a polynucleotide encoding the pesticidal polypeptide sequence disclosed herein and growing the plant or a seed thereof in a field infested with (or susceptible to infestation by) a pest against which said polypeptide has pesticidal activity. In some embodiments, the polypeptide has pesticidal activity against a lepidopteran, coleopteran, dipteran, hemipteran, or nematode pest, and said field is infested with a lepidopteran, hemipteran, coleopteran, dipteran, or nematode pest. As defined herein, the "yield" of the plant refers to the quality and/or quantity of biomass produced by the plant. By "biomass" is intended any measured plant product. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield compared to a plant not expressing the pesticidal sequence. In specific methods, plant yield is increased as a result of improved pest resistance of a plant expressing a pesticidal protein disclosed herein. Expression of the pesticidal protein results in a reduced ability of a pest to infest or feed.

The plants can also be treated with one or more chemical compositions, including one or more herbicide, insecticides, or fungicides. Exemplary chemical compositions include: Fruits/Vegetables Herbicides: Atrazine, Bromacil, Diuron, Glyphosate, Linuron, Metribuzin, Simazine, Trifluralin, Fluazifop, Glufosinate, Halo sulfuron Gowan, Paraquat, Propyzamide, Sethoxydim, Butafenacil, Halosulfuron, Indaziflam; Fruits/Vegetables Insecticides: Aldicarb, *Bacillus thuriengiensis*, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; Fruits/Vegetables Fungicides: Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin; Cereals Herbicides: 2.4-D, Amidosulfuron, Bromoxynil, Carfentrazone-E, Chlorotoluron, Chlorsulfuron, Clodinafop-P, Clopyralid, Dicamba, Diclofop-M, Diflufenican, Fenoxaprop, Florasulam, Flucarbazone-NA, Flufenacet, Flupyrosulfuron-M, Fluroxypyr, Flurtamone, Glyphosate, Iodosulfuron, Ioxynil, Isoproturon, MCPA, Mesosulfuron, Metsulfuron, Pendimethalin, Pinoxaden, Propoxycarbazone, Prosulfocarb, Pyroxsulam, Sulfosulfuron, Thifensulfuron, Tralkoxydim, Triasulfuron, Tribenuron, Trifluralin, Tritosulfuron; Cereals Fungicides: Azoxystrobin, Bixafen, Boscalid, Carbendazim, Chlorothalonil, Cyflufenamid, Cyproconazole, Cyprodinil, Dimoxystrobin, Epoxiconazole, Fenpropidin, Fenpropimorph, Fluopyram, Fluoxastrobin, Fluquinconazole, Fluxapyroxad, Isopyrazam, Kresoxim-methyl, Metconazole, Metrafenone, Penthiopyrad, Picoxystrobin, Prochloraz, Propiconazole, Proquinazid, Prothioconazole, Pyraclostrobin, Quinoxyfen, Spiroxamine, Tebuconazole, Thiophanate-methyl, Trifloxystrobin; Cereals Insecticides: Dimethoate, Lambda-cyhalthrin, Deltamethrin, alpha-Cypermethrin, β-cyfluthrin, Bifenthrin, Imidacloprid, Clothianidin, Thiamethoxam, Thiacloprid, Acetamiprid, Dinetofuran, Clorphyriphos, Pirimicarb, Methiocarb, Sulfoxaflor; Maize Herbicides: Atrazine, Alachlor, Bromoxynil, Acetochlor, Dicamba, Clopyralid, (S-)Dimethenamid, Glufosinate, Glyphosate, Isoxaflutole, (S-)Metolachlor, Mesotrione, Nicosulfuron, Primisulfuron, Rimsulfuron, Sulcotrione, Foramsulfuron, Topramezone, Tembotrione, Saflufenacil, Thiencarbazone, Flufenacet, Pyroxasulfon; Maize Insecticides: Carbofuran, Chlorpyrifos, Bifenthrin, Fipronil, Imidacloprid, Lambda-Cyhalothrin, Tefluthrin, Terbufos, Thiamethoxam, Clothianidin, Spiromesifen, Flubendiamide, Triflumuron, Rynaxypyr, Deltamethrin, Thiodicarb, β-Cyfluthrin, Cypermethrin, Bifenthrin, Lufenuron, Tebupirimphos, Ethiprole, Cyazypyr, Thiacloprid, Acetamiprid, Dinetofuran, Avermectin; Maize Fungicides: Azoxystrobin, Bixafen, Boscalid, Cyproconazole, Dimoxystrobin, Epoxiconazole, Fenitropan, Fluopyram, Fluoxastrobin, Fluxapyroxad, Isopyrazam, Metconazole, Penthiopyrad, Picoxystrobin, Propiconazole, Prothioconazole, Pyraclostrobin, Tebuconazole, Trifloxystrobin; Rice Herbicides: Butachlor, Propanil, Azimsulfuron, Bensulfuron, Cyhalofop, Daimuron, Fentrazamide, Imazosulfuron, Mefenacet, Oxaziclomefone, Pyrazosulfuron, Pyributicarb, Quinclorac, Thiobencarb, Indanofan, Flufenacet, Fentrazamide, Halosulfuron, Oxaziclomefone, Benzobicyclon, Pyriftalid, Penoxsulam, Bispyribac, Oxadiargyl, Ethoxysulfuron, Pretilachlor, Mesotrione, Tefuryltrione, Oxadiazone, Fenoxaprop, Pyrimisulfan; Rice Insecticides: Diazinon, Fenobucarb, Benfuracarb, Buprofezin, Dinotefuran, Fipronil, Imidacloprid, Isoprocarb, Thiacloprid, Chromafenozide, Clothianidin, Ethiprole, Flubendiamide, Rynaxypyr, Deltamethrin, Acetamiprid, Thiamethoxam, Cyazypyr, Spinosad, Spinotoram, Emamectin-Benzoate, Cypermethrin, Chlorpyriphos, Etofenprox, Carbofuran, Benfuracarb, Sulfoxaflor; Rice Fungicides: Azoxystrobin, Carbendazim, Carpropamid, Diclocymet, Difenoconazole, Edifenphos, Ferimzone, Gentamycin, Hexaconazole, Hymexazol, Iprobenfos (IBP), Isoprothiolane, Isotianil, Kasugamycin, Mancozeb, Metominostrobin, Orysastrobin, Pencycuron, Probenazole, Propiconazole, Propineb, Pyroquilon, Tebuconazole, Thiophanate-methyl, Tiadinil, Tricyclazole, Trifloxystrobin, Validamycin; Cotton Herbicides: Diuron, Fluometuron, MSMA, Oxyfluorfen, Prometryn, Trifluralin, Carfentrazone, Clethodim, Fluazifop-butyl, Glyphosate, Norflurazon, Pendimethalin, Pyrithiobac-sodium, Trifloxysulfuron, Tepraloxydim, Glufosinate, Flumioxazin, Thidiazuron; Cotton Insecticides: Acephate, Aldicarb, Chlorpyrifos, Cypermethrin, Deltamethrin, Abamectin, Acetamiprid, Emamectin Benzoate, Imidacloprid, Indoxacarb, Lambda-Cyhalothrin, Spinosad, Thiodicarb, Gamma-Cyhalothrin, Spiromesifen, Pyridalyl, Flonicamid Flubendiamide, Triflumuron, Rynaxypyr, Beta-Cyfluthrin, Spirotetramat, Clothianidin, Thiamethoxam, Thiacloprid, Dinetofuran, Flubendiamide, Cyazypyr, Spinosad, Spinotoram, gamma Cyhalothrin, 4-[[(6-Chlorpyridin-3-yl)methyl](2,2-difluorethyl)amino]furan-2(5H)-on, Thiodicarb, Avermectin, Flonicamid, Pyridalyl, Spiromesifen, Sulfoxaflor; Cotton Fungicides: Azoxystrobin, Bixafen, Boscalid, Carbendazim, Chlorothalonil, Copper, Cyproconazole, Difenoconazole, Dimoxystrobin, Epoxiconazole, Fenamidone, Fluazinam, Fluopyram, Fluoxastrobin, Fluxapyroxad, Iprodione, Isopyrazam, Isotianil, Mancozeb, Maneb, Metominostrobin, Penthiopyrad, Picoxystrobin, Propineb, Prothioconazole, Pyraclostrobin, Quintozene, Tebuconazole, Tetraconazole, Thiophanate-methyl, Trifloxystrobin; Soybean Herbicides: Alachlor, Bentazone, Trifluralin, Chlorimuron-Ethyl, Cloransulam-Methyl, Fenoxaprop, Fomesafen, Fluazifop, Glyphosate, Imazamox, Imazaquin, Imazethapyr, (S-) Metolachlor, Metribuzin, Pendimethalin, Tepraloxydim, Glufosinate; Soybean Insecticides: Lambda-cyhalothrin, Methomyl, Imidacloprid, Clothianidin, Thiamethoxam, Thiacloprid, Acetamiprid, Dinetofuran, Flubendiamide, Rynaxypyr, Cyazypyr, Spinosad, Spinotoram, Emamectin-Benzoate, Fipronil, Ethiprole, Deltamethrin, β-Cyfluthrin, gamma and lambda Cyhalothrin, 4-[[(6-Chlorpyridin-3-yl)methyl](2,2-difluorethyl)amino]furan-2(5H)-on, Spirotetramat, Spinodiclofen, Triflumuron, Flonicamid, Thiodicarb, beta-Cyfluthrin; Soybean Fungicides: Azoxystrobin, Bixafen, Boscalid, Carbendazim, Chlorothalonil, Copper, Cyproconazole, Difenoconazole, Dimoxystrobin, Epoxiconazole, Fluazinam, Fluopyram, Fluoxastrobin, Flutriafol, Fluxapyroxad, Isopyrazam, Iprodione, Isotianil, Mancozeb, Maneb, Metconazole, Metominostrobin, Myclobutanil, Penthiopyrad, Picoxystrobin, Propiconazole, Propineb, Prothioconazole, Pyraclostrobin, Tebuconazole, Tetraconazole, Thiophanate-methyl, Trifloxystrobin; Sugarbeet Herbicides: Chloridazon, Desmedipham, Ethofumesate, Phenmedipham, Triallate, Clopyralid, Fluazifop, Lenacil, Metamitron, Quinmerac, Cycloxydim, Triflusulfuron, Tepraloxydim, Quizalofop; Sugarbeet Insecticides: Imidacloprid, Clothianidin, Thiamethoxam, Thiacloprid, Acetamiprid, Dinetofuran, Deltamethrin, β-Cyfluthrin, gamma/lambda Cyhalothrin, 4-[[(6-Chlorpyridin-3-yl)methyl](2,2-difluorethyl)amino]furan-2(5H)-on, Tefluthrin, Rynaxypyr, Cyaxypyr, Fipronil, Carbofuran; Canola Herbicides: Clopyralid, Diclofop, Fluazifop, Glufosinate, Glyphosate, Metazachlor, Trifluralin Ethametsulfuron, Quinmerac, Quizalofop, Clethodim, Tepraloxydim; Canola Fungicides: Azoxystrobin, Bixafen, Boscalid, Carbendazim, Cyproconazole, Difenoconazole, Dimoxystrobin, Epoxiconazole, Fluazinam, Fluopyram, Fluoxastrobin, Flusilazole, Fluxapyroxad, Iprodione, Isopyrazam, Mepiquat-chloride, Metconazole, Metominostrobin, Paclobutrazole, Penthiopyrad, Picoxystrobin, Prochloraz, Prothioconazole, Pyraclostrobin, Tebuconazole, Thiophanate-methyl, Trifloxystrobin, Vinclozolin; Canola Insecticides: Carbofuran, Thiacloprid, Deltamethrin, Imidacloprid, Clothianidin, Thiamethoxam, Acetamiprid, Dinetofuran, β-Cyfluthrin, gamma and lambda Cyhalothrin, tau-Fluvaleriate, Ethiprole, Spinosad, Spinotoram, Flubendiamide, Rynaxypyr, Cyazypyr, 4-[[(6-Chlorpyridin-3-yl)methyl](2,2-difluorethyl)amino]furan-2(5H)-on.

The following examples are offered by way of illustration and not by way of limitation.

EXPERIMENTAL EXAMPLES

Example 1. Design and Testing of Axmi115 Fusion Proteins

Axmi115 is described in U.S. Patent Publication 20100004176 (the amino acid sequence is set forth herein as SEQ ID NO:43). This gene shares 70% sequence homology with Vip3Aa. A codon optimized version of Axmi115 (also referred to herein as Axmi115v01 and set forth in SEQ ID NO:42) was cloned and expressed using the *E. coli* expression vector. The protein produced was shown in in vitro bioassay to have pesticidal activity against various insect pests including European corn borer (ECB), corn earworm (CEW), fall armyworm (FAW) and black cutworm (BCW).

Axmi005 is also described in U.S. Patent Publication 20100004176. This gene shares 94% sequence homology with Vip3Aa. A codon optimized version of Axmi005 (optAxmi005, which is set forth herein as SEQ ID NO:44) was cloned and expressed using the *E. coli* expression vector. The protein produced was shown in in vitro bioassay to have pesticidal activity against various insect pests including *Helicoverpa zea* (Hz), *Heliothis virescens* (Hv), FAW, BCW, sugarcane borer (SCB), and velvetbean caterpillar (VBC).

The relative activity of Axmi115 was low against Hz and FAW compared to Axmi005. Also as noted above Axmi005 did not have ECB activity. In an attempt to identify the domains responsible for the differential specificity as well as activity of the two proteins, constructs expressing fusions of optAxmi005 and a codon-optimized version of Axmi115 (optAxmi115v01) were made as described below and diagrammed in FIG. 1. The protein was expressed in *E. coli* and tested against ECB, Hz, FAW and BCW in in vitro bioassay. The protein expressed by pAX6307 (Axmi115v02.01, set forth herein as SEQ ID NO:1) showed enhanced activity when compared with the protein expressed by pAX5477 (Axmi115v01, set forth herein as SEQ ID NO:42) against all four pests tested.

The gene expressed in pAX6307 (Axmi115v02.01) was vectored into the plant expression vector pAG6141 in which expression of the protein was driven by the Sugar cane Ubiquitin promoter.

Leaf samples from transgenic plants expressing Axmi115v01 and Axmi115v02.01 were tested in laboratory insect bioassay against ECB, Hz, FAW and BCW and in field tests against ECB, Hz and FAW. Results show that the improved Axmi115v02.01 gene had better efficacy against all pests tested.

Description of Constructs:

Amino acid sequences derived by in silico translation of the DNA sequence of Vip3Aa, Axmi005, Axmi115v01, Axmi163, and Axmi184 were aligned to identify conserved amino acids in all homologs (Axmi163 and Axmi184 are also described in U.S. Patent Publication 20100004176).

PCR primers were designed to three conserved regions of Axmi005 and Axmi115v01 using the sequence of optAxmi005 found in pAX5478 (which contains a codon optimized version of Axmi005, set forth in SEQ ID NO:44) and the sequence of optAxmi115 found in pAX5477 (which contains a codon optimized version of Axmi115). Three fusion genes were generated by overlap PCR (see FIG. 1).

The DNA of the fusion genes produced by these PCR reactions was cloned into the *E. coli* expression vector pRSf1B. The resulting expression vectors are shown in Table 1. Protein was expressed using known methods and the *E. coli* extract was tested in an in vitro bioassay.

TABLE 1

| Fusion gene constructs | | | |
|---|---|---|---|
| Construct name | Sequence insert | Nucleotide SEQ ID NO: | Amino acid SEQ ID NO: |
| pAX6307 | Axmi005/Axmi115 fusion A | 1 | 15 |
| pAX6308 | Axmi005/Axmi115 fusion B | 2 | 16 |
| pAX6309 | Axmi005/Axmi115 fusion D | 3 | 17 |
| pAX5478 | optAxmi005 | 44 | 45 |
| pAX5477 | Axmi115v01 | 42 | 43 |
| pRSf1b | vector control | — | — |

In-Vitro Bioassay

Crude extracts from *E. coli* expressed in vectors was assayed against Hz, ECB, FAW, and BCW. The results are shown in Table 2 (stunt) and Table 3 (mortality).

TABLE 2

| | Stunt score | | | | | | | | | | | |
|---|---|---|---|---|---|---|---|---|---|---|---|---|
| | ECB | | | Hz | | | FAW | | | BCW | | |
| | ave* | SD | | ave* | SD | | ave* | SD | | ave* | SD | |
| pAX6307 (fusion A) | 2.2 | 0.3 | pAX6307 | 1.8 | 0.3 | pAX6307 | 3 | 0 | pAX6307 | 0.8 | 0.3 | |
| pAX6308 (fusion B) | 0.5 | 0.5 | pAX6308 | 0.3 | 0.4 | pAX6308 | 1.3 | 1.3 | pAX6308 | 0 | 0 | |
| pAX6309 (fusion D) | 1.2 | 0.3 | pAX6309 | 0.2 | 0.3 | pAX6309 | 0.7 | 0.7 | pAX6309 | 0 | 0 | |
| pRSf1b (vector control) | 0.3 | 0.4 | pRSf1b | 0 | 0 | pRSf1b | 0.5 | 0.5 | pRSf1b | 0 | 0 | |
| pAX5478 (Axmi005) | 0 | 0 | pAX5478 | 1.8 | 0.3 | pAX5478 | 3 | 0 | pAX5478 | 1.7 | 0.7 | |
| pAX5477 (Axmi115v01) | 0.2 | 0.3 | pAX5477 | 0.5 | 0.5 | pAX5477 | 1.5 | 1.5 | pAX5477 | 0.2 | 0.3 | |

*Scoring system: 0 = no effect observed 1 = mild non-uniform stunting 2 = moderate non-uniform stunting 3 = moderate to severe uniform stunting 4 = mortality (<100%) with uniform stunting 5 = complete mortality

TABLE 3

| | Percent mortality | | | |
|---|---|---|---|---|
| | Hz | ECB | FAW | BCW |
| pAX6307 (fusion A) | 50 | 50 | 75 | 25 |
| pAX6308 (fusion B) | 0 | 0 | 0 | 0 |
| pAX6309 (fusion D) | 0 | 25 | 25 | 0 |
| pRSf1b (vector control) | 0 | 0 | 0 | 0 |
| pAX5478 (optAxmi005) | 50 | 0 | 75 | 25 |
| pAX5477 (Axmi115v01) | 0 | 0 | 0 | 0 |

The protein expressed from vector pAX6307 (fusion A) varied by six amino acids and was designated Axmi115v02.01. The amino acid sequence for this fusion protein is set forth in SEQ ID NO:15.

E. coli expression vectors expressing Axmi115v01 (pAX5476) and Axmi115v02.01 (pAX6307) had N-terminal 6×His Tags. The two proteins were purified using the nickel binding properties of the 6×His tag. Various concentrations of the purified protein were assayed by in vitro bioassay against ECB, FAW, BCW and Beet Armyworm (BAW). The results show that Axmi115v02.01 has enhanced activity compared with Axmi115v01 in all cases (Tables 4 and 5).

TABLE 4

| | Stunt score | | | | |
|---|---|---|---|---|---|
| | µg/ml | BAW | FAW | ECB | BCW |
| Axmi115v01 | 40 | 4 | 4 | 3 | 0 |
| Axmi115v01 | 10 | 1 | 3 | 0 | 0 |
| Axmi115v01 | 1 | 0 | 0 | 0 | 0 |
| Axmi115v01 | 0.1 | 0 | 0 | 0 | 0 |
| Axmi115v01 | 0.01 | 0 | 1 | 0 | 0 |
| Axmi115v02 | 40 | 4 | 4 | 3 | 3 |
| Axmi115v02 | 10 | 4 | 4 | 3 | 1 |
| Axmi115v02 | 1 | 4 | 4 | 3 | 0 |
| Axmi115v02 | 0.1 | 2 | 1 | 2 | 0 |
| Axmi115v02 | 0.01 | 0 | 2 | 1 | 0 |

TABLE 5

| | Mortality score | | | | |
|---|---|---|---|---|---|
| | µg/ml | BAW | FAW | ECB | BCW |
| Axmi115v01 | 40 | 75% | 0% | 0% | 0% |
| Axmi115v01 | 10 | 0% | 25% | 0% | 0% |
| Axmi115v01 | 1 | 0% | 0% | 0% | 0% |
| Axmi115v01 | 0.1 | 0% | 0% | 0% | 0% |
| Axmi115v01 | 0.01 | 0% | 0% | 0% | 0% |
| Axmi115v02 | 40 | 75% | 50% | 0% | 0% |
| Axmi115v02 | 10 | 0% | 25% | 50% | 0% |
| Axmi115v02 | 1 | 0% | 25% | 0% | 0% |
| Axmi115v02 | 0.1 | 0% | 0% | 0% | 0% |
| Axmi115v02 | 0.01 | 0% | 0% | 0% | 0% |

Plant Leaf Disc Bioassay

Axmi115v01 (SEQ ID NO:42) and Axmi115v02.01 (SEQ ID NO:1) were cloned into plant expression vectors pAG6585 and pAG6141, respectively, and transgenic maize plants were produced. Samples were taken for PCR and Western analysis and for in vitro leaf disc bioassay against Hz, ECB, FAW, and BCW. The bioassay was scored for undamaged, low damage (1-few holes), moderate damage, and heavy damage. Undamaged and light damaged were considered a positive result whereas moderate to heavy damage was considered a negative result.

Figure 2:
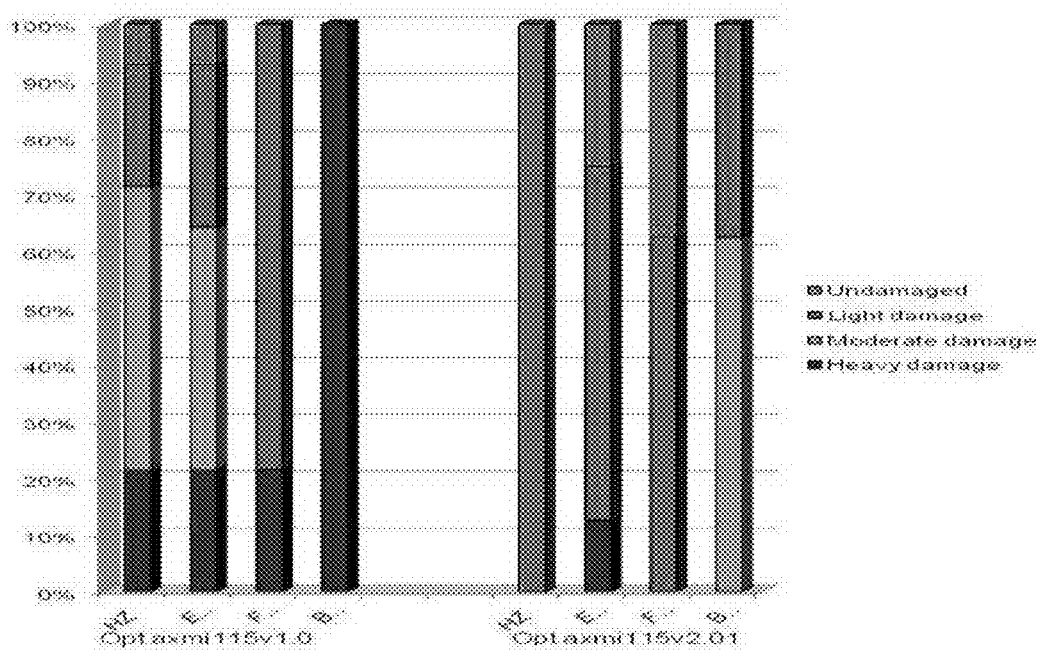
FIG. 2 shows the results of the in vitro leaf disk bioassay. pAG6585 contains optAxmi115v01 (N=14) and pAG6141 contains optAxmi115v02.01.01 (N=8).
Figure 2:
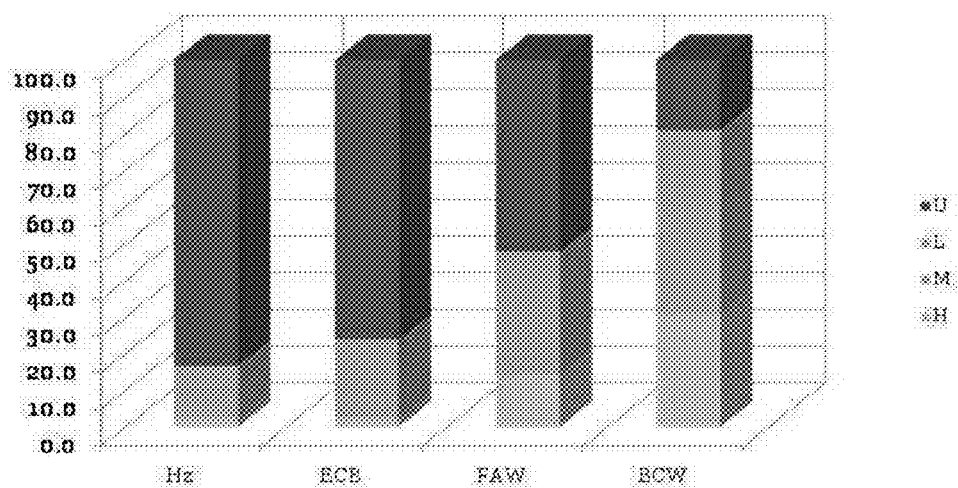

Leaf material from PCR and western positive plants was assayed in in vitro leaf disk bioassay. FIG. 2A shows the percent PCR positive plants that gave a bioassay score of undamaged, light damage, moderate damage or heavy damage for each construct. Western blots indicate that the expression level of protein in plants expressing optAxmi115v02.01 is, in general, higher than plants expressing Axmi115v01.

Additional transgenic plants were produced expressing Axmi115v02.01. Leaf material from PCR and Western positive plants was assayed in in vitro leaf disk bioassay against Hz, ECB, FAW, and BCW. The results are shown in FIG. 2b.

Plant Field Trials

Plants expressing the genes shown in Table 6 were planted at the Polk County, Iowa test location. Negative segregates were identified and removed using a 1× application of Glyphosate (20 oz./A of Buccaneer 5, Tenkoz, Inc.) when plants were at the V3-V4 leaf stage. Insect pressure resulted from manual infestations of ECB, Hz, and FAW.

Infestations of ECB mimicked the natural occurrence of first and second generations. For ECB, in total, approximately 340 larvae were infested into either the leaf whorls (first generation, ECB1) or leaf axils (second generation, ECB2) of each plant. ECB1 was evaluated by the Guthrie 1-9 rating scale. ECB2 was a measure of the total length of stalk tunneling measured in cm.

Twenty Hz larvae were infested onto the tips of primary ears on each plant. There was also a moderate natural infestation of Hz that augmented these manual infestations. The ear damage was measured in sq. cm.

Approximately 60 FAW larvae were infested into the leaf whorls. Damage was measured in Modified Davis 1-9 rating scale as described below.

The results of these field trials are shown in Table 6.

TABLE 6

Field trial results

| | FAW (1-9) | | Hz (sq. cm) | | ECB2 (cm) | |
|---|---|---|---|---|---|---|
| | Mean Score | SD | Mean Score | SD | Mean score | SD |
| Axmi115v02.01 | 1.20 | 0.48 | 0.12 | 0.15 | 0.00 | 0.00 |
| Axmi115v01 | 1.92 | 1.18 | 1.96 | 1.40 | 0.83 | N/A |
| Axmi005 | 1.75 | 0.97 | 4.12 | 2.06 | N/A | N/A |
| neg. Control | 6.42 | 0.74 | 7.06 | 1.61 | 9.65 | 1.66 |

FAW—Modified Davis 1-9 Rating Scale Description.
1. No visible damage or only pinhole lesions present on whorl leaves.
2. Pinhole and small circular lesions present on whorl leaves.
3. Small circular lesions and a few small elongated (rectangular-shaped) lesions of up to 1.3 cm (½") in length present on whorl and furl leaves.
4. Several small to mid-sized 1.3 to 2.5 cm (½" to 1") in length elongated lesions present on a few whorl and furl leaves.
5. Several large elongated lesions greater than 2.5 cm (1") in length present on a few whorl and furl leaves and/or a few small- to mid-sized uniform to irregular shaped holes (basement membrane consumed) eaten from the whorl and/or furl leaves.
6. Several large elongated lesions present on several whorl and furl leaves and/or several large uniform to irregular shaped holes eaten from furl/whorl leaves.
7. Many elongated lesions of all sizes present on several whorl and furl leaves plus several large uniform to irregular shaped holes eaten from the whorl and furl leaves.
8. Many elongated lesions of all sizes present on most whorl and furl leaves plus many mid- to large-sized uniform to irregular shaped holes eaten from the whorl and furl leaves.
9. Whorl and furl leaves almost totally destroyed.
Davis, F. M., S. S. Ng, and W. P. Williams. 1992. Visual rating scales for screening whorl-stage corn for resistance to fall armyworm. Miss. Agric. Forestry Exp. Stn. Tech. Bull. 186.
ECB—Guthrie 1-9 Rating Scale Description.
 1. No visible leaf injury.
 2. Small amount of shot-hole injury on a few leaves.
 3. Shot-hole injury common on several leaves.
 4. Several leaves with shot-holes and elongated lesions.
 5. Several leaves with elongated lesions.
 6. Several leaves with elongated lesions about 2.5 cm long.
 7. Long lesions common on about one-half of the leaves.
 8. Long lesions common on about two-thirds of the leaves.
 9. Most leaves with long lesions.
Guthrie, W. D., F. F. Dicke, and C. R. Neiswander. 1960. Leaf and sheath feeding resistance to the European corn borer in eight inbred lines of dent corn. Ohio. Agric. Exp. Sta. Res. Bull. 860.

Example 2. Directed Evolution of Axmi115v02

Directed evolution has been used to improve the potency and activity profile of Axmi115 against ECB, Hz, FAW, BCW, and VBC. To identify regions of Axmi115 involved in insect toxicity, a number of Axmi115/Axmi005 sequence swap variants in the C-terminal part of Axmi115 were created. Twenty-one blocks of sequence divergence between Axmi115 and Axmi005 were designated (see U.S. Patent Publication No. 20100004176 which is herein incorporated by reference in its entirety) and these sequence blocks in Axmi115 were replaced with the corresponding Axmi005 sequence blocks. Bioassays of hybrid proteins showed that substitutions in blocks 2, 3, 10 and 18 are linked to increased insect toxicity.

Point mutant libraries were created that targeted positions in blocks 2, 3, 10 and 18. These point mutant libraries were assayed against ECB, Hz, FAW, BCW and VBC at 1.5× coverage at the 4 replicate level. Re-assays were carried out at the 4 replicate level, and scale-ups were done at the 16 replicate level. The following point mutants showed improved activity against one or more pests:

TABLE 7

Activity of Axmi115 point mutants

| | nucleotide SEQ ID NO: | amino acid SEQ ID NO: | Activity improved against | Slight improvement in activity against |
|---|---|---|---|---|
| Block2 L11C7 | 9 | 23 | FAW | Hz, ECB, BCW |
| Block 2 L11H6 | | 24 | FAW | Hz, ECB |
| Block 2 L11H7 | 10 | 25 | FAW | Hz, ECB, BCW |
| Block 2 L11A9 | 11 | 26 | FAW | ECB, BCW |
| Block 2 L11F9 | | 27 | ECB | BCW, FAW |
| Block 2 L11G10 | 12 | 28 | Hz, FAW | |
| Block 2 L12C3 | 13 | 29 | Hz, FAW | |
| Block 18 L12A10 | 14 | 30 | FAW | ECB, VBC |
| Block 18 L12B10 | | 31 | FAW | ECB |

These variants contain mutations in the C-terminal part. To look for synergistic improvements with Axmi115v02 (pAX6307), the C-terminal part of several of the above mutants was cloned into Axmi115v02 (pAX6307). Scale-up assays were carried out and variants with improved activity compared to Axmi115v02 were identified.

TABLE 8

Activity of Axmi115v02 mutants

| | Gene | | | | | | | | | |
|---|---|---|---|---|---|---|---|---|---|---|
| | ECB | | FAW | | VBC | | Hz | | BCW | |
| | Stunt | % Mort | Stunt | % Mort | Stunt | % Mort | Stunt | % Mort | Stunt | % Mort |
| axmi-115 v02 | 3.50 | 14.84 | 3.75 | 45.31 | 4.00 | 72.27 | 4.00 | 16.67 | 2.08 | 4.17 |
| 115B2L11H6 (v02) - evo27 | 3.67 | 13.02 | 3.67 | 52.08 | 4.00 | 84.38 | 4.00 | 35.16 | 1.50 | 0.00 |
| 115B18L12B10 (v02) - evo28 | 3.33 | 15.63 | 3.67 | 26.56 | 4.00 | 60.94 | 4.00 | 1.56 | 2.25 | 0.00 |
| 115B2L11H7 (v02) | 3.33 | 10.94 | 3.67 | 33.33 | 4.00 | 56.77 | 4.00 | 3.91 | 2.00 | 0.00 |
| 115B18L12A10 (v02) | 3.33 | 16.15 | 3.67 | 27.08 | 4.00 | 60.94 | 4.00 | 0.78 | 2.13 | 0.00 |
| 115B2L11F9 (v02) - evo29 | 3.67 | 6.88 | 3.67 | 54.17 | 4.00 | 86.98 | 4.00 | 34.38 | 1.38 | 3.13 |

Variant axmi115 B2L11H6 (v02) shows improved activity against *H. zea*, VBC, FAW. It was designated Axmi115v02(evo27). The nucleotide sequence for Axmi115v02(evo27) is set forth in SEQ ID NO:4 and the encoded amino acid sequence is set forth in SEQ ID NO:18.

Variant axmi115 B18L12B10 (v02) shows improvements against ECB. It was designated Axmi115v02(evo28). The nucleotide sequence for Axmi115v02(evo28) is set forth in SEQ ID NO:5 and the encoded amino acid sequence is set forth in SEQ ID NO:19.

Variant axmi115 B2L11F9 (v02) shows improvements against *H. zea*, VBC, FAW. It was designated Axmi115v02 (evo29). The nucleotide sequence for Axmi115v02(evo29) is set forth in SEQ ID NO:6 and the encoded amino acid sequence is set forth in SEQ ID NO:20.

Additional mutations were made in the AXMI115v02 sequence in the C-terminal region. Three variants were identified with improved activity relative to AXMI115v02 (Table 9). LC50 and EC50 values were determined for two of these C-terminal mutants (Table 10).

AXMI115v02(EV031) showed improved mortality against FAW, soybean looper (SBL) and VBC relative to AXMI115v02. The nucleotide sequence for Axmi115v02 (evo31) is set forth in SEQ ID NO:7 and the amino acid sequence is set forth in SEQ ID NO:21.

AXMI115v02(EV032) showed improved mortality against ECB and *H. zea* relative to AXMI115v02. The nucleotide sequence for Axmi115v02(evo32) is set forth in SEQ ID NO:8 and the amino acid sequence is set forth in SEQ ID NO:22.

AXMI115v02(EV038) showed improved mortality against BCW relative to AXMI115v02. The nucleotide sequence for Axmi115v02(evo38) is set forth in SEQ ID NO:47 and the amino acid sequence is set forth in SEQ ID NO:48.

TABLE 9

Activity of Axmi115v02 C-terminal mutants

| | Gene | | | | | | | | | |
|---|---|---|---|---|---|---|---|---|---|---|
| | ECB | | FAW | | VBC | | Hz | | BCW | |
| | Stunt | % Mort | Stunt | % Mort | Stunt | % Mort | Stunt | % Mort | Stunt | % Mort |
| Axmi115v02 | 3.3 | 11.5 | 4.0 | 16.5 | 4.0 | 80.2 | 4.0 | 13.8 | 2.8 | 1.1 |
| Axmi115v02(evo31) | 3.4 | 28.6 | 4.0 | 20.7 | 4.0 | 81.4 | 4.0 | 14.3 | 2.4 | 0.0 |
| Axmi115v02(evo32) | 3.4 | 30.0 | 4.0 | 18.2 | 4.0 | 94.4 | 4.0 | 35.0 | 3.0 | 0.0 |
| Axmi115v02(evo38) | 0.2 | 0.0 | 4.0 | 15.7 | 4.0 | 87.1 | 4.0 | 10.5 | 3.6 | 6.6 |

TABLE 10

LC50 and EC50 for C-terminal mutants

| | Gene | | | | | | | | |
|---|---|---|---|---|---|---|---|---|---|
| | ECB | | FAW | | VBC | SBL | Hz | | BCW |
| | LC50 | EC50 | LC50 | EC50 | LC50 | LC50 | LC50 | EC50 | LC50 |
| Axmi115v02 | 20 µg/ml | 3 µg/ml | 6.3 µg/ml | 1.3 µg/ml | 400 ng/ml | 280 ng/ml | 339 ng/ml | 14.3 µg/ml | 7.6 µg/ml |
| Axmi115v02 (evo31) | 18 µg/ml | 4.5 µg/ml | 2.4 µg/ml | 240 ng/ml | 120 ng/ml | 80 ng/ml | 185 µg/ml | | 12 µg/ml | 27.3 µg/ml |
| Axmi115v02 (evo32) | 12.3 µg/ml | 4.3 µg/ml | 6 µg/ml | 400 ng/ml | 520 ng/ml | 520 ng/ml | 42.5 µg/ml | 13.3 µg/ml | 16.6 µg/ml |

SBL = Soybean looper

Example 3. Additional Assays for Pesticidal Activity

The nucleotide sequences of the invention can be tested for their ability to produce pesticidal proteins. The ability of a pesticidal protein to act as a pesticide upon a pest is often assessed in a number of ways. One way well known in the art is to perform a feeding assay. In such a feeding assay, one exposes the pest to a sample containing either compounds to be tested or control samples. Often this is performed by placing the material to be tested, or a suitable dilution of such material, onto a material that the pest will ingest, such as an artificial diet. The material to be tested may be composed of a liquid, solid, or slurry. The material to be tested may be placed upon the surface and then allowed to dry. Alternatively, the material to be tested may be mixed with a molten artificial diet, and then dispensed into the assay chamber. The assay chamber may be, for example, a cup, a dish, or a well of a microtiter plate.

Assays for sucking pests (for example aphids) may involve separating the test material from the insect by a partition, ideally a portion that can be pierced by the sucking mouth parts of the sucking insect, to allow ingestion of the test material. Often the test material is mixed with a feeding stimulant, such as sucrose, to promote ingestion of the test compound.

Other types of assays can include microinjection of the test material into the mouth, or gut of the pest, as well as development of transgenic plants, followed by test of the ability of the pest to feed upon the transgenic plant. Plant testing may involve isolation of the plant parts normally consumed, for example, small cages attached to a leaf, or isolation of entire plants in cages containing insects.

Other methods and approaches to assay pests are known in the art, and can be found, for example in Robertson and Preisler, eds. (1992) *Pesticide bioassays with arthropods*, CRC, Boca Raton, Fla. Alternatively, assays are commonly described in the journals *Arthropod Management Tests and Journal of Economic Entomology* or by discussion with members of the Entomological Society of America (ESA).

In some embodiments, the DNA regions encoding the toxin region of the pesticidal proteins disclosed herein are cloned into the *E. coli* expression vector pMAL-C4x behind the malE gene coding for Maltose binding protein (MBP). These in-frame fusions result in MBP-Axmi fusion proteins expression in *E. coli*.

For expression in *E. coli*, BL21*DE3 are transformed with individual plasmids. Single colonies are inoculated in LB supplemented with carbenicillin and glucose, and grown overnight at 37° C. The following day, fresh medium is inoculated with 1% of overnight culture and grown at 37° C. to logarithmic phase. Subsequently, cultures are induced with 0.3 mM IPTG overnight at 20° C. Each cell pellet is suspended in 20 mM Tris-Cl buffer, pH 7.4+200 mM NaCl+1 mM DTT+protease inhibitors and sonicated. Analysis by SDS-PAGE can be used to confirm expression of the fusion proteins.

Total cell free extracts are then run over amylose column attached to fast protein liquid chromatography (FPLC) for affinity purification of MBP-axmi fusion proteins. Bound fusion proteins are eluted from the resin with 10 mM maltose solution. Purified fusion proteins are then cleaved with either Factor Xa or trypsin to remove the amino terminal MBP tag from the Axmi protein. Cleavage and solubility of the proteins can be determined by SDS-PAGE

Example 4. Construction of Synthetic Sequences

In one aspect of the invention, synthetic axmi sequences are generated. These synthetic sequences have an altered DNA sequence relative to the parent axmi sequence, and encode a protein that is collinear with the parent AXMI protein to which it corresponds, but lacks the C-terminal "crystal domain" present in many delta-endotoxin proteins.

In another aspect of the invention, modified versions of synthetic genes are designed such that the resulting peptide is targeted to a plant organelle, such as the endoplasmic reticulum or the apoplast. Peptide sequences known to result in targeting of fusion proteins to plant organelles are known in the art. For example, the N-terminal region of the acid phosphatase gene from the White Lupin *Lupinus albus* (Genebank ID GI:14276838; Miller et al. (2001) Plant Physiology 127: 594-606) is known in the art to result in endoplasmic reticulum targeting of heterologous proteins. If the resulting fusion protein also contains an endoplasmic retention sequence comprising the peptide N-terminus-lysine-aspartic acid-glutamic acid-leucine (i.e. the "KDEL" motif (SEQ ID NO:46) at the C-terminus, the fusion protein will be targeted to the endoplasmic reticulum. If the fusion protein lacks an endoplasmic reticulum targeting sequence at the C-terminus, the protein will be targeted to the endoplasmic reticulum, but will ultimately be sequestered in the apoplast.

Example 5. Transformation of Maize Cells with the Pesticidal Protein Genes Described Herein Maize ears are best collected 8-12 days after pollination. Embryos are isolated from the ears, and those embryos 0.8-1.5 mm in size are preferred for use in transformation. Embryos are plated scutellum side-up on a suitable incubation media, such as DN62A5S media (3.98 g/L N6 Salts; 1 mL/L (of 1000× Stock) N6 Vitamins; 800 mg/L L-Asparagine; 100 mg/L Myo-inositol; 1.4 g/L L-Proline; 100 mg/L Casamino acids; 50 g/L sucrose; 1 mL/L (of 1 mg/mL Stock) 2,4-D). However, media and salts other than DN62A5S are suitable and are known in the art. Embryos are incubated overnight at 25° C. in the dark. However, it is not necessary per se to incubate the embryos overnight.

The resulting explants are transferred to mesh squares (30-40 per plate), transferred onto osmotic media for about 30-45 minutes, then transferred to a beaming plate (see, for example, PCT Publication No. WO/0138514 and U.S. Pat. No. 5,240,842).

DNA constructs designed to the genes of the invention in plant cells are accelerated into plant tissue using an aerosol beam accelerator, using conditions essentially as described in PCT Publication No. WO/0138514. After beaming, embryos are incubated for about 30 min on osmotic media, and placed onto incubation media overnight at 25° C. in the dark. To avoid unduly damaging beamed explants, they are incubated for at least 24 hours prior to transfer to recovery media. Embryos are then spread onto recovery period media, for about 5 days, 25° C. in the dark, then transferred to a selection media. Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated by methods known in the art. The resulting shoots are allowed to root on rooting media, and the resulting plants are transferred to nursery pots and propagated as transgenic plants.

Materials

| DN62A5S Media | | |
|---|---|---|
| Components | Per Liter | Source |
| Chu's N6 Basal Salt Mixture (Prod. No. C 416) | 3.98 g/L | Phytotechnology Labs |
| Chu's N6 Vitamin Solution (Prod. No. C 149) | 1 mL/L (of 1000x Stock) | Phytotechnology Labs |
| L-Asparagine | 800 mg/L | Phytotechnology Labs |
| Myo-inositol | 100 mg/L | Sigma |
| L-Proline | 1.4 g/L | Phytotechnology Labs |
| Casamino acids | 100 mg/L | Fisher Scientific |
| Sucrose | 50 g/L | Phytotechnology Labs |
| 2,4-D (Prod. No. D-7299) | 1 mL/L (of 1 mg/mL Stock) | Sigma |

The pH of the solution is adjusted to pH 5.8 with 1N KOH/1N KCl, Gelrite (Sigma) is added at a concentration up to 3 g/L, and the media is autoclaved. After cooling to 50° C., 2 ml/L of a 5 mg/ml stock solution of silver nitrate (Phytotechnology Labs) is added.

Example 6. Transformation of Genes of the Invention in Plant Cells by *Agrobacterium*-Mediated Transformation Ears are best collected 8-12 days after pollination. Embryos are isolated from the ears, and those embryos 0.8-1.5 mm in size are preferred for use in transformation. Embryos are plated scutellum side-up on a suitable incubation media, and incubated overnight at 25° C. in the dark. However, it is not necessary per se to incubate the embryos overnight. Embryos are contacted with an *Agrobacterium* strain containing the appropriate vectors for Ti plasmid mediated transfer for about 5-10 min, and then plated onto co-cultivation media for about 3 days (25° C. in the dark). After co-cultivation, explants are transferred to recovery period media for about five days (at 25° C. in the dark). Explants are incubated in selection media for up to eight weeks, depending on the nature and characteristics of the particular selection utilized. After the selection period, the resulting callus is transferred to embryo maturation media, until the formation of mature somatic embryos is observed. The resulting mature somatic embryos are then placed under low light, and the process of regeneration is initiated as known in the art.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A recombinant nucleic acid molecule comprising a nucleotide sequence encoding a polypeptide having pesticidal activity, wherein said nucleotide sequence is selected from the group consisting of:
   a) the nucleotide sequence set forth in SEQ ID NO:7; and
   b) a nucleotide sequence that encodes a polypeptide comprising the amino acid sequence of SEQ ID NO: 21.

2. The recombinant nucleic acid molecule of claim 1, wherein said nucleotide sequence is a synthetic sequence that has been designed for expression in a plant.

3. The recombinant nucleic acid molecule of claim 1, wherein said nucleotide sequence is operably linked to a promoter capable of directing expression of said nucleotide sequence in a plant cell.

4. A vector comprising the recombinant nucleic acid molecule of claim 1.

5. The vector of claim 4, further comprising a nucleic acid molecule encoding a heterologous polypeptide.

6. A host cell that contains the recombinant nucleic acid of claim 1.

7. The host cell of claim 6 that is a bacterial host cell.

8. The host cell of claim 6 that is a plant cell.

9. A transgenic plant comprising the host cell of claim 8.

10. The transgenic plant of claim 9, wherein said plant is selected from the group consisting of maize, sorghum, wheat, cabbage, sunflower, tomato, crucifers, peppers, potato, cotton, rice, soybean, sugarbeet, sugarcane, tobacco, barley, and oilseed rape.

11. A transgenic seed comprising the nucleic acid molecule of claim 1.

12. A recombinant polypeptide having pesticidal activity, wherein said polypeptide comprises the amino acid sequence of SEQ ID NO: 21.

13. The polypeptide of claim 12 further comprising heterologous amino acid sequences.

14. A composition comprising the polypeptide of claim 12.

15. The composition of claim 14, wherein said composition is selected from the group consisting of a powder, dust, pellet, granule, spray, emulsion, colloid, and solution.

16. The composition of claim 14, wherein said composition is prepared by desiccation, lyophilization, homogenization, extraction, filtration, centrifugation, sedimentation, or concentration of a culture of bacterial cells.

17. The composition of claim 14, comprising from about 1% to about 99% by weight of said polypeptide.

18. A method for controlling a lepidopteran pest population comprising contacting said population with a pesticidally-effective amount of the polypeptide of claim 12.

19. A method for killing a lepidopteran pest, comprising contacting said pest with, or feeding to said pest, a pesticidally-effective amount of the polypeptide of claim 12.

20. A method for producing a polypeptide with pesticidal activity, comprising culturing the host cell of claim 6 under conditions in which the nucleic acid molecule encoding the polypeptide is expressed.

21. A plant or a plant cell having stably incorporated into its genome a DNA construct comprising a nucleic acid molecule comprising a nucleotide sequence encoding a polypeptide having pesticidal activity, wherein the nucleotide sequence is selected from the group consisting of:
   a) the nucleotide sequence of SEQ ID NO:7; and
   b) a nucleotide sequence that encodes a polypeptide comprising the amino acid sequence of SEQ ID NO:21.

22. A method for protecting a plant from a pest, comprising introducing into a plant or cell thereof a nucleic acid molecule comprising a nucleotide sequence encoding a polypeptide having pesticidal activity, wherein the nucleotide sequence is selected from the group consisting of:
   a) the nucleotide sequence of SEQ ID NO:7; and
   b) a nucleotide sequence that encodes a polypeptide comprising the amino acid sequence of SEQ ID NO:21.

23. The method of claim 22, wherein said plant produces a pesticidal polypeptide having pesticidal activity against a lepidopteran pest.

24. A method for increasing yield in a plant comprising growing in a field a plant or a seed thereof having stably incorporated into its genome a DNA construct comprising a nucleic acid molecule comprising a nucleotide sequence encoding a polypeptide having pesticidal activity, wherein the nucleotide sequence is selected from the group consisting of:

a) the nucleotide sequence of SEQ ID NO: 7; and b) a nucleotide sequence that encodes a polypeptide comprising the amino acid sequence of SEQ ID NO:21;

wherein the yield of said plant is increased relative to the yield of a plant that does not comprises the nucleotide sequence of either of (a) or (b).

\* \* \* \* \*